United States Patent
Krasutsky et al.

(10) Patent No.: US 7,199,114 B2
(45) Date of Patent: Apr. 3, 2007

(54) TRITERPENE QUATERNARY SALTS AS BIOLOGICALLY ACTIVE SURFACTANTS

(75) Inventors: Pavel A. Krasutsky, Duluth, MN (US); Dmytro Avilov, Duluth, MN (US); Tatiana Sergeeva, Gainesville, FL (US); Dmytro A. Krasutskyy, Duluth, MN (US); Oksana Kolomitsyna, Duluth, MN (US)

(73) Assignee: The Regents of the University of Minnesota, Minneapolis, MN (US)

( * ) Notice: Subject to any disclaimer, the term of this patent is extended or adjusted under 35 U.S.C. 154(b) by 142 days.

(21) Appl. No.: 10/893,147

(22) Filed: Jul. 16, 2004

(65) Prior Publication Data

US 2005/0059642 A1  Mar. 17, 2005

Related U.S. Application Data

(63) Continuation of application No. PCT/US03/01666, filed on Jan. 21, 2003.

(60) Provisional application No. 60/349,564, filed on Jan. 18, 2002.

(51) Int. Cl.
*A61K 31/56* (2006.01)
*A61K 31/14* (2006.01)
*C07J 53/00* (2006.01)
*C07C 211/00* (2006.01)

(52) U.S. Cl. ............ 514/169; 514/642; 552/510; 564/281

(58) Field of Classification Search ........ 552/510; 514/169, 642; 564/281
See application file for complete search history.

(56) References Cited

U.S. PATENT DOCUMENTS 3,872,091 A * 3/1975 Hewett et al. ............. 540/96
5,182,373 A    1/1993 Kim et al. ................. 536/4.1

FOREIGN PATENT DOCUMENTS

FR  2261763  9/1975
GB  1498239  1/1978

OTHER PUBLICATIONS

Matuszalewska et al., "Nitrogen derivatives of triterpenes. IX. Synthesis of methyl derivatives of epimeric 3-amino taraxastanes". Roczniki Chemii, vol. 47(4), pp. 853-858, 1973, English Abstract.*

* cited by examiner

*Primary Examiner*—Barbara P. Badio
(74) *Attorney, Agent, or Firm*—Schwegman, Lundberg, Woessner & Kluth P.A.

(57) ABSTRACT

The invention provides novel compounds that are quaternary amine derivatives of betulin and other triterpenes. The compounds have antibacterial, antifungal, and surfactant properties.

48 Claims, No Drawings

TRITERPENE QUATERNARY SALTS AS BIOLOGICALLY ACTIVE SURFACTANTS

RELATED APPLICATIONS

This application is a continuation under 35 U.S.C. 111(a) of International Application No. PCT/US03/01666 filed Jan. 21, 2003 and published in English as WO 03/062260 on Jul. 31, 2003, which claimed priority from Provisional Application No. 60/349,564 filed Jan. 18, 2002, which applications and publication are incorporated herein by reference.

BACKGROUND OF THE INVENTION

Outer layers of plants such as leaf cuticles, fruit peels, and bark protect the plant against abrasion, prevent water loss, and protect against pathogenic microorganisms. Breaking through the plant protective outer layer is a prerequisite for a pathogen to enter the plant's internal tissues. Some studies have suggested that penetration of the protective layer involves dissolution of the host cuticle by enzymes secreted by the pathogen. Nicholson, R. L. et al., in *The Fungal Spore and Disease Initiation in Plants and Animals*, eds. Cole, G. T., and Hoch, H. C., 1991, Plenum Press, New York, pp. 3–23.

Pentacyclic triterpenes are among the most common plant secondary metabolites, but their function in plants has not been fully understood. They are usually concentrated in the outermost layers such as plant cuticle, fruit peel, and bark.

Betulin is a pentacyclic triterpenoid derived from the outer bark of paper birch trees (*Betula papyrifera, B. pendula, B. verucosa*, etc.). It can be present at concentrations of up to about 24% of the bark of white birch. Merck Index, twelfth edition, page 1236 (1996). Lupeol is a related compound also found in birch bark and in other plant sources. Lupeol is present at concentrations of about 1.5–3% of the birch bark and at up to about 8.2% in *Canavalia ensiformis*, a plant widespread in the humid tropics of Asia and Africa. Allobetulin is another triterpenoid found in birch bark. A typical pulp mill that process birch produces enough bark waste to allow for the inexpensive isolation of significant quantities of these triterpenoids.

Literature supplies examples of enzymes that can be inhibited by triterpenes, indicating the ability of triterpenes to act broadly in a non-specific mode on multiple targets. For example, Buchler et al. (Biochem. Biophys. Acta 1075, 206 (1991) showed inhibition of rat renal 11β-hydroxysteroid dehydrogenase. Koch et al. (Phytother, Res. 8, 109 (1994)) showed in vitro inhibition of adenosine deaminase. This leads to the hypothesis that pentacyclic triterpenoids in plant protective outer layers may protect against infection by inhibiting enzymes that would degrade the cuticle.

Several triterpenoids have been found to have utility. For example, betulin and related compounds have been shown to have anti-viral activity against herpes simplex virus. Carlson et al., U.S. Pat. No. 5,750,578. Betulin and related compounds have also been shown to have anti-fungal and anti-bacterial activity. However, triterpenoids are hydrophobic compounds with relatively low interfacial activity and water solubility. For instance, the solubility of betulin in water is about 0.15 mg/l. The relatively low interfacial activity and water solubility can make handling and administration of the compounds difficult. Low interfacial activity also limits the efficient interaction with target (fungi or bacteria) cell membranes. It also limits accessibility to hydrophilic biological targets or targets protected by a hydrophilic barrier.

There is a need for new compounds with anti-fungal, and anti-bacterial activities. Preferably the compounds would be relatively water soluble surfactants. The water-soluble compounds would retain their utility, e.g., antifungal, antibacterial, etc., activity.

SUMMARY OF THE INVENTION

The present invention provides novel compounds useful for their anti-fungal and anti-bacterial properties. The compounds have the advantage of being derived from abundant and relatively inexpensive starting materials. They have the further advantage of being based on natural compounds, and thus being less likely to pose a risk to the environment, humans, or beneficial organisms. They have the further advantage of being relatively water soluble and amphiphilic. This makes the compounds easier to handle and reduces the use of hazardous organic solvents. It also increases accessibility to hydrophilic biological targets, or to targets present in water or protected by a hydrophilic barrier. The amphiphilic character of the compounds allows them to bind hydrophobic targets, and may allow them to adsorb on cytoplasmic membranes. A further advantage of the compounds is that they are stable and do not tend to readily hydrolyze.

The present invention provides a quaternary ammonium salt of a triterpene.

The present invention further provides a compound of formula (I):

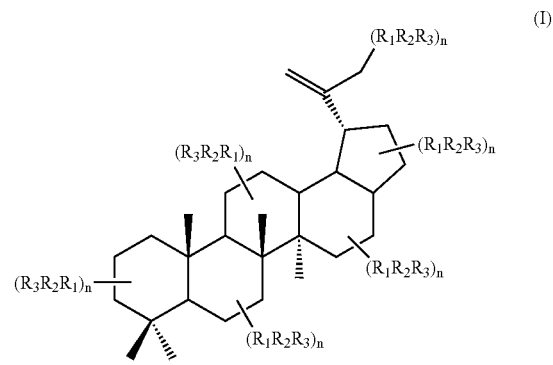

wherein each $R_1$ is independently absent, oxy, thio, or imino. Each $R_2$ is independently absent or alkylene. Each $R_3$ is independently hydrogen, $N^+$-containing heteroaryl, $N^+$-containing heterocycle, or $-N^+R_aR_bR_c$; provided at least one $R_3$ is $N^+$-containing heteroaryl, $N^+$-containing heterocycle, or $-N^+R_aR_bR_c$. Each n is independently 0–4 inclusive, provided at least one n is not 0. $R_a$, $R_b$, and $R_c$ are each independently $(C_1–C_{24})$alkyl, aryl, arylalkyl, heteroarylalkly, heterocycle, or heterocylealkyl. Any heteroaryl, heterocycle, $R_a$, $R_b$, or $R_c$ of $R_3$ can optionally be substituted on carbon with one or more alkyl, hydroxyalkyl, arylalkyl, heteroarylalkyl, aryl, heterocycle, heterocyclealkyl, oxo, hydroxy, halo, nitro, cyano, $(C_1–C_6)$alkoxy, trifluoromethyl, —$COOR_d$, —$NR_dR_e$, or cycloalkylalkyl. $R_d$ and $R_e$ are each independently hydrogen or alkyl. Any cycloalkylalkyl can optionally be substituted on carbon with one or more hydroxyl, $N^+$-containing heteroaryl, $N^+$-containing heterocycle, or —$N^+R_aR_bR_c$, $N^+$-containing heteroarylalkyloxy, $N^+$-containing heterocyclealkyloxy, or —$N^+R_aR_bR_c$oxy. Any alkyl or alkylene of $R_3$ can optionally be substituted on carbon with one or more oxo, hydroxy, halo, nitro, cyano, $(C_1–C_6)$alkoxy, trifluoromethyl, —$COOR_d$, or —$NR_dR_e$, and optionally interrupted on carbon with one or more oxy, imino, or thio, and is optionally partially unsaturated. The invention also provides acceptable salts of a compound of formula (I).

The present invention further provides a compound of formula (II):

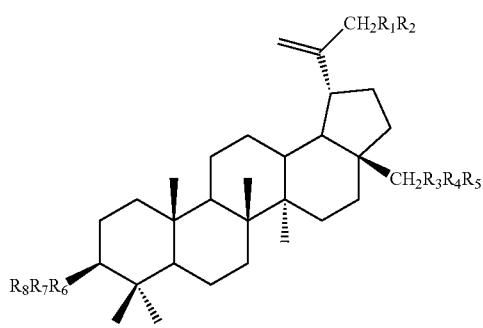

(II)

In formula (II), $R_1$, $R_4$, and $R_7$ are each independently absent or alkylene. $R_3$ and $R_6$ are each independently absent, oxy, thio, or imino. $R_2$, $R_5$, and $R_8$ are each independently hydrogen, $N^+$-containing heteroaryl, $N^+$-containing heterocycle, or —$N^+R_aR_bR_c$; provided at least one of $R_2$, $R_5$, and $R_8$ is $N^+$-containing heteroaryl, $N^+$-containing heterocycle, or —$N^+R_aR_bR_c$. $R_a$, $R_b$, and $R_c$ are each independently $(C_1–C_{24})$alkyl, aryl, arylalkyl, heteroarylalkly, heterocycle, or heterocylealkyl. Any heteroaryl, heterocycle, or $R_a$, $R_b$, or $R_c$ of $R_2$, $R_5$, and $R_8$ can optionally be substituted on carbon with one or more alkyl, hydroxyalkyl, arylalkyl, heteroarylalkyl, aryl, heterocycle, heterocyclealkyl, oxo, hydroxy, halo, nitro, cyano, $(C_1–C_6)$alkoxy, trifluoromethyl, —$COOR_d$, —$NR_dR_e$, or cycloalkylalkyl. $R_d$ and $R_e$ are each independently hydrogen or alkyl. Any cycloalkylalkyl can optionally be substituted on carbon with one or more hydroxyl, $N^+$-containing heteroaryl, $N^+$-containing heterocycle, —$N^+R_aR_bR_c$, $N^+$-containing heteroarylalkyloxy, $N^+$-containing heterocyclealkyloxy, or —$N^+R_aR_bR_c$oxy. Any alkyl or alkylene of $R_1$, $R_2$, $R_4$, $R_5$, $R_7$, or $R_8$ can be optionally substituted on carbon with one or more oxo, hydroxy, halo, nitro, cyano, $(C_1–C_6)$alkoxy, trifluoromethyl, —$COOR_d$, or —$NR_dR_e$, and optionally interrupted on carbon with one or more oxy, imino, or thio, and is optionally partially unsaturated. The invention also provides acceptable salts of a compound of formula (II).

The present invention further provides a compound of formula (III)

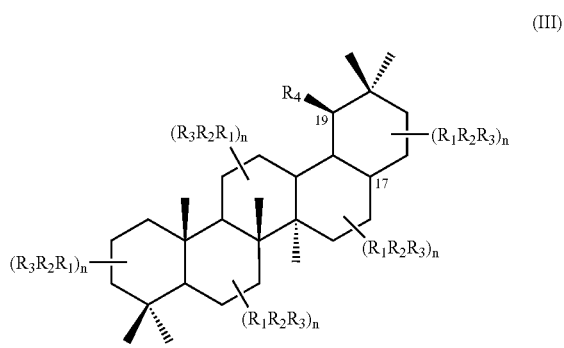

(III)

In formula (III), each $R_1$ is independently absent, oxy, thio, or imino. Each $R_2$ is independently absent or alkylene. Each $R_3$ is independently hydrogen, $N^+$-containing heteroaryl, $N^+$-containing heterocycle, or —$N^+R_aR_bR_c$; provided at least one $R_3$ is $N^+$-containing heteroaryl, $N^+$-containing heterocycle, or —$N^+R_aR_bR_c$. $R_4$ is hydrogen, alkyl, or hydroxyalkyl. Alternatively, $R_4$ together with one $R_1R_2R_3$ forms a —$OCH_2$— bridging carbons 19 and 17. Each n is independently 0–4 inclusive, provided at least one n is not 0. $R_a$, $R_b$, and $R_c$ are each independently $(C_1–C_{24})$alkyl, aryl, arylalkyl, heteroarylalkyl, heterocycle, or heterocylealkyl. Any heteroaryl, heterocycle, $R_a$, $R_b$, or $R_c$ of $R_3$ can optionally be substituted on carbon with one or more alkyl, hydroxyalkyl, arylalkyl, heteroarylalkyl, aryl, heterocycle, heterocyclealkyl, oxo, hydroxy, halo, nitro, cyano, $(C_1–C_6)$alkoxy, trifluoromethyl, —$COOR_d$, —$NR_dR_e$ or cycloalkylalkyl. $R_d$ and $R_e$ are each independently hydrogen or alkyl. Any cycloalkylalkyl can optionally be substituted on carbon with one or more hydroxyl, $N^+$-containing heteroaryl, $N^+$-containing heterocycle, —$N^+R_aR_bR_c$, $N^+$-containing heteroarylalkyloxy, $N^+$-containing heterocyclealkyloxy, or —$N^+R_aR_bR_c$oxy. Any alkyl or alkylene of $R_3$ can optionally be substituted on carbon with one or more oxo, hydroxy, halo, nitro, cyano, $(C_1–C_6)$alkoxy, trifluoromethyl, —$COOR_d$, or —$NR_dR_e$, and optionally interrupted on carbon with one or more oxy, imino, or thio, and is optionally partially unsaturated. The invention also provides acceptable salts of a compound of formula (III).

The present invention further provides a compound of formula (IV):

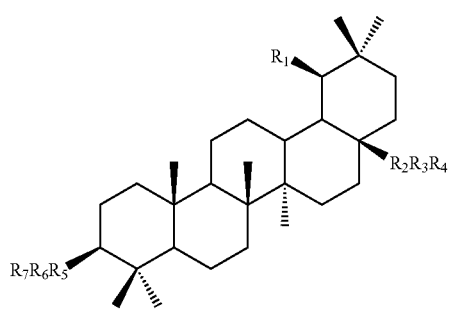

In formula (IV) $R_1$ is hydrogen, alkyl, or hydroxyalkyl. $R_2$ is oxymethylene, thiomethylene, iminomethylene, or methylene. $R_3$ and $R_6$ are each independently absent or alkylene. $R_4$ and $R_7$ are each independently hydrogen, $N^+$-containing heteroaryl, $N^+$-containing heterocycle, or —$N^+R_aR_bR_c$; provided at least one of $R_4$ and $R_7$ is $N^+$-containing heteroaryl, $N^+$-containing heterocycle, or —$N^+R_aR_bR_c$. Alternatively $R_1$, $R_2$, $R_3$, and $R_4$ are together —O—C(=X)—; wherein X is two hydrogens, oxo, or thioxo (=S). $R_5$ is absent, oxy, thio, or imino. $R_a$, $R_b$, and $R_c$ are each independently $(C_1–C_{24})$alkyl, aryl, arylalkyl, heteroarylalkly, heterocycle, or heterocylealkyl. Any heteroaryl, heterocycle, $R_a$, $R_b$, or $R_c$ of $R_4$ and $R_7$ can optionally be substituted on carbon with one or more alkyl, hydroxyalkyl, arylalkyl, heteroarylalkyl, aryl, heterocycle, heterocyclealkyl, oxo, hydroxy, halo, nitro, cyano, $(C_1–C_6)$alkoxy, trifluoromethyl, —COOR$_d$, —NR$_d$R$_e$, or cycloalkylalkyl, wherein any cycloalkylalkyl can optionally be substituted on carbon with one or more hydroxyl, $N^+$-containing heteroaryl, $N^+$-containing heterocycle, —$N^+R_aR_bR_c$, $N^+$-containing heteroarylalkyloxy, $N^+$-containing heterocyclealkyloxy, or —$N^+R_aR_bR_c$oxy. $R_d$ and $R_e$ are each independently hydrogen or alkyl. Any alkyl or alkylene of $R_3$, $R_4$, $R_6$, or $R_7$ can be optionally substituted on carbon with one or more oxo, hydroxy, halo, aryl, nitro, cyano, $(C_1–C_6)$alkoxy, trifluoromethyl, COOR$_d$, or —NR$_d$R$_e$, and optionally interrupted on carbon with one or more oxy, imino, or thio, and is optionally partially unsaturated.

The present invention further provides a method of inhibiting or killing a fungus comprising contacting the fungus with an effective anti-fungal amount of a compound of formula (I)–(IV).

The present invention further provides a method of inhibiting or killing a bacterium comprising contacting the bacterium with an effective anti-bacterial amount of a compound of formula (I)–(IV).

DETAILED DESCRIPTION OF THE INVENTION

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Alkyl and alkylene are defined herein as $(C_1–C_6)$alkyl or $(C_1–C_6)$ alkylene unless specified otherwise. The alkyl or alkylene portion of other groups, e.g., alkoxy, cycloalkyl, etc., is also defined herein as comprising 1–6 carbons unless otherwise specified. Aryl denotes a phenyl radical or an ortho-fused bicyclic carbocyclic radical having about nine to ten ring atoms in which at least one ring is aromatic. Heteroaryl encompasses a radical attached via a ring atom of a monocyclic aromatic ring containing five or six ring atoms consisting of carbon and one to four heteroatoms each selected from the group consisting of non-peroxide oxygen, sulfur, and N(X) wherein X is absent or is H, O, $(C_1–C_4)$ alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. $N^+$-containing heteroaryl can be attached via a nitrogen atom of the heteroaryl ring, or via another ring atom. If attached via another ring atom, the one or more nitrogens of the ring can optionally be derivatized with one or two alkyl or hydroxyalkyl groups to make the nitrogen quaternary. Heterocycle encompasses a radical attached via a ring atom, wherein the ring can be a single ring, ortho-fused rings, or bicyclic rings, and wherein the ring system is non-aromatic. The heterocycle ring preferably comprises 5–20 atoms, of which preferably one to four are heteratoms each selected from the group consisting of non-peroxide oxygen, sulfur, and N(X) wherein X is absent or is H, O, $(C_1–C_6)$alkyl, phenyl or benzyl. The ring system can optionally be substituted. The ring system can optionally be partially unsaturated.

The term "cycloalkyl" encompasses a radical attached via a ring atom of a non-aromatic cyclic ring system, wherein the ring system comprises one to five ortho-fused rings, each ring consisting of 4–10 carbon atoms. The ring system can optionally be substituted. The ring system can optionally be partially unsaturated.

The term "acceptable salt" refers to a salt comprising one of the cationic compounds of the invention and an acceptable anion. An acceptable anion is an anion that does not interfere with the functioning of the compound. For instance, in pharmaceutical uses, an acceptable anion is one that does not have any significant deleterious effect on the health of the patient. In agricultural use of the compounds of the invention as anti-fungal agents, an accetable anion is one that does not interfere with the antifungal properties of the compounds and does not have a deleterious effect on plant health. Preferred cations include chloride, bromide, and iodide. Other preferred cations include organic cations, such as formate, acetate, propionate, or butyrate.

The term "N-diazabicyclo[2.2.2]octyl" refers to the group

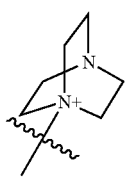

The term "N-pyridinium" refers to the group

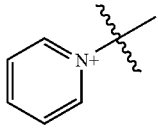

The term "N-methyl-N-piperidino" refers to the group

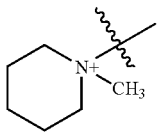

The term "N-methyl-N-morpholino" refers to the group

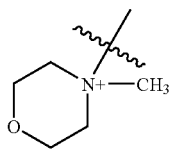

The term "N-azabicyclo[2.2.2]octyl" refers to the group

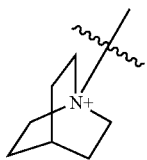

The term "bacterium" or "bacteria" refers to any prokaryotic organism. See *Biology of Microogranisms*, 6th ed., Brock, T. D., and Madigan, M. T., (1991), pp. 9–11.

The term "fungus" refers to a distinct group of eukaryotic, spore-forming organisms with absorptive nutrition and lacking chlorophyll. The term includes mushrooms, molds, and yeasts. See id., pp. 817–822.

The term "triterpene" refers to one of a class of compounds having approximately 30 carbon atoms and synthesized from six isoprene units in plants and other organisms. Triterpenes consist of carbon, hydrogen, and optionally oxygen. Most triterpenes are secondary metabolites in plants. Most, but not all, triterpenes are pentacyclic. Examples of triterpenes include betulin, allobetulin, lupeol, friedelin, and all sterols, including lanosterol, stigmasterol, cholesterol, β-sitosterol, and ergosterol.

The term "quaternary ammonium salt" refers to a compound comprising at least one positively charged nitrogen atom with four covalent bonds to non-hydrogen atoms. Typically the four bonds will be to carbon atoms. Two or three of the bonds can make up a double or triple bond respectively to a single atom.

The term "quaternary ammonium salt of a triterpene" refers to triterpene covalently attached to a group comprising at least one positively charged nitrogen atom with four covalent bonds to non-hydrogen atoms. Examples of quaternary ammonium salts of a triterpene include a compound of formulas (I)–(IV).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-fungal or anti-bacterial activity using the standard tests described herein, or using other similar tests which are well known in the art.

Specific and preferred values listed here for radicals, substituents, and ranges, are for illustration only; they do not exclude other defined values or other values within defined ranges for the radicals and substituents Specifically, alkyl can be methyl, ethyl, propyl, isopropyl, butyl, iso-butyl, sec-butyl, pentyl, 3-pentyl, or hexyl. Cycloalkyl can be cyclopropyl, cyclobutyl, cyclopentyl, cyclohexyl, or the triterpene ring system of betulin, allobetulin, or lupeol. Cycloalkylalkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl, or a synthetically feasible radical derived from a compound of formula (V) or (VI).

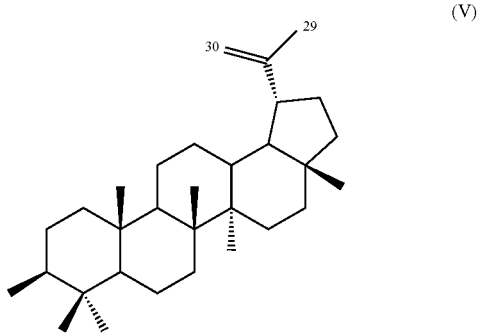

(VI)

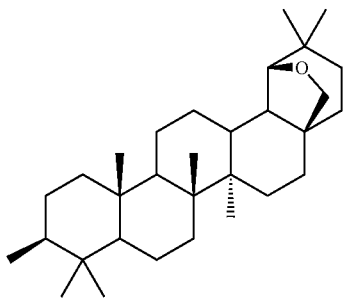

The synthetically feasible radical derived from a compound of formula (V) or (VI) can be formed by removal of a hydrogen or methyl from any suitable carbon atom on the compound, or by hydrolysis of the ether bridge of compound (VI) followed by removal of a hydrogen from resultant hydroxyl, methyl, or methylene. The point of attachment thus can be a side chain methyl, a ring methylene, a ring methylidyne, carbons 29 or 30 of the side chain isopropylene of compound (V), or a methylene, oxymethyl, or oxy formed from the product of hydrolysis of the ether bridge of compound (VI).

($C_1$–$C_6$)alkoxy can be methoxy, ethoxy, propoxy, isopropoxy, butoxy, iso-butoxy, sec-butoxy, pentoxy, 3-pentoxy, or hexyloxy. ($C_1$–$C_5$)alkylenecarbonyl can be acetyl, propionyl, butyryl, pentanoyl, or hexanoyl.

Alkylene can be methylene, ethylene, propylene, butylene, pentamethylene, or hexamethylene.

$N^+$-containing heteroaryl can be N-pyridinium, N-methyl-2-pyridinium, N-methyl-3-pyridinium, N-methyl-4-pyridinium, N-ethyl-2-pyridinium, N-ethyl-3-pyridinium, N-ethyl-4-pyridinium, 3,5-dimethylpyridinium, or 4-(dimethylamino)pyridinium.

$N^+$-containing heterocycle can be N-diazabicyclo[2.2.2]octyl; N-azabicyclo[2.2.2]octyl; N-methyl-N-piperidino; N,N-dimethyl-2-piperidino; N,N-dimethyl-3-piperidino; N,N-dimethyl-4-piperidino; N-methyl-N-morpholino; N,N-dimethyl-2-morpholino; or N,N-dimethyl-3-morpholino.

Hydroxyalkyl can be hydroxymethyl, hydroxyethyl, 3-hydroxypropyl, 2-hydroxypropyl, 1-hydroxyisopropyl, 4-hydroxybutyl, 5-hydroxypentyl, or 6-hydroxyhexyl.

Arylalkyl can be benzyl, phenylethyl, phenylpropyl, phenylbutyl, or phenylpentyl.

—$N^+$—$R_aR_bR_c$ can be N'-benzyl-N,N,N',N'-tetramethylethylenediamine-N-yl; N,N,N',N'-tetramethylethylenediamine-N-yl; octyldimethylammonium; tetradecyldimethylammonium; trimethylammonium; triethylammonium, or tri(hydroxymethyl)ammonium.

The present invention is directed to triterpenes derivatized with $N^+$-containing groups. The compounds of the invention are found to be rather resistant to hydrolysis. Derivatization with $N^+$-containing groups is also found to make the compounds of the invention rather water soluble. For instance, the solubility of some quaternary salts of betulin disclosed herein is 400–600 g/l.

In one specific embodiment of a compound of formula (I), at least one $R_3$ is —$N^+R_aR_bR_c$ wherein $R_a$ and $R_b$ are each independently ($C_6$–$C_{24}$)alkyl optionally substituted on carbon with one or more oxo, hydroxy, halo, cyano, ($C_1$–$C_6$) alkoxy, trifluoromethyl, —$COOR_d$, or —$NR_dR_e$, and optionally interrupted on carbon with one or more oxy, imino, or thio, and optionally partially unsaturated. In particular compounds of this embodiment, one $R_3$ is —$N^+R_a R_bR_c$ and the other $R_3$s are hydrogen.

In one specific embodiment of a compound of formula (II), $R_2$, $R_5$, and $R_8$ are each independently absent, hydroxyl, N-diazabicyclo[2.2.2]octyl, N-pyridinium, N-alkyl-N-piperidino, N-alkyl-N-morpholino, N-azabicyclo[2.2.2]octyl, or —$N^+R_aR_bR_c$; provided at least one of $R_2$, $R_5$, and $R_8$ is $N^+$-containing heteroaryl, $N^+$-containing heterocycle, or —$N^+R_aR_bR_c$. In this embodiment N-diazabicyclo[2.2.2]octyl; N-pyridinium; N-alkyl-N-piperidino; N-alkyl-N-morpholino; and N-azabicyclo[2.2.2]octyl can optionally be substituted on one or more suitable carbon atoms with one or more oxo, hydroxy, mercapto, alkyl, hydroxyalkyl, halo, nitro, cyano, ($C_1$–$C_6$)alkoxy, —$COOR_d$, or —$NR_dR_e$. In this embodiment also, any alkyl or alkylene of $R_1$, $R_2$, $R_4$, $R_5$, $R_7$, or $R_8$ can optionally be substituted with one or more oxo or —$NR_dR_e$, and optionally interrupted with one or more oxy, imino, or thio, and can optionally be partially unsaturated.

In another specific embodiment of a compound of formula (II), $R_1$ is absent and $R_2$ is hydrogen, N-diazabicyclo[2.2.2] octyl, or N-dimethylamino-N-pyridinium.

In another specific embodiment of a compound of formula (II), $R_3$ and $R_4$ are absent, and $R_5$ is hydrogen.

In another specific embodiment of a compound of formula (II), $R_3$ is oxy; $R_4$ is absent or ($C_1$–$C_5$)alkylenecarbonyl; and $R_5$ is hydrogen, N-diazabicyclo[2.2.2]octyl; 4-dimethylamino-N-pyridinium; 4-hydroxybutyl-N-diazabicyclo [2.2.2]octyl; 4-benzyl-N-diazabicyclo[2.2.2]octyl; tetramethylethylenediamine-N-yl; N'-benzyl-N,N,N',N'-tetramethylethylenediamine-N-yl; N-pyridinium; 4-hydroxymethyl-N-pyridinium; 2,4-dimethyl-N-pyridinium; 3,5-dimethyl-N-pyridinium; octyldimethylammonium; or tetradecyldimethylammonium.

In another specific embodiment of a compound of formula (II), $R_6$ is oxy; $R_7$ is absent or ($C_1$–$C_5$)alkylenecarbonyl; and $R_8$ is hydrogen, N-diazabicyclo[2.2.2]octyl; 4-dimethylamino-N-pyridinium; N'-(4-hydroxybutyl)-N-diazabicyclo [2.2.2]octyl; N'-benzyl-N-diazabicyclo[2.2.2]octyl; N,N,N', N'-tetramethylethylenediamine-N-yl; N'-benzyl-N,N,N',N'-tetramethylethylenediamine-N-yl; N-pyridinium; 4-hydroxymethyl-N-pyridinium; 2,4-dimethyl-N-pyridinium; 3,5-dimethyl-N-pyridinium; octyldimethylammonium; tetradecyldimethylammonium; 2-methyl-N-pyridinium; 4-hydroxy-N-methyl-N-piperidinium; or N-methyl-N-morpholino.

In particular embodiments of the invention, the compound of formula (II) is:

lup-20(29)-ene-3,28-bis-(N-pyridiniumacetate);

lup-20(29)-ene-3-[N-(4-oxybutyl)-1,4-diazabicyclo[2.2.2] octyl-N'-acetate];

lup-20(29)-ene-3,28-bis[N-(1,4-diazabicyclo[2.2.2]octyl) acetate];

lup-20(29)-ene-3,28-bis[N-(N'-benzyldiazabicyclo[2.2.2] octyl)acetate);

lup-20(29)-ene-3,28-bis[N-(N'-(4-oxybutyl)diazabicyclo [2.2.2]octyl)acetate];
lup-20(29)-ene-3-[N-(1,4-diazabicyclo[2.2.2]octyl)acetate];
lup-20 (29)-ene-3,28-bis[(tetramethyletylenediamine-N-yl) acetate];
lup-20(29)-ene-3,28-bis[N'-benzyl-N,N,N',N'-tetramethyl-ethylenediamine-N-yl)acetate];
lup-20(29)-ene-3-[N-(N'-(benzyl)diazabicyclo[2.2.2]octyl) acetate];
bis(N,N'-pyridinium-2-ethyl)lup-20(29)ene-3,28-dicarbamate;
1-(3,28-(diacetoxy)lup-20(29)-ene-30-yl)4-(dimethylamino)pyridinium;
lup-20(29)-ene-3,28-bis(N-pyridinium-2-propionate);
lup20(29)-ene-3,28-bis(N-pyridinium-3-propionate);
lup-20(29)-ene-3,28-bis(N-pyridinium-4-butyrate);
lup-20(29)-ene-3,28-bis(N-pyridinium-4-butyrate);
lup-20(29)-ene-3,28-bis(N-pyridinium-2-butyrate);
1-[3,28-(diacetoxy)lup-20(29)-ene-30-yl]-1,4-diazabicyclo [2.2.2]octyl;
3,28-bis[3-(1-piperidinyl)propanoyloxy]lup-20(29)-ene;
1-(3,28-dihydroxylup-20(29)ene-30-yl)-4-(dimethylamino) pyridinium;
lup-20(29)-ene-3,28-bis[N-(4-dimethylaminopyridinium)-2-propionate];
lup-20(29)-ene-3,28-bis[N-(1,4-diazabicyclo[2.2.2]octyl)-2-propionate];
1-(lup-20(29)-ene-30-yl)-1,4-diazabicyclo[2.2.2]octane;
1-(3,28-dihydroxylup-20(29)-ene-30-yl)-pyridinium;
lup-20(29)-ene-3,28-bis[N-(1,4-diazabicyclo[2.2.2]octyl)-4-butyrate];
1-(3,28-dihydroxylup-20 (29)-ene-30-yl)-[N-3-(hydroxymethyl)pyridinium];
1-(3,28-dihydroxylup-20(29)-ene-30-yl)-[N-(3,5-dimethylpyridinium)];
bis[N-(1,4-diazabicyclo[2.2.2]octyl)-2-ethyl]-lup-20(29) ene-3,28-dicarbamate;
lup-20(29)-ene-3,28-bis[N-(3-oxymethylpyridinium)acetate];
lup-20(29)-ene-3,28-bis[N-(2-oxymethylpyridinium)acetate];
lup-20(29)-ene-3,28-bis[N-(2-methylureapyridinium)acetate];
lup-20(29)-ene-3-[N-(2-oxymethylpyridinium)acetate];
lup-20(29)-ene-3,28-bis[N-(N-methylmorpholino)acetate];
lup-20(29)-ene-3,28-bis[N-(4-hydroxyl-N-methylpiperidino)acetate];
lup-20(29)-ene-3-[N-(3-ureamethylpyridinium)acetate];
lup-20(29)-ene-3-(N-pyridiniumacetate);
lup-20(29)-ene-3,28-bis[N-(1,4-diazabicyclo[2.2.2]octyl)-2-butyrate];
lup-20(29)-ene-3,28-bis[N-(4-dimethylpyridinium)-2-butyrate];
lup-20(29)-ene-3,28-bis[N-(4-dimethylaminopyridinium)-4-butyrate];
lup-20(29)-ene-3,28-bis[N-(4-dimethylaminopyridinium)-3-propionate];
1-(3,28-dihydroxylup-20(29)-ene-30-yl)-4-(hydroxymethyl)pyridinium;
1-(3,28-dihydroxylup-20(29)-ene-30-yl)-3-hydroxy-1-azabicyclo[2.2.2]octane;
lup-20(29)-ene-3,28-bis[N-(2,4-dimethylpyridinium)acetate];
lup-20(29)-ene-3,28-bis[N-(3,5-dimethylpyridinium)acetate];
lup-20(29)-ene-3,28-bis[N-(4-dimethylaminopyridinium) acetate];
lup-20(29)-ene-3-[N-(2-methylpyridinium)acetate];
lup-20(29)ene-3-[N-(2,4-dimethylpyridinium)acetate];
lup-20(29)-ene-3-[N-(4-hydroxy-N-methylpiperidino)acetate];
lup-20(29)-ene-3-[N-(N-methylmorpholino)acetate];
lup-20(29)-ene-3-[N-(3,5-dimethylpyridinium)acetate];
lup-20(29)-ene-3-[N-(4-dimethylaminopyridinium)acetate];
lup-20(29)-ene-3,28-bis(octyldimethylammoniumacetate);
lup-20(29)-ene-3-octyldimethylammoniumacetate;
lup-20(29)-ene-3,28-bis(tetradecyldimethylammoniumacetate);
lup-20(29)-ene-3-tetradecyldimethylammoniumacetate;
N,N,N',N'-tetramethylethylenediamine-N,N'-bis-[lup-20 (29)-ene-3-acetate];
1-[(lup-20(29)-en-3β-yl)oxycarbonylmethyl]4-aza-1-azonia-bicyclo[2.2.2]octane;
1-[(lup-20(29)-en-3β-yl)oxycarbonylmethyl]trimethylammonium; or
1-[(lup-20(29)-en-3β-yl)oxycarbonylmethyl]pyridinium.

A specific embodiment of the compound of formula (II) is the compound wherein at least one of $R_2$, $R_5$, and $R_8$ is —N⁺$R_aR_bR_c$ wherein $R_a$ and $R_b$ are each independently ($C_6$–$C_{24}$)alkyl optionally substituted on carbon with one or more oxo, hydroxy, halo, cyano, ($C_1$–$C_6$)alkoxy, trifluoromethyl, —COOR$_d$, or —NR$_d$R$_e$, and optionally interrupted on carbon with one or more oxy, imino, or thio, and optionally partially unsaturated. In more particular embodiments, $R_a$ and $R_b$ are each ($C_6$–$C_{24}$)alkyl, or are each ($C_8$–$C_24$)alkyl, or are each ($C_{10}$–$C_{24}$)alkyl.

In a specific embodiment of a compound of formula (II) wherein at least one of $R_2$, $R_5$, and $R_8$ is —N⁺$R_aR_bR_c$ wherein $R_a$ and $R_b$ are each independently ($C_6$–$C_{24}$)alkyl optionally substituted on carbon with one or more oxo, hydroxy, halo, cyano, ($C_1$–$C_6$)alkoxy, trifluoromethyl, —COOR$_d$, or —N⁺$R_dR_e$, and optionally interrupted on carbon with one or more oxy, imino, or thio, and optionally partially unsaturated, $R_1$ is absent and $R_2$ is hydrogen.

In a specific embodiment of a compound of formula (II), the cation of the cation of the compound is betulin-3,28-bis (didecylmethylammoniumacetoxy).

In a specific embodiment of a compound of formula (II), wherein at least one of $R_2$, $R_5$, and $R_8$ is —N⁺$R_aR_bR_c$ wherein $R_a$ and $R_b$ are each independently ($C_6$–$C_{24}$)alkyl optionally substituted on carbon with one or more oxo, hydroxy, halo, cyano, ($C_1$–$C_6$)alkoxy, trifluoromethyl, —COOR$_d$, or —NR$_d$R$_e$, and optionally interrupted on carbon with one or more oxy, imino, or thio, and optionally partially unsaturated, $R_1$ is absent and $R_2$ is hydrogen, $R_3$ is absent or oxy, $R_4$ is absent, and $R_5$ is hydrogen. In another specific embodiment, $R_6$ is oxy, $R_7$ is absent, and $R_8$ is hydrogen.

In a specific embodiment of a compound of formula (II), the cation of the compound is betulin-3-(didecylmethylammoniumacetoxy).

In a specific embodiment of a compound of formula (II), $R_3$ is absent, or oxy.

In a particular embodiment of a compound of formula (II), $R_4$ is absent or alkylene optionally substituted on carbon with one or more oxo, hydroxy, halo, nitro, cyano, ($C_1$–C6) alkoxy, trifluoromethyl, —COOR$_d$, or —NR$_d$R$_e$, and optionally interrupted on carbon with one or more oxy, imino, or thio, and is optionally partially unsaturated. In a specific embodiment, $R_4$ is acetyl.

In a particular embodiment of the compound of formula (II), $R_5$ is —N$^+$R$_a$R$_b$R$_c$ wherein R$_a$ and R$_b$ are each ($C_6$–$C_{24}$) alkyl optionally substituted on carbon with one or more oxo, hydroxy, halo, cyano, ($C_1$–$C_6$)alkoxy, trifluoromethyl, —COOR$_d$, or —NR$_d$R$_e$, and optionally interrupted on carbon with one or more oxy, imino, or thio, and optionally partially unsaturated. In a more specific embodiment, $R_5$ is —N$^+$R$_a$R$_b$R$_c$ wherein R$_a$ and R$_b$ are each ($C_6$–$C_{24}$)alkyl. In a more specific embodiment, $R_4$ is —N$^+$R$_a$R$_b$R$_c$ wherein R$_a$ and R$_b$ are each ($C_6$–$C_{24}$)alkyl and R$_a$ is ($C_1$–$C_{24}$)alkyl. In a more specific embodiment, $R_5$ is —N$^+$R$_a$R$_b$R$_c$ wherein R$_a$ and R$_b$ are each ($C_6$–$C_{24}$)alkyl and R$_c$ is ($C_1$–$C_6$)alkyl.

In a specific embodiment of a compound of formula (II), $R_6$ is absent, or oxy.

In a particular embodiment of a compound of formula (II), $R_7$ is absent or alkylene optionally substituted on carbon with one or more oxo, hydroxy, halo, nitro, cyano, ($C_1$–$C_6$) alkoxy, trifluoromethyl, —COOR$_d$, or —NR$_d$R$_e$, and optionally interrupted on carbon with one or more oxy, imino, or thio, and is optionally partially unsaturated. In a specific embodiment, $R_7$ is acetyl.

In a particular embodiment of the compound of formula (II), R$_a$ is —N$^+$R$_a$R$_b$R$_c$ wherein R$_a$ and R$_b$ are each ($C_6$–$C_{24}$) alkyl optionally substituted on carbon with one or more oxo, hydroxy, halo, cyano, ($C_1$–$C_6$)alkoxy, trifluoromethyl, —COOR$_d$, or —NR$_d$R$_e$, and optionally interrupted on carbon with one or more oxy, imino, or thio, and optionally partially unsaturated. In a more specific embodiment, $R_8$ is —N$^+$R$_a$R$_b$R$_c$ wherein R$_a$ and R$_b$ are each ($C_6$–$C_{24}$)alkyl. In a more specific embodiment, $R_4$ is —N$^+$R$_a$R$_b$R$_c$ wherein R$_a$ and R$_b$ are each ($C_6$–$C_{24}$)alkyl and R$_a$ is ($C_1$–$C_{24}$)alkyl. In a more specific embodiment, $R_8$ is —N$^+$R$_a$R$_b$R$_c$ wherein R$_a$ and R$_b$ are each ($C_6$–$C_{24}$)alkyl and R$_c$ is ($C_1$–C6)alkyl.

A specific embodiment of the compound of formula (III) is the compound wherein at least one $R_3$ is —N$^+$R$_a$R$_b$R$_c$ wherein R$_a$ and R$_b$ are each independently ($C_6$–$C_{24}$)alkyl optionally substituted on carbon with one or more oxo, hydroxy, halo, cyano, ($C_1$–$C_6$)alkoxy, trifluoromethyl, —COOR$_d$, or —NR$_d$R$_e$, and optionally interrupted on carbon with one or more oxy, imino, or thio, and optionally partially unsaturated. In specific compounds of this embodiment, R$_a$ and R$_b$ are each ($C_6$–$C_{24}$)alkyl, are each ($C_8$–$C_{24}$) alkyl, or are each ($C_{10}$–$C_{24}$)alkyl. In other specific compounds of this embodiment, one $R_3$ is —N$^+$R$_a$R$_b$R$_c$ and the other $R_3$s are hydrogen.

A specific embodiment of the compound of formula (IV) is the compound wherein $R_1$ is hydrogen, alkyl, or hydroxyalkyl; $R_2$ is oxymethylene, thiomethylene, iminomethylene, or methylene; $R_3$ and $R_6$ are each independently absent or alkylenecarbonyl; $R_4$ and $R_7$ are each independently hydrogen, N-diazabicyclo[2.2.2]octyl; N-pyridinium; N-alkyl-N-piperidino; N-alkyl-N-morpholino; N-azabicyclo[2.2.2]octyl; or —N$^+$R$_a$R$_b$R$_c$; or $R_1$, $R_2$, $R_3$, and $R_4$ are together —O—CH$_2$—. In this case, N-diazabicyclo[2.2.2]octyl; N-pyridinium; N-alkyl-N-piperidino; N-alkyl-N-morpholino; and N-azabicyclo[2.2.2]octyl can optionally be substituted on carbon with one or more alkyl, hydroxyalkyl, hydroxy, COOR$_d$, or NR$_d$R$_e$. R$_a$, R$_b$, and R$_c$ are each independently aryl or ($C_1$–$C_{24}$)alkyl; wherein R$_d$ and R$_e$ are each independently hydrogen or alkyl. Any alkylene or alkyl can optionally be substituted on carbon with one or more oxo, hydroxy, halo, nitro, cyano, trifluoromethyl, COOR$_d$, or —NR$_d$R$_e$, and optionally interrupted with one or more oxy, imino, or thio, and where any alkyl or alkylene can optionally be partially unsaturated.

Another specfic embodiment of the compound of formula (IV) is the compound wherein $R_1$, $R_2$, $R_3$, and $R_4$ are together —O—CH$_2$—.

Another specific embodiment of the compound of formula (IV) is the compound wherein $R_5$ is oxy.

Another specific embodiment of the compound of formual (IV) is the compound wherein $R_6$ is acetyl.

Another specific embodiment of the compound of formual (IV) is the compound wherein $R_7$ is N-diazabicyclo[2.2.2] octyl; N-pyridinium; or —N$^+$(CH$_3$)$_3$.

In particular embodiments of the invention, the compound of formula (IV) is:

1-[(19β,28-epoxy-18α-oleanan-3β-yl)oxycarbonylmethyl]-4-aza-1-azonia-bicyclo[2.2.2]octane;

[(19β,28-epoxy-18α-oleanan-3β-yl)oxycarbonylmethyl]trimethylammonium; or

1-[(19β,28-epoxy-18α-oleanan-3β-yl)oxycarbonylmethyl] pyridinium.

In a specific embodiment of the compound of formula (IV), at least one of $R_4$ and $R_7$ is —N$^+$R$_a$R$_b$R$_c$ wherein R$_a$ and R$_b$ are each ($C_6$–$C_{24}$)alkyl optionally substituted on carbon with one or more oxo, hydroxy, halo, cyano, ($C_1$–$C_6$) alkoxy, trifluoromethyl, —COOR$_d$, or —NR$_d$R$_e$, and optionally interrupted on carbon with one or more oxy, imino, or thio, and optionally partially unsaturated.

In a more specific embodiment of the compound of formula (IV), at least one of $R_4$ and $R_7$ is —N$^+$R$_a$R$_b$R$_c$ wherein R$_a$ and R$_b$ are each ($C_6$–$C_{24}$)alkyl optionally substituted on carbon with one or more oxo, hydroxy, halo, cyano, ($C_1$–$C_6$)alkoxy, trifluoromethyl, —COOR$_d$, or —NR$_d$R$_e$, and optionally interrupted on carbon with one or more oxy, imino, or thio, and optionally partially unsaturated, $R_5$ is oxy, thio, or imino; $R_6$ is alkylene optionally substituted on carbon with one or more oxo, hydroxy, halo, cyano, ($C_1$–$C_6$)alkoxy, trifluoromethyl, or —NR$_d$R$_e$, and optionally interrupted on carbon with one or more oxy, imino, or thio, and is optionally partially unsaturated; and $R_7$ is —N$^+$R$_a$R$_b$R$_c$ wherein R$_a$ and R$_b$ are each ($C_6$–$C_{24}$)alkyl optionally substituted on carbon with one or more oxo, hydroxy, halo, cyano, ($C_1$–$C_6$)alkoxy, trifluoromethyl, —COOR$_d$, or —NR$_d$R$_e$, and optionally interrupted on carbon with one or more oxy, imino, or thio, and optionally partially unsaturated.

In a particular embodiment of the compound of formula (IV), $R_5$ is oxy.

In a particular embodiment of the compound of formula (IV), $R_6$ is alkylene optionally substituted on carbon with one or more oxo, hydroxy, halo, cyano, ($C_1$–$C_6$)alkoxy, trifluoromethyl, or —NR$_d$R$_e$, and optionally interrupted on carbon with one or more oxy, imino, or thio, and is optionally partially unsaturated. In a more specific embodiment, $R_6$ is alkylene optionally substituted with one or more oxo. In a more specific embodiment, $R_6$ is acetyl.

In a particular embodiment of the compound of formula (IV), $R_7$ is $-N^+R_aR_bR_c$ wherein $R_a$ and $R_b$ are each $(C_6-C_{24})$alkyl optionally substituted on carbon with one or more oxo, hydroxy, halo, cyano, $(C_1-C_6)$alkoxy, trifluoromethyl, $-COOR_d$, or $-NR_dR_e$, and optionally interrupted on carbon with one or more oxy, imino, or thio, and optionally partially unsaturated. In a more specific embodiment, $R_7$ is $-N^+R_aR_bR_c$ wherein $R_a$ and $R_b$ are each $(C_6-C_{24})$alkyl. In a more specific embodiment, $R_7$ is $-N^+R_aR_bR_c$ wherein $R_a$ and $R_b$ are each $(C_6-C_{24})$alkyl and $R_c$ is $(C_1-C_{24})$alkyl. In a more specific embodiment, $R_7$ is $-N^+R_aR_bR_c$ wherein $R_a$ and $R_b$ are each $(C_6-C_{24})$alkyl and $R_c$ is $(C_1-C_6)$alkyl.

In a particular embodiment of a compound of formula (IV), $R_2$ is oxymethylene, thiomethylene, iminomethylene, or methylene or $R_1$, $R_2$, $R_3$, and $R_4$ are together $-O-CH_2-$. In another particular embodiment, $R_2$ is oxymethylene or $R_1$, $R_2$, $R_3$, and $R_4$ are together $-O-CH_2-$.

In a particular embodiment of a compound of formula (IV), $R_3$ is absent or alkylene optionally be substituted on carbon with one or more oxo, hydroxy, halo, nitro, cyano, trifluoromethyl, $COOR_d$, or $-NR_dR_e$, and optionally interrupted with one or more oxy, imino, or thio, and optionally be partially unsaturated.

In a particular embodiment of the compound of formula (IV), $R_4$ is $-N^+R_aR_bR_c$ wherein $R_a$ and $R_b$ are each $(C_6-C_{24})$alkyl optionally substituted on carbon with one or more oxo, hydroxy, halo, cyano, $(C_1-C_6)$alkoxy, trifluoromethyl, $-COOR_d$, or $-NR_dR_e$, and optionally interrupted on carbon with one or more oxy, imino, or thio, and optionally partially unsaturated. In a more specific embodiment, $R_4$ is $-N^+R_aR_bR_c$ wherein $R_a$ and $R_b$ are each $(C_6-C_{24})$alkyl. In a more specific embodiment, $R_4$ is $-N^+R_aR_bR_c$ wherein $R_a$ and $R_b$ are each $(C_6-C_{24})$alkyl and R is $(C_1-C_{24})$alkyl. In a more specific embodiment, $R_4$ is $-N^+R_aR_bR_c$ wherein $R_a$ and $R_b$ are each $(C_6-C_{24})$alkyl and $R_c$ is $(C_1-C_6)$alkyl.

In a particular embodiment of a compound of formula (IV), $R_1$ is hydrogen or $R_1$, $R_2$, $R_3$, and $R_4$ are together $-O-CH_2-$.

In a particular embodiment of the compound of formula (IV), the cation of the compound is 3β-[(N-methyl-N,N-didecyl)aminoacetyloxy]-19β,28-epoxy-18α-oleanan chloride.

Another embodiment of the invention provides a method of inhibiting or killing a fungus comprising contacting the fungus with an effective anti-fungal amount of any of the compounds of the invention, e.g., a compound of formulas (I)–(IV). The contacting can be in vitro or in vivo. The contacting can, for example, be on a plant. The contacting can be done on turf grass to kill or inhibit a fungus growing on it. The fungus can be causing the disease dollar spot or brown patch.

Another embodiment of the invention provides a method of inhibiting or killing a bacterium comprising contacting the bacterium with an effective anti-bacterial amount of any one of the compounds of the invention, e.g., a compound of formulas (I)–(IV). The bacterium can be Staphylococcus sp. or Enterococcus sp., for example. The bacterium, for example, can be S. aureus or E. faecium. In one embodiment of the invention, the bacterium is antibiotic resistant.

Another embodiment of the invention provides a pharmaceutical composition comprising any one of the compounds of the invention.

The compounds of the invention comprise one triterpene moiety derivatized with one or more quaternary ammonium group (e.g., $N^+$-containing group). Preferred $N^+$-containing groups include $N^+$-containing heteraryl, $N^+$-containing heterocycle, or $-N^+R_aR_bR_c$, wherein $R_a$, $R_b$, and $R_c$ are each independently $(C_1-C_{24})$alkyl, aryl, arylalkyl, heteroarylalkyl, heterocycle, or hetercyclealkyl. Preferably, a single triterpene moiety is derivatized with one, two, three, or four $N^+$-containing groups.

The compounds of the invention also comprise more than one triterpene moiety derivatized to a single $N^+$-containing group and comprise oligomers of alternating triterpene moieties and $N^+$-containing groups. In these cases, the triterpene moieties can be further derivatized with additional $N^+$-containing groups.

For instance, one embodiment of the invention provides a compound of formula (VII) or (VIII):

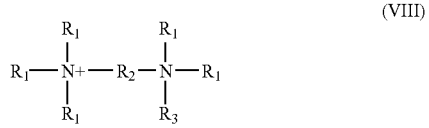

Each $R_1$ is independently $(C_1-C_{24})$alkyl or is alkylcarbonyl attached through the carbonyl to the oxy at the 3 or 28 carbon of betutlin, lupeol, or allobetulin, or to an imino or thio in place of the oxy at the 3 or 28 carbon of betulin, lupeol, or allobetulin, wherein if it is attached to an oxy, imino, or thio at the 28 carbon of allobetulin, carbon 19 is a methylene. $R_2$ is $(C_1-C_{24})$alkyl. $R_3$ is absent or $(C_1-C_{24})$alkyl or is alkylcarbonyl attached through the carbonyl to the oxy at the 3 or 28 carbon of betulin, lupeol, or allobetulin, or to an imino or thio in place of the oxy at the 3 or 28 carbon of betulin, lupeol, or allobetulin, wherein if it is attached to an oxy, imino, or thio at the 28 carbon of allobetulin, carbon 19 is a methylene. In particular embodiments of compound VII, two $R_1$s are $(C_6-C_{24})$alkyl. In particular embodiments of compound VII, at least two $R_1$s are $(C_8-C_{24})$alkyl or $(C_{10}-C_{24})$alkyl. In particular embodiments of compound VIII, at least two $R_1$s attached to either nitrogen atom are $(C_6-C_{24})$alkyl. In particular embodiments of compound VIII, at least two $R_1$s attached to either nitrogen atom are $(C_8-C_{24})$alkyl or $C_{10}-C_{24})$alkyl. Any alkyl or alkylcarbonyl can optionally be substituted with one or more oxo, hydroxy, mercapto, or $NR_dR_e$. $R_d$ and $R_e$ are each independently hydrogen or alkyl. The compound in this case comprises at least two moieties selected from the group of betulin, allobetulin, and lupeol.

In one specific embodiment of the compound of formula (VIII), the compound is N,N,N',N'-tetramethylethylenediamine-N,N'-bis-[lup-20(29)-ene-3-acetate].

The compounds of the invention include one or more triterpene moieties covalently attached via a linker to a quaternary ammonium salt. The linker can attach to the triterpene moiety at any suitable position of the triterpene. The linker can attach to the quaternary ammonium salt at the $N^+$ atom or at any other suitable position. The linker can be, for instance, alkylene, alkylcarbonyl, alkoxy, alkylimino, oxyalkylcarbonyl, carbonylalkylcarbonyl, or carbonylalkyloxy.

The quaternary ammonium salt can also be attached directly to the triterpene without a linker. The attachment in this case can be at any suitable position of the triterpene and any suitable position of the quaternary ammonium salt.

Processes for preparing compounds of formulas (I)–(IV) are provided as further embodiments of the invention and are illustrated by the following procedures in which the meanings of the generic radicals are as given unless otherwise qualified. Specifically, the compounds of formulas (I)–(IV) can be prepared from convenient starting materials, employing procedures (e.g., reagents and reaction conditions) known to those of skill in the art. For example, suitable reagents and reaction-conditions are disclosed, e.g, in *Advanced Organic Chemistry, Part B: Reactions and Synthesis*, Second Edition, Cary and Sundberg (1983); *Advanced Organic Chemistry, Reactions, Mechanisms, and Structure*, Second Edition, March (1977); *Protecting Groups in Organic Synthesis*, Second Edition, Greene, T. W., and Wutz, P. G. M., John Wiley & Sons, New York; and *Comprehensive Organic Transformations*, Larock, R. C., Second Edition, John Wiley & Sons, New York (1999).

The compounds of the invention, e.g., compounds of formulas (I)–(IV), can be formulated as compositions for the treatment or prevention of fungal or bacterial infections of plants. Generally, the compositions comprising compounds of the invention will be applied topically to the plants, generally by spraying. The compositions can also be injected into the plant or applied to the soil for uptake into the plant through the root system. The compositions can comprise an acceptable vehicle, such as an inert diluent or a carrier that facilitates uptake into the plant. Acceptable vehicles are known in the art. Methods of formulating anti-fungal compounds for spraying onto plants are disclosed, for instance in Glinsky et al. (U.S. Pat. No. 6,303,589 B1).

If desired, the compounds of the invention may be applied in conjunction with one or more intert or active ingredients. Exemplary materials include dyes, additives affecting stability of the compositions, additives affecting physical properties of the sprayed layer, foliar fertilizers, fungicides, and insecticides.

The compounds of the invention, e.g. compounds of formulas (I)–(IV), are also useful for cosmetic treatment of nails and adjacent skin infected with fungus in humans. In cosmetic treatment, the compounds of the invention are applied topically to the affected nails and adjacent skin either alone or in a composition with an acceptable carrier. The compounds of the invention can be applied with one or more other inert or active ingredients.

Acceptable salts may be obtained using standard procedures well known in the art, for example by reacting a sufficiently basic compound such as an amine with a suitable acid affording an acceptable anion.

The compounds of formulas (I)–(IV) can be formulated as pharmaceutical compositions and administered to a mammalian host, such as a human patient, in a variety of forms adapted to the chosen route of administration. Typically, the pharmaceutical compositions will be administered topically. They may also be administered, e.g., orally or parenterally, and by intravenous, intramuscular, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formulas (I)–(IV) can be determined by comparing their in vitro activity, and in vivo activity in animal models. Methods for the extrapolation of effective dosages in mice, and other animals, to humans are known to the art; for example, see U.S. Pat. No. 4,938,949.

The ability of a compound of the invention to act as an antibacterial or antifungal agent may be determined using pharmacological models which are well know to the art, including the tests described in the Examples below.

The compounds of the invention may also be useful as pharmacological tools for the further investigation of the mechanism of their antibacterial or antifungal action.

The compounds of the invention can also be administered in combination with other therapeutic agents that are effective to treat bacterial or fungal infections, or to inhibit or kill bacteria or fungi.

The compounds of the invention possess a rigid and hydrophobic fused pentacyclic ring portion, and a hydrophilic quaternary amine portion. Because of their amphiphilic character, they are also useful as surfactants. Their activity as surfactants may be the basis for their antibacterial and antifungal activities, by for instance, adsorbing to cytoplasmic membranes.

The structures and carbon numbering of three exemplary triterpenes used as starting materials in the synthesis of the triterpene quaternary ammonium salts of the invention are shown below.

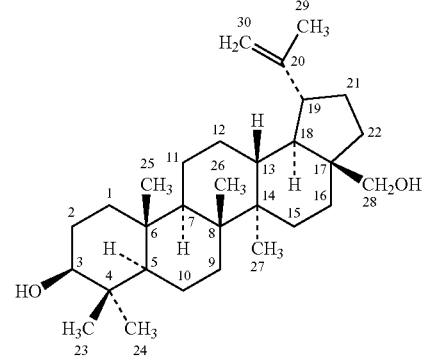

Betulin

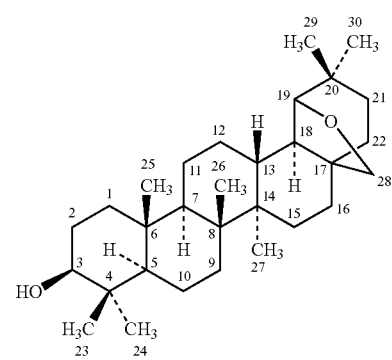

Allobetulin

-continued

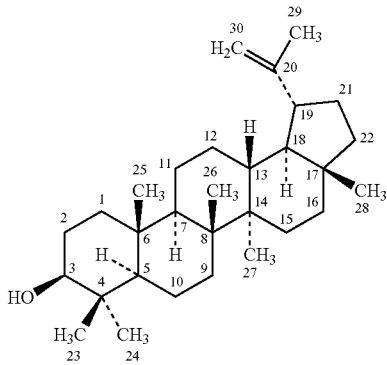

Lupeol

The invention will now be illustrated with by the following non-limiting Examples.

EXAMPLES

In the syntheses below, "DABCO" refers to 1,4-diazabicyclo[2.2.2]octane.

Example 1

Lup-20(29)-ene3,28-bis-(N-pyridiniumacetate) dichloride

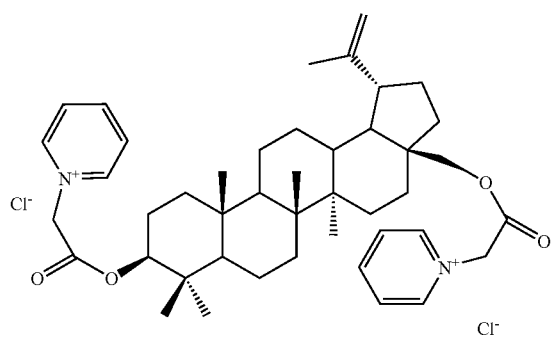

4.0 g (67.1 mmol) of betulin-3,28-dichloroacetate was dissolved in 20 ml of dry pyridine and the solution kept at 80° C. for 6 h. The mixture was placed then into benzene, the precipitate filtered, washed with the brine, and dried to yield 5.0 g (98.8%) of the product. NMR 1H (DMSO, TMS, 300 MHz): 9.18 (T, 2×2H, Pyr-H), 8.74 (T, 2×1H, Pyr-H) 8.27 (DD, 2×2H, Pyr-H), 5.80 (P, 4H, —CO—CH$_2$), 4.64 (D, 1H, 29-H), 4.53 (DD, 1-H, 3-H), 4.36 (D, 1H, 28-H), 3.91 (D, 1H, 3-H), 1.91 (M, 1H, 19-H), 1.65, 0.97, 0.95, 0.84, 0.79, 0.67 (all S, 6×3H, 30-, 27-, 26-, 25-, 24-, 23-Me), 1.01–1.64 (complex CH—, CH$_2$, 24H); NMR 13C (DMSO): 167.36, 166.58, 150.55, 147.65, 146.84,128.72, 110.88, 84.35, 65.24, 61.23, 55.46, 50.34, 48.98, 47.84, 46.74, 43.02, 41.17, 38.50, 38.25, 37.99, 37.27, 34.63, 29.77, 28.47, 27.34, 25.49, 23.82, 21.15, 19.53, 18.42, 16.88, 16.51, 16.37, 15.22 IR(KBr): 3426, 2944, 2872, 1742, 1631, 1272, 1222.

Example 2

Lup-20(29)-ene-3-[N-(4-oxybutyl)-1,4-diazabicyclo [2.2.2]octyl-N'-acetate]

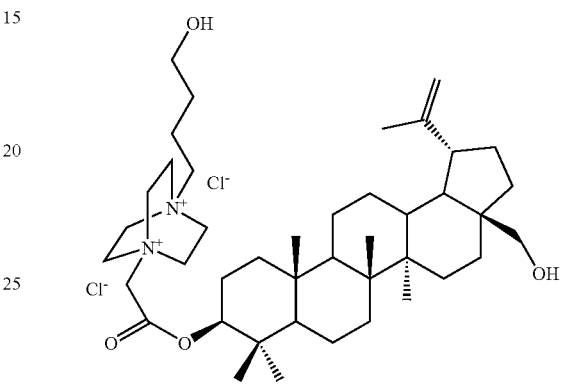

To 3.0 g of betulin-3-chloroacetate (5.85 mmol) in 100 ml of 1-butanol, 1.29 g (5.85 mmol) of N-(4-oxybutyl) DABCO chloride was added and the mixture was refluxed overnight. The solvent was evaporated until a viscous liquid formed. Dry toluene was added and mixed until a solid material appeared. The latter was filtered and dried to yield 4.03 g (93%) of the product. 1H NMR (DMSO, TMS): 3.28–4.53 (complex CH$_2$, 21H), 3.07 (D, 1H, 28-H), 0.83–1.87 (complex CH, CH$_2$, CH$_3$).

Example 3

Lup-20(29)-ene-3,28-bis[N-(1,4-diaza[2,2,2]bicycloocyl)acetate]dichloride

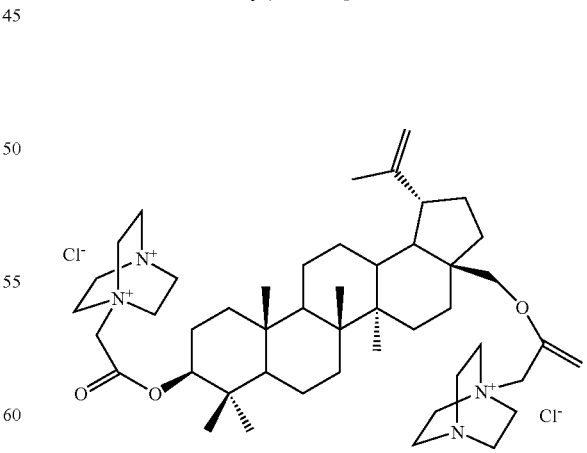

To a solution of 8.0 g (13.4 mmol) of betulin-3,28-dichloroacetate in 40 ml of dry dimethylformamide, 6.0 g (4×13.4 mmol) of DABCO (diazabicyclooctane) in 20 ml of DMFA was added at once. In a few minutes, a white precipitate was formed. The mixture was kept at room temperature for 24 hr. The precipitate filtered off, washed with DMPA then with dry benzene, and dried at 90° C. in vacuum. Yield 9.1 g (8.28%) IR (KBr) cm$^{-1}$.

1H NMR (DMSO, TMS) 4.72 (S, 1H, 29-H), 4.58 (S, 1H, 29-H), 4.47 (S, 2×2H, CH$_2$—CO), 4.42 (DD, 1H, 29-H), 3.92 (DD, 1H, 29-H), 3.51 (T, 12H, DABCO H), 3.08 (T, 12H, DABCO H), 1.93 (M, 1H, 19-H), 1.66, 1.01, 0.97, 0.84, 0.82 (all S, 5×3H, 27-, 26-, 25-, 24-, 23-Me), 1.09–1.45 (complex CH—, CH$_2$, 25H); 13C NMR (DMSO, TMS) 165.06, 164.53, 149.80, 110.22, 82.65, 63.59, 60.66, 54.40, 52.23, 49.42, 48.25, 46.99, 46.17, 44.52, 42.37, 37.64, 37.12, 36.62, 33.61, 29.16, 27.77, 26.68, 24.75, 23.33, 20.34, 18.86, 17.76, 16.43, 15.90, 15.69, 14.58.

Example 4

Lup-20(29)-ene-3,28-bis[N-(N'-benzyldiazabicyclo[2.2.2]octyl)acetate]tetrachloride

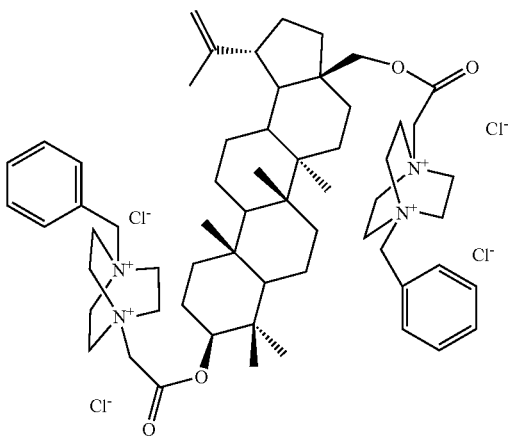

To a solution of 5.0 g (6.0 mmol) of betulin-3,28-bis[N-(diaza [2,2,2]bicycloocyl)acetate] in 70 ml of dry ethanol, 1.5 ml of benzylchloride was added and the solution was refluxed overnight. The resulting clear solution was evaporated in vacuum to 30 ml and then 100 ml of toluene added. A white precipitate was formed, then filtered, washed with toluene and dried in vacuum to yield 6.50 g of the product (99%).

IR(KBr):

1H NMR (DMSO, TMS) 7.16–7.57 (complex, 2×5H, Ph—H), 4.91 (S, 2×2H, PhCH$_2$), 3.53–4.79 (complex, 33H, 29-, 28-, COCH$_2$—, DABCO H), 1.65, 0.99, 0.96, 0.83, 0.82 (all S, 5×3H, 27-, 26-, 25-, 24-, 23-Me), 1.05–1.5 (complex CH—, CH$_2$, 25H); 13C NMR (DMSO, TMS) 164.58, 164.06, 133.22, 130.83, 129.32, 128.31, 125.42, 110.25, 83.12, 66.37, 64.02, 60.79, 54.36, 51.90, 51.43, 50.85, 49.91, 49.41, 48.26, 46.99, 46.16, 43.77, 42.38, 37.67, 37.13, 36.62, 33.96, 33.56, 29.11, 27.76, 26.70, 24.76, 23.35, 20.35, 18.86, 17.76, 16.40, 15.90, 15.69, 14.59.

Example 5

Lup-20(29)-ene-3,28-bis[N-(N'-(4-oxybutyl)diazabicyclo[2.2.2] octyl)acetate]tetrachloride

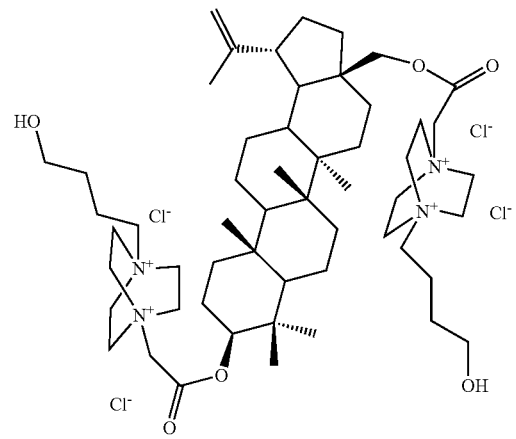

To a solution of 8.68 g (14.60 mmol) of betulin-3,28-bis(chloroacetate) in 120 ml of 1-butanol, 6.50 g (29.2 mmol) of N-(4-oxybutyl)diazabicyclo [2.2.2] octane was added. The mixture was refluxed for 24 hours. After that, the mixture was cooled down and evaporated in vacuum to yield 15.0 g (98.8%) of the product.

1H NMR (DMSO, TMS) 7.20 (M, 2×1H, OH), 3.21–5.15 (complex CH$_2$, CH), 0.83–1.95 (complex CH$_3$, CH$_2$, CH). 13C NMR (DMSO, TMS) 54.39, 51.39, 51.12$^-$, 50.41, 50.06, 49.44, 48.27, 46.99, 46.19, 44.19, 42.38, 37.70, 37.12, 36.63, 33.59, 28.96, 27.77, 26.69, 24.77, 23.36, 20.35, 18.87, 18.47, 18.24, 17.74, 16.41, 15.89, 15.70, 14.59.

Example 6

Lup-20(29)-ene-3-[N-(1,4-diazabicyclo[2.2.2]octyl)acetate]chloride

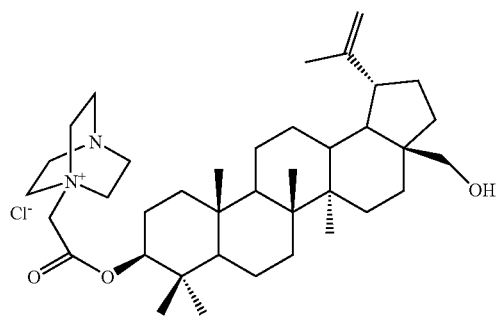

To a solution of 2.90 g (5.58 mmol) of betulin-3-chloroacetate in 20 ml of toluene, 1.25 g (5.58×2 mmol) of DABCO in 20 ml of toluene was added and the mixture was kept at 80° C. for 6 hr. The precipitate was filtered, washed with toluene and dried to yield 3.50 g (99%) of the product.

1H NMR (DMSO, TMS): 4.3–4.69 (complex CH, CH$_2$), 3.54 (T, 6H, DABCO CH$_2$), 3.11 (T, 6H, DABCO CH$_2$), 1.9 (M, 1H, 19-H), 0.85–1.67 (complex, CH, CH$_2$, CH$_3$).

Example 7

Lup-20(29)-ene-3,28-bis[(tetramethylethylenediamine-N-yl)acetate] dichloride

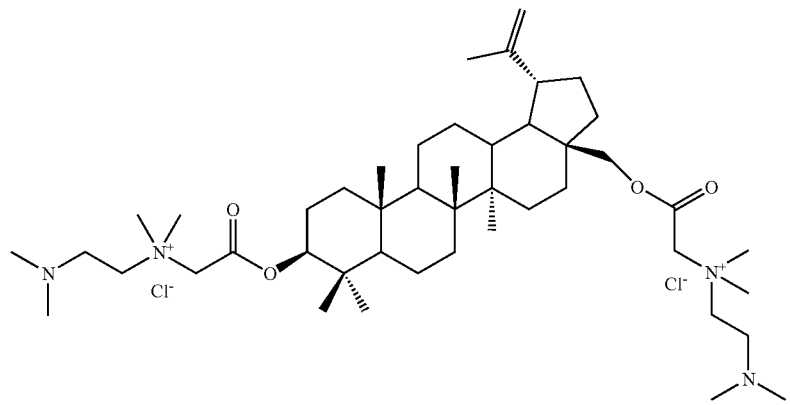

To a solution of 8.0 g (0.0134 mol) of betulin-3,28-bis(chloroacetate) in 40 ml of dry DMFA, 12 ml of tetramethylethylenediamine was added. The mixture was kept at room temperature overnight, then diluted with benzene, the precipitate filtered, washed with benzene and dried to yield 11.0 g (99%) of the product.

1H NMR (DMSO, TMS): 4.53–4.72 (complex $CH_2$, 4H), 4.35 (D, 1H, 28-H), 3.89 (D, 1H, 28-H), 2.5–3.65 (complex $NCH_2$, $NCH_3$), 0.82–1.66 (complex CH, $CH_2$, $CH_3$.

Example 8

Lup-20(29)-ene-3,28-bis[N'-benzyl-N,N,N',N'-tetramethylethylenediamine-N-yl)acetate] tetrachloride

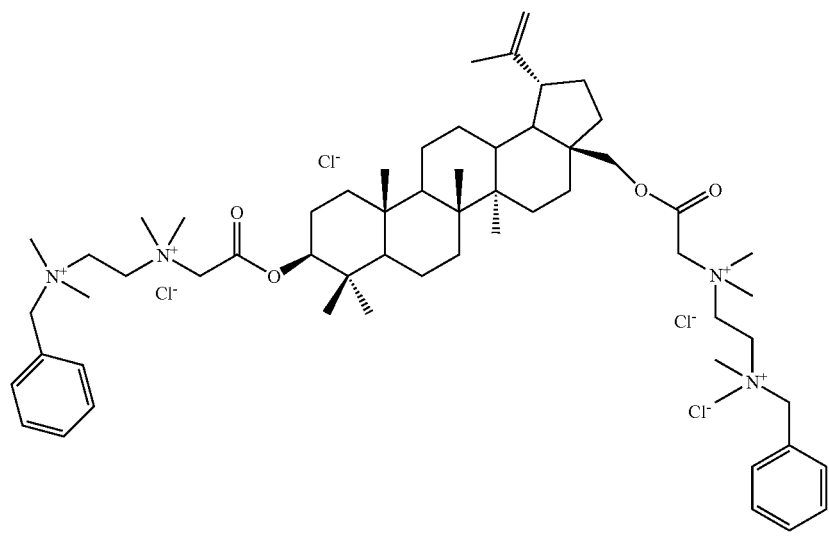

To a solution of 4.5 g (5.43 mmol) of Lup-20 (29)-ene-3,28-bis[(tetramethyltylenediamine-N-yl)acetate] dichloride (7) in 70 ml of ethanol 1.8 ml of benzylchloride was added and the solution was refluxed overnight, then evaporated in vacuum to yield 5.70 g (97.0%) of the product.

1H NMR (DMSO, TMS): 7.1–7.6 (complex benzene H), 2.51–4.85 (complex CH, CH$_2$, CH$_3$).

Example 9

Lup-20(29)-ene-3-[N-(N'-(benzyl)-diazabicyclo[2.2.2]octyl)acetate] dichloride

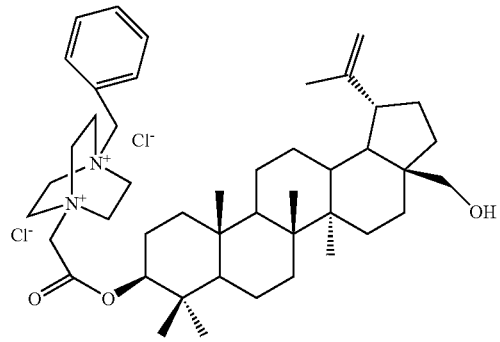

To a solution of 4.5 g (5.43 mmol) of Lup-20 (29)-ene-3-[(DABCO-N'-yl)acetate] chloride (6) in 70 ml of ethanol, 1.8 ml of benzylchloride was added and the solution was refluxed overnight, then evaporated in vacuum to yield 5.70 g (97.0%) of the product.

1H NMR (DMSO, TMS): 7.1–7.6 (complex benzene H), 2.51–4.85 (complex CH, CH$_2$, CH$_3$).

Example 10

N,N,N',N'-tetramethylethylenediamine-N,N'-bis-[lup-20(29)-ene-3-acetate]

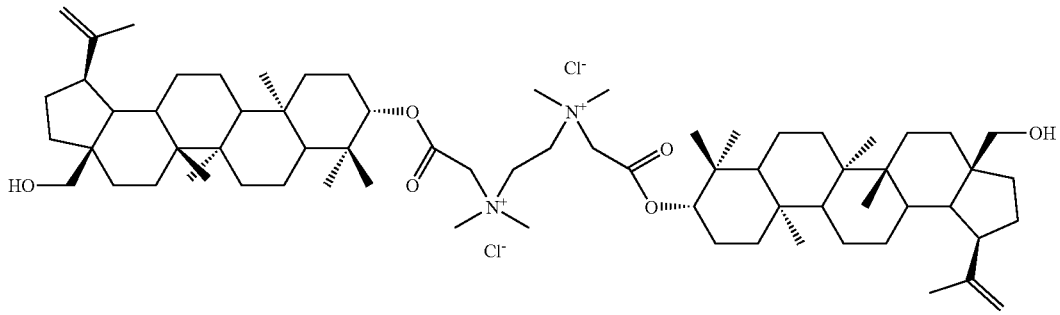

To a solution of 0.72 g (1.38 mmol) of betulin-3-chloroacetate in 10 ml of dry DMFA, 0.08 g (0.69 mmol) of tetramethylethylenediamine was added and the mixture was kept at 80° C. for 6 hr then the solvent evaporated in vacuum. The residue was washed with toluene and filtered to yield 0.23 g (28%) of the product.

1H NMR (DMSO, TMS): 4.29–4.66 (complex CH$_2$, CH), 3.09–3.68 (complex CH, CH$_3$, CH$_2$), 0.84–2.70 (complex CH, CH$_2$, CH$_3$).

Example 11

Bis(N,N'-pyridinium-2-ethyl)lup-20(29)-ene-3,28-dicarbamate dichloride

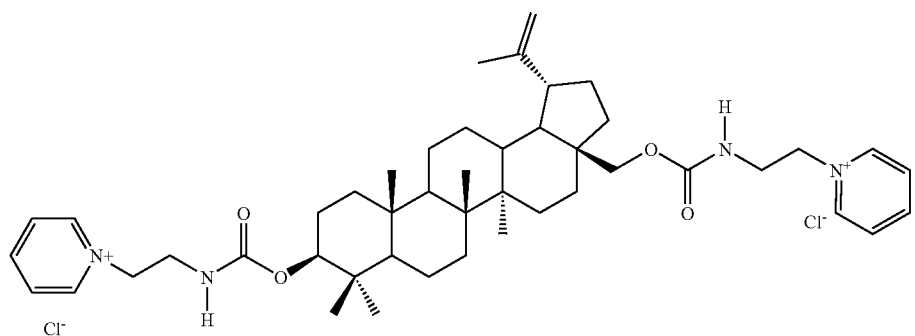

4.0 g (6.1 mmol) of lup-20 (29)-ene 3,28-di (ethyl) carbamate was dissolved in 5 mL of dry pyridine and the solution kept at 80° C. for 12 h. The mixture was then placed into benzene, the precipitate filtered, washed with the brine, and dried to yield 4.6 g (93%) of the product.

1HNMR (CDCl$_3$,d): 9.2 (m,4H), 8.6 (m,2H), 8.2 (m,4H), 7.5 (m,2H), 4.8 (m,5H), 4.6 (s,1H), 4.1 (m,2H), 3.6 (m,5H), 2.4 (m,1H), 2.0–0.7 (m,42H).

Example 12

1-(3,28-(diacetoxy)lup-20(29)-ene-30-yl)4-(dimethylamino)pyridinium bromide

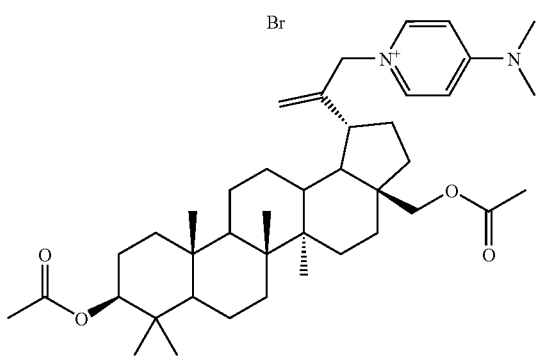

To a solution of 3,28-diacetyl-30-bromobetulin (1 g, 1.669 mmol) in 10 ml of toluene was added a solution of 4-(dimethylamino) pyridine (DMAP) (0.204 g, 1.669 mmol) in 10 ml of toluene under nitrogen atmosphere. The solution was heated overnight at 70° C. Then the solvent was evaporated and the residue was washed with hexane. The solids were dried to yield 1.18 g (97%) of the 1-(3,28-diacetoxylup-20-en-30-yl)-4-(dimethylamino) pyridinium bromide. M.p. 119–123° C. 1H NMR (CDCl$_3$, TMS): 0.76–1.90 (40H, m), 2.04 (3H, s), 2.06 (3H, s), 3.32 (6H, s), 3.73, 4.24 (2H, AB, J=11.1 Hz), 4.46 (1H, m), 4.64 (1H, s), 4.89, 5.03 (2H, AB, J=15.9 Hz), 5.09 (1H, s), 7.08 (2H, m), 8.32 (2H, m). 13C NMR (CDCl$_3$, TMS): 14.70, 15.93, 16.08, 16.40, 18.04, 20.82, 20.96, 21.25, 23.57, 26.82, 27.28, 27.85, 29.57, 31.44, 33.99, 34.17, 36.95, 37.23, 37.68, 38.31, 40.63, 40.79, 42.58, 43.25, 46.26, 50.02, 55.23, 62.11, 80.75, 108.22, 112.00, 125.19, 128.12, 128.93, 142.79, 149.15, 156.27, 170.91, 171.41,IR(KBr): 3414.17, 2941.70, 2872.27, 1728.88, 1647.69, 1568.23, 1447.32, 1367.09, 1240.59, 1167.30, 1030.57, 978.51, 839.85, 732.24, 514.70 Calcd: C,67.66, H, 8.72. Found: C, 66.50; H, 8.69.

Example 13

Lup-20(29)-ene-3,28-bis(N-pyridinium-2-propionate) dichloride

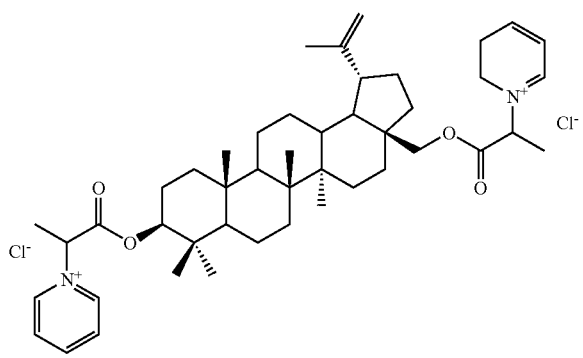

4.0 g (6.4 mmol) of lup-20(29)-ene-3,28-di (2'-chloropropionate) was dissolved in 5 mL of dry pyridine. The solution was kept at 80° C. for 12 h. The mixture was then placed into benzene, the precipitate filtered, washed with the brine, and dried to yield 4.6 g (92%) of the product.

Example 14

Lup-20 (29)-ene-3,28-bis (N-pyridinium-3-propionate) dichloride

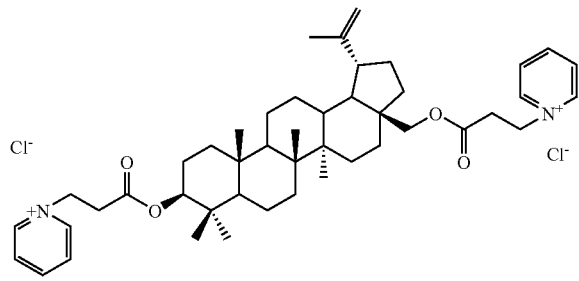

4.0 g (6.4 mmol) of lup-20 (29)-ene-3,28-di (3'-chloropropionate) was dissolved in 5 ml of dry pyridine. The solution kept at 80° C. for 12 h. The mixture was placed then into benzene, the precipitate filtered, washed with the brine, and dried to yield 4.6 g (92%) of the product.

Example 15
Lup-20 (29)-ene-3,28-bis(N-pyridinium4-butyrate) dichloride
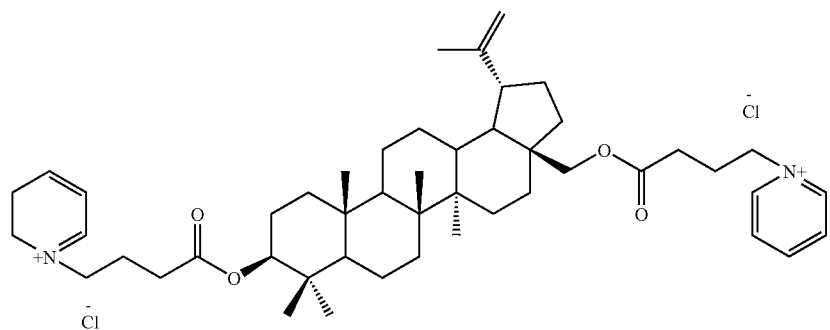
4.0 g (6.1 mmol) of lup-20(29)-ene-3, 28-di (2'-chlorobutyrate) was dissolved in 5 ml of dry pyridine. The solution kept at 80° C. for 12 h. The mixture was then placed into benzene, the precipitate filtered, washed with the brine, and dried to yield 4.5 g (90%) of the product.
Example 16
Lup-20(29)-ene-3,28-bis (N-pyridinium-4-butyrate) dibromide
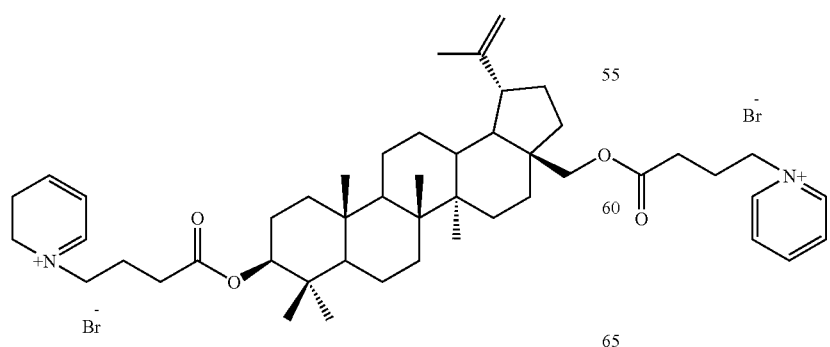

4.0 g (5.4 mmol) of lup-20(29)-ene-3,28-di (4'-bromobutyrate) was dissolved in 5 ml of dry pyridine. The solution was kept at 80° C. for 12 h. The mixture was placed then into benzene, the precipitate filtered, washed with brine, and dried to yield 4.3 g (89%) of the product.

Example 17

Lup-20(29)-ene 3,28-bis(N-pyridinium-2-butyrate) dibromide

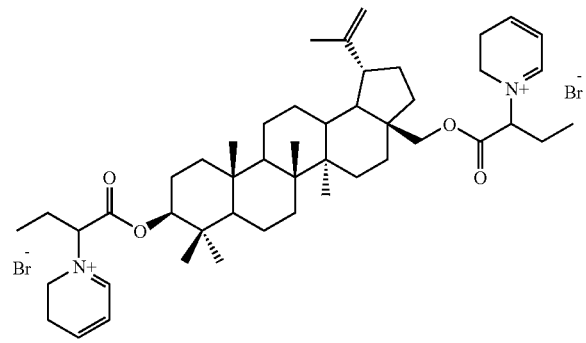

4.0 g (5.4 mmol) of lup-20(29)-ene-3,28-di (2'-bromobutyrate) was dissolved in 5 ml of dry pyridine. The solution was kept at 80° C. for 12 h. The mixture was placed then into benzene, the precipitate filtered, washed with brine, and dried to yield 4.3 g (89%) of the product.

Example 18

1-[3,28-(diacetoxy)lup-20(29)-ene-30-yl]-1,4-diazabicyclo[2.2.2]octane bromide

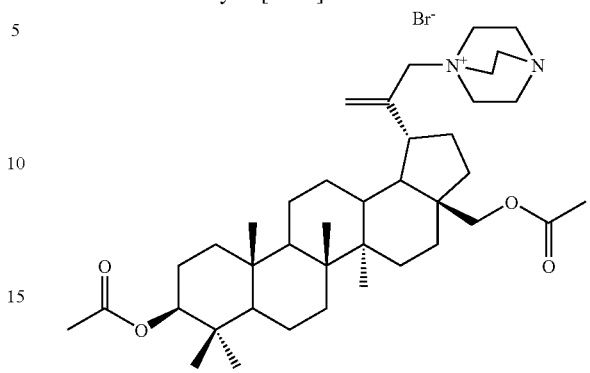

To a solution of 30-bromo-3,28-diacetylbetulin (21.9 g, 0.03616 mol) in dry toluene (100 ml) was added a solution of DABCO (12.2 g, 0.1085 mol) in dry toluene (250 ml) with stirring under nitrogen atmosphere. The mixture was refluxed for 3 hours. White solids were formed. The solids were filtered off and washed with toluene and hexane to give the pure product (20.2 g, 78%). M.p. 254–257° C. (dec.) 1H NMR (CDCl$_3$, TMS): 0.76–1.95 (39H, m), 3.26 (6H, m), 3.73 (7H, m), 4.17 (1H, d, J=13 Hz), 4.25 (1H, d, J=11 Hz), 4.47 (2H, m), 5.71 (2H, m). 13C NMR (CDCl$_3$, TMS): 14.51, 15.95, 16.10, 16.45, 18.08, 20.87, 21.01, 21.29, 23.63, 26.72, 27.88, 28.56, 29.62, 34.04, 34.47, 36.97, 37.72, 38.25, 40.79, 42.64, 45.52, 46.71, 49.90, 52.69, 55.22, 56.48, 62.01, 71.56, 80.73, 125.89, 144.03, 170.94, 171.33. IR (KBr): 3410.70, 2947.87, 1729.26, 1463.90, 1371.72, 1246.37, 1031.54, 979.26, 921.04, 846.02, 646.61 cm$^{-1}$. Calcd.: C, 66.93; H, 9.13. Found: C, 66.10; H, 9.51.

Example 19

3,28-bis[3-(1-piperidinyl)propanoyloxy]lup-20(29)-ene dihydrochloride

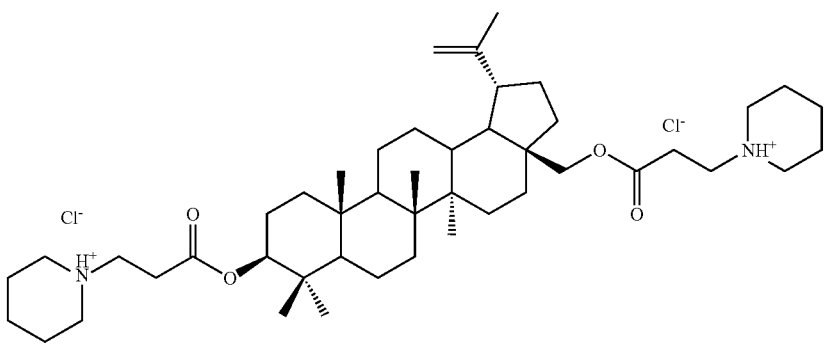

To a solution of 5.74 g (0.0104 mol) of 3,28-diacryloyl-betulin in 300 ml MeOH was added 4.44 g (0.0521 mol) of piperidine. The mixture was refluxed for 2 h. The solvent was evaporated and the product was dried in vacuum. Yield 7.51 g (100%). 1H NMR (free base) (CDCl$_3$, TMS): 0.76–2.00 (43H, m), 2.30–2.80 (1OH, m), 2.98 (2H, m), 3.85, 4.28 (2H, AB, J=1.0 Hz), 4.49 (1H, m), 4.554.70 (2H, m). 13C NMR (free base) CDCl$_3$, TMS): 14.67, 15.95, 16.07, 16.48, 18.09, 19.05, 23.62, 24.26, 24.67, 25.07, 25.90, 26.97, 27.85, 29.50, 29.69, 32.52, 32.82, 34.04, 34.50, 36.97, 37.48, 37.79, 38.29, 40.81, 42.61, 45.77, 46.35, 47.66, 48.70, 50.18, 54.17, 54.36, 54.40, 55.31, 62.57, 80.64, 109.79, 150.07, 172.45, 173.13.

This product was dissolved in 50 ml of aqueous HCl (1%), and the solution was evaporated to give 7.86 g of salt. M.p. 211–215° C. IR (hydrochloride) (KBr): 3420.73, 2957.51, 2637.19, 2539.99, 1727.91, 1454.84, 1391.01, 1198.93, 975.23, 881.70, 548.45, 445.47 cm$^{-1}$. Calcd.: C, 69.58; H, 9.90. Found: C, 68.97; H, 10.06.

Example 20

1-(3,28-dihydroxylup-20(29ene-30-yl)-4-(dimethylamino)pyridinium bromide

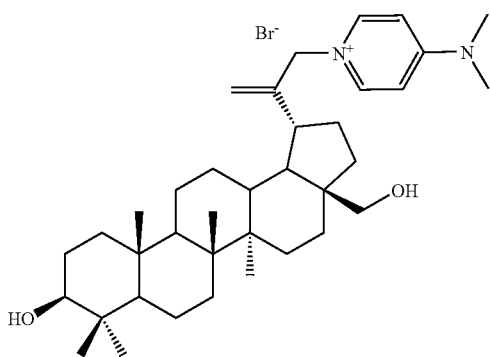

To a mixture of 30-bromobetulin (501 mg, 0.961 mmol) and 4-dimethylaminopyridine (117 mg, 0.961 mmol), ethanol (40 ml) and THF (10 ml) were added under nitrogen. The solution was refluxed for 3 h. The solvent was evaporated, and the solids were recrystallized from methanol/EtOAc (1:5) twice to yield 469 mg (76%) of the product. M.p. 220–223° C. 1H NMR (CD3OD, TMS): 0.69–2.38 (m, 40H), 3.12 (dd, J1=10.8 Hz, J2=5.4 Hz, 1H), 3.201–3.28 (m, 7H), 3.72 (d, J=11.1 Hz, 1H), 4.59 (s, 1H), 4.79 (s, 1H), 5.12 (s, 1H), 7.03, 8.11 (AB, J=7.8 Hz, 4H). 1H NMR (CDCl$_3$, TMS): 0.65–2.20 (m, 39H), 2.34 (m, 1H), 3.20 (m, 1H), 3.30 (s, 6H), 3.40, 3.68 (AB, J=9.6 Hz, 2H), 4.72 (s, 1H), 4.91 (s, 2H), 5.11 (s, 1H), 7.02 (m, 2H), 8.34 (m, 2H). 1H NMR (DMSO-d6, TMS): 0.60–1.76 (m, 36H), 1.85 (m, 3H), 2.31 (m, 1H), 3.01 (m, 2H), 3.50 (m, 1H), 4.67 (br s, 1H), 4.79 (dd, J1=17.6 Hz, J2=17.6 Hz, 2H), 5.01 (s, 1H), 7.06 (d, J=7.4 Hz, 2H), 8.23 (d, J=7.4 Hz, 2H). 13C NMR (DMSO-d6, TMS): 13.98, 14.46, 15.59, 15.72, 15.80, 17.85, 20.42, 20.66, 26.36, 26.49, 27.06, 27.99, 30.95, 33.34, 33.69, 36.49, 36.57, 42.09, 47.22, 49.23, 49.62, 54.74, 57.53, 59.64, 76.67, 107.51, 110.29, 142.46, 142.54, 150.95, 155.79, 170.21, IR (KBr): 3362.11, 2932.25, 2866.10, 1648.07, 1567.85, 1445.78, 1400.65, 1237.11, 1168.27, 1036.94, 819.02, 517.41 cm$^{-1}$. Calcd.: C, 69.03; H, 9.24; Br, 12.41.

Example 21

Lup-20(29)-ene-3,28-bis[N-(4-dimethylaminopyridinium)-2-propionate]dichloride

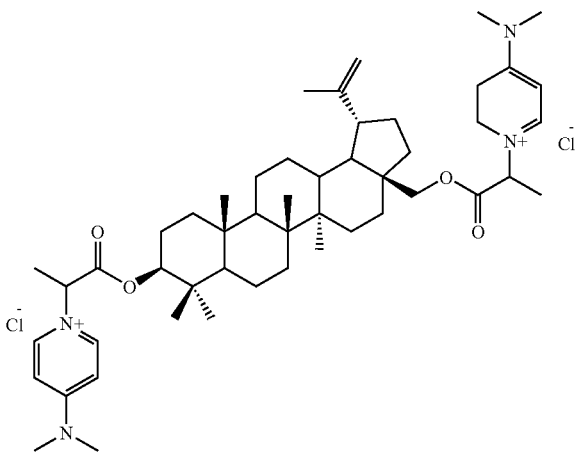

To a solution of 1.76 g (2.8 mmol) of betulin-3,28-di(2'-chloropropionate) in 10 ml of dimethylacetamide, 1.38 g (4×2.8 mmol) of 4-(dimethylamino)pyridine (DMAP) in 10 ml of dimethylacetamide was added at once. The mixture was kept at room temperature for 24 hr. Then ether was added, the precipitate filtered off, washed with ether, and dried at 90° C. in vacuum. Yield 2 g (82%) 1H NMR (CDCl$_3$, d): 8.6 (m, 3H), 7.0 (m, 3H), 6.0–5.8 (m, 2H), 4.7 (s, 1H), 4.6 (s, 1H), 4.5–4.3 (m, 2H), 4.1–3.8 (m, 1H), 3.4 (s, 12H), 2.4 (m, 1H), 2.2–0.7 (m, 50H) 13C NMR (CDCl$_3$, d): 169.6, 168.9, 156.5, 149.5, 142.0, 116.2, 109.9, 107.8, 84.0, 83.3, 70.4, 64.9, 63.9, 63.7, 60.0, 55.1, 52.6, 50.0, 58.6, 47.4, 46.3, 42.5, 40.7, 40.4, 37.8, 37.7, 37.4, 36.8, 35.0, 34.2, 33.8, 29.2, 28.0, 26.8, 24.9, 23.3, 21.4, 20.5, 18.9, 18.2, 17.9, 16.3, 15.9, 14.5.

Example 22

Lup-20(29)-ene-3,28-bis[N-(1,4-diazabicyclo [2.2.2] octyl)-2-propionate]-dichloride

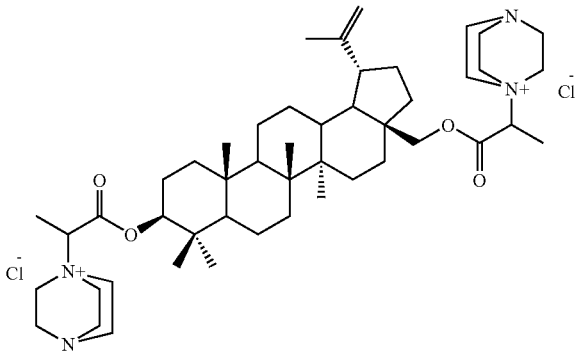

To a solution of 1.61 g (2.6 mmol) of betulin-3,28-di (2'-chloropropionate) in 10 ml of dimethylacetamide, 1.16 g (4×2.6 mmol) of DABCO in 20 ml of dimethylacetamide was added at once. The mixture was kept at room temperature for 24 hr. Then ether was added, the precipitate filtered off, washed with ether and dried at 90° C. in vacuum. Yield 1.75 g (80%).

1H NMR (DMSO, d): 4.9 (s, 1H), 4.8 (s, 1H), 4.7 (m, 1H), 4.6 (d, 1H), 4.2 (d, 1H), 3.7 (m, 6H), 3.6 (m, 12H), 2.6 (m, 1H), 2.0–0.9 (m, 50H).

Example 23

1-(lup20(29)-ene-30-yl)-1,4-diazabicyclo[2.2.2]octane bromide

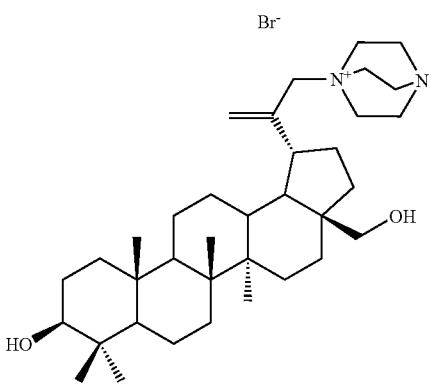

A mixture of 30-bromobetulin (503 mg, 0.964 mmol) and 1,4-diazabicyclo[2.2.2]octane (130 mg, 1.16 mmol) in methanol (25 ml) was refluxed for 3 hours under nitrogen. The solvent was evaporated; THF was added, and solids were filtered off and washed with THF. The solids were recrystallized from isopropanol to yield 310 mg (51%) of the product. M.p. 317–319° C. (dec.) 1H NMR (DMSO-d6, TMS): 0.60–1.76 (m, 34H), 1.91 (m, 2H), 2.21 (m, 3H), 2.95–3.45 (m, 14H), 3.51 (m, 1H), 3.94 (dd, J1=35.4 Hz, J2=12.3 Hz, 2H), 5.40 (s, 1H), 5.62 (s, 1H). 13C NMR (DMSO-d6, TMS): 14.22, 15.54, 15.71, 15.77, 17.86, 20.50, 26.47, 27.55, 27.97, 28.64, 28.67, 33.40, 33.71, 34.07, 36.27, 36.53, 38.10, 38.37, 42.07, 44.63, 47.54, 49.39, 51.75, 54.65, 56.52, 57.66, 70.54, 76.60, 108.23, 124.02, 145.42, IR (KBr): 3373.68, 2925.50, 2862.63, 1466.02, 1374.62, 1040.99, 844.28, 797.61, 651.44 cm$^{-1}$. Calcd.: C, 68.22; H, 9.70; Br, 12.61. Found: C, 67.87; H, 9.74; Br, 12.51.

Example 24

1-(3,28-dihydroxylup-20(29)ene-30-yl)pyridinium bromide

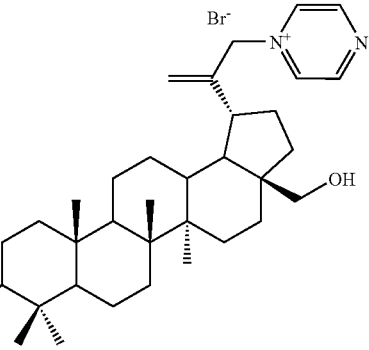

30-bromobetulin (505 mg, 0.968 mmol) was dissolved in pyridine (2.5 ml, 30.9 mmol) under nitrogen. The mixture was kept at 80° C. for 2 hours. Benzene was added; solids were filtered off and recrystallized from MeCN to yield 395 mg (68%) of product. M.p. 280–282° C. 1H NMR (CD3OD, TMS): 0.68–2.06 (m, 39H), 2.34 (m, 1H), 3.12 (dd, J1=10.8 Hz, J2=5.1 Hz, 1H), 3.24, 3.72 (AB, J=11.3 Hz, 2H), 4.65 (s, 1H), 5.24 (s, 1H), 5.29 (dd, J1=15.9 Hz, J2=15.9 Hz, 2H), 8.18 (m, 2H), 8.67 (m, 1H), 9.01 (m, 2H). 13C NMR (CD3OD, TMS): 15.20, 16.16, 16.55, 16.71, 19.46, 22.11, 28.07, 28.16, 28.64, 30.35, 32.71, 34.84, 35.47, 38.30, 38.50, 39.98, 40.10, 42.17, 43.84, 43.93, 45.09, 51.59, 51.70, 56.80, 60.08, 66.91, 66.93, 66.95, 79.61, 113.65, 129.66, 146.74, 147.59, 151.42. IR (KBr): 3382.74, 2936.88, 2867.64, 1629.37, 1481.26, 1388.89, 1150.53, 1040.80, 769.46, 689.04. Calcd.: C, 69.98; H, 9.06; Br, 13.30. Found: C, 69.90; H, 8.95; Br, 13.50.

Example 25

Lup-20(29)-ene-3,28-bis[(N-(1,4-diazabicyclo[2.2.2]octyl)4-butyrate)]dibromide

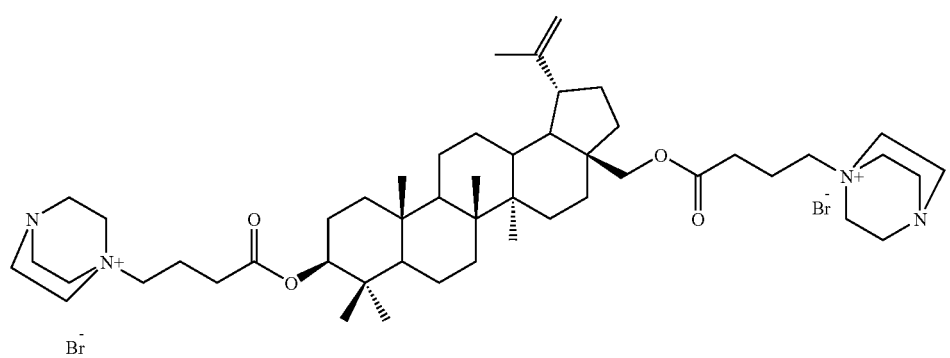

To a solution of 1.5 g (2.0 mmol) lup-20(29)-ene-3,28-di(4'-bromobutyrate) in 10 ml of dimethylacetamide, 0.9 g (4×2.0 mmol) of DABCO in 5 ml of dimethylacetamide was added at once. The mixture was kept at room temperature for 24 hr. Then ether was added, the precipitate filtered off, washed with ether and dried at 90° C. in vacuum. Yield 1.73 g (78%).

1H NMR (DMSO, d): 4.75 (s, 1H), 4.6 (s, 1H), 4.5 (m, 1H), 4.35 (d, 1H), 3.8 (d, 1H), 3.5–3.0 (m, 30H), 2.5 (m, 7H), 2.0–0.9 (m, 42H).

Example 26

Lup-20(29)-ene-3,28-bis[N-(1,4-diazabicyclo[2.2.2]octyl)4-butyrate]dichloride

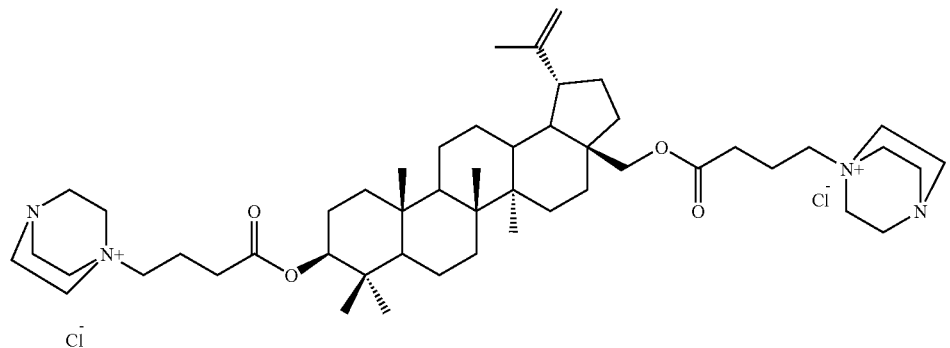

To a solution of 1.5 g (2.3 mmol) lup-20(29)-ene-3,28-di(4-chlorobutyrate) in 10 ml of dimethylacetamide, 1.03 g (4×2.3 mmol) of DABCO in 5 ml of dimethylacetamide was added at once. The mixture was kept at room temperature for 24 hr. Then ether was added, the precipitate filtered off, washed with ether and dried at 90° C. in vacuum. Yield 1.75 g (87%).

1H NMR (DMSO, d): 4.75 (s, 1H), 4.6 (s, 1H), 4.5 (m, 1H), 4.35 (d, 1H), 3.8 (d, 1H), 3.5–3.0 (m, 30H), 2.5 (m, 7H), 2.0–0.9 (m, 42H).

Example 27

1-(3,28-dihydroxylup-20(29)-ene-30-yl)-[N-3-(hydroxymethyl)pyridinium]bromide

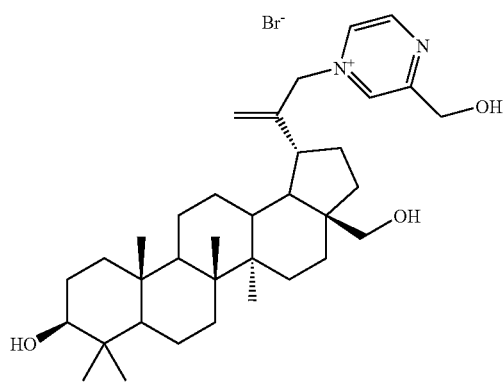

A mixture of 30-bromobetulin (1 g, 1.917 mmol) and 3-hydroxymethylpyridine (418 mg, 3.83 mmol) in IBF (10 ml) was refluxed for 17 hours under nitrogen. The solids were filtered off, washed with THF, and recrystallized from MeCN to yield 719 g (59%) of product. M.p. 244–247° C. 1H NMR (CD3OC, TMS): 0.70–2.10 (m, 39H), 2.40 (m, 11H), 3.14 (dd, J1=10.8 Hz, J2 =5.1 Hz, 11H), 3.23, 3.72 (AB, J=11.0 Hz, 2H), 2.40 (m, 1H), 5.24–5.36 (m, 3H), 8.12 (m, 1H), 8.59 (m, 1H), 8.88 (m, 1H), 8.93 (br s, 1H). 13C NMR (CD3OD, TMS): 15.19, 16.16, 16.55, 16.71, 19.46, 22.13, 28.07, 28.64, 28.71, 30.35, 32.70, 34.85, 35.49, 38.31, 38.52, 39.99, 40.10, 42.19, 43.86, 45.08, 51.59, 51.76, 56.81, 60.10, 61.07, 66.95, 79.65, 113.75, 129.06, 144.16, 145.08, 145.65, 151.35, IR (KBr): 3356.51, 2938.61, 2866.68, 1458.89, 1390.04, 1032.70, 987.38, 921.04, 688.27, 545.37 cm$^{-1}$. Calcd.: C, 68.55; H, 8.95; Br, 12.67. Found: C, 66.65; H, 8.76; Br, 12.48.

Example 28

1-(3,28-dihydroxylup-20(29)ene-30-yl)(N-3,5-dimethylpyridinium) bromide

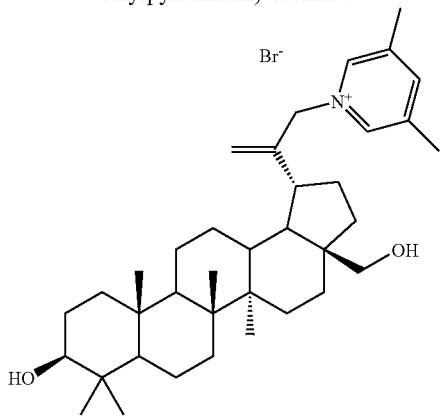

A mixture of 30-bromobetulin (1.004 g, 1.925 mmol) and 3,5-dimethylpyridine (412 mg, 3.85 mmol) in THF (10 ml) and MeOH (5 ml) was refluxed for 20 hours under nitrogen. The solvent was evaporated, and the solids were recrystallized from MeCN to give 993 mg (82%) of the product. M.p. 293–296° C. 1H NMR (CD3OD, TMS): 0.68–2.10 (m, 39H), 2.38 (m, 1H), 2.55 (s, 6H), 3.12 (dd, J1=10.8 Hz, J2 =5.4Hz, 1H), 3.24, 3.72 (AB, J=11.4 Hz, 2H), 4.66 (s, 1H), 5.16 (m, 2H), 5.22 (s, 1H), 8.33 (s, 1H), 8.67 (s, 2H). 13C NMR (CD3OD, TMS): 15.19, 16.15, 16.54, 16.71, 16.75, 18.25, 19.44, 19.47, 22.14, 28.04, 28.08, 28.64, 30.37, 30.39, 32.70, 32.71, 34.87, 35.47, 38.31, 38.50, 39.99, 40.11, 40.13, 42.18, 43.84, 45.01, 51.42, 51.44, 51.73, 56.81, 60.11, 79.63, 113.57, 140.66, 143.43, 148.50, 151.14, IR (KBr): 3327.10, 3075.15, 2930.51, 2867.45, 1631.10, 1453.10, 1388.50, 1308.28, 1036.94, 930.10, 659.92, 559.64 cm$^{-1}$. Calcd.: C, 70.68; H, 9.30; Br, 12.71. Found: C, 70.47; H, 9.29; Br, 12.48.

Example 29

Bis[N-(1,4-diazabicyclo[2.2.2]octyl)-2-ethyl]-lup-20(29)-ene-3,28-dicarbamate dichloride

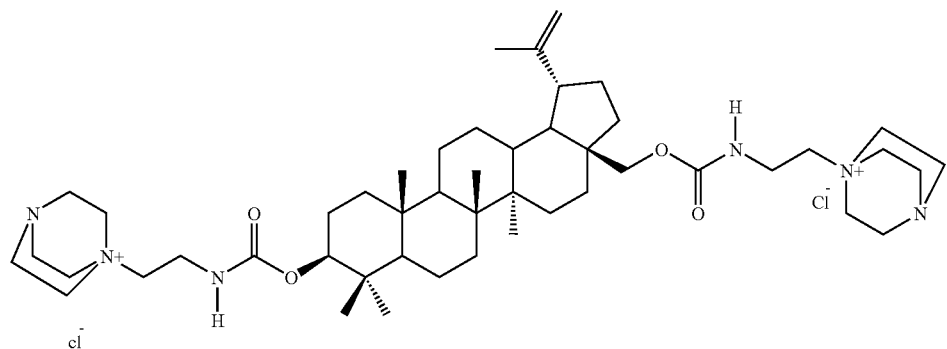

To a solution of 0.75 g (1.15 mmol) lup-20(29)-ene 3,28-di-ethylcarbamate in 10 ml of dimethylacetamide, 0.51 g (4×1.15 mmol) of DABCO in 5 ml of dimethylacetamide was added at once. The mixture was kept at boiling temperature for 24 hr. Then ether was added, the precipitate filtered off, washed with ether and dried at 90° C. in vacuum. Yield 0.75 g (56%) 1H NMR (DMSO, TMS, d): 4.8 (s, 1H), 4.6 (s, 1H), 4.4–4.0 (m, 5H), 3.9–3.1 (m, 32H), 2.6 (m, 1H), 2.0–0.9 (m, 42H).

Example 30

Lup-20(29)-ene-3,28-bis[N-(3-oxymethylpyridinium)acetate) dichloride 3 g of betulin-3,28-di(chloroacetate) (0.005 mol) was dissolved in 7 ml of 1-methyl-2-pyrrolidinone, and 2.2 g of 3-pyridylcarbinol (0.02 mol) was added. The reaction mixture was heated up to 70° C. for 20 hours. Reaction was monitored by TLC analysis. The reaction mixture then was diluted with THF and filtrated. The precipitate was washed with THF and dried with an oil pump. Yield 3.55 g.

Example 31

Lup-20 (29)ene-3,28-bis[N-(2-oxymethylpyridinium)acetate]dichloride

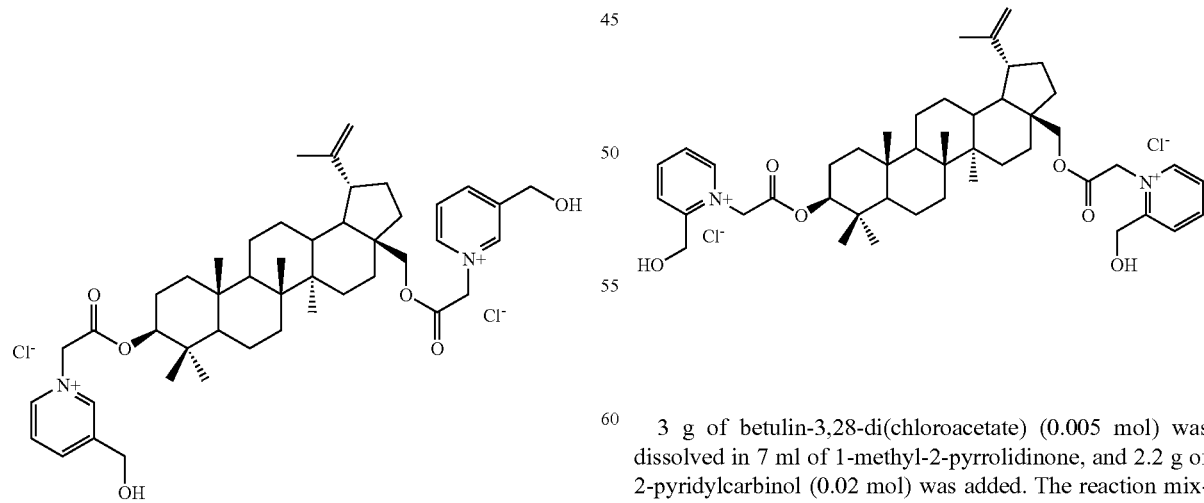

3 g of betulin-3,28-di(chloroacetate) (0.005 mol) was dissolved in 7 ml of 1-methyl-2-pyrrolidinone, and 2.2 g of 2-pyridylcarbinol (0.02 mol) was added. The reaction mixture was heated up to 70° C. for 20 hours. Reaction was monitored by TLC analysis. The reaction mixture then was diluted with THE and filtrated. The precipitate was washed with THF and dried on oil pump. Yield 1.75 g.

Example 32

Lup-20 (29)-ene-3,28-bis
[N-(2-methylureapyridinium)acetate]dichloride

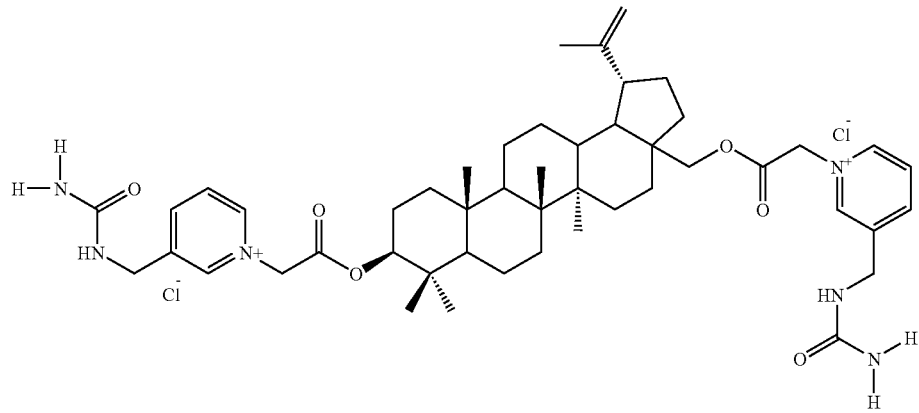

5 g of betulin-3,28-di(chloroacetate) (0.008 mol) was dissolved in 35 ml of 1-methyl-2-pyrrolidinone, and 4 g of 1-(3-pyridylmethyl)urea (0.0265 mol) was added. The reaction mixture was heated up to 70° C. for 20 hours. Reaction was monitored by TLC analysis. The reaction mixture then was diluted with THF and filtrated. The precipitate was washed with TBF and dried with an oil pump. Yield 5.8 g (85%).

Example 33

Lup-20 (29)-ene-3-[N-(2-oxymethylpyridinium)acetate] chloride

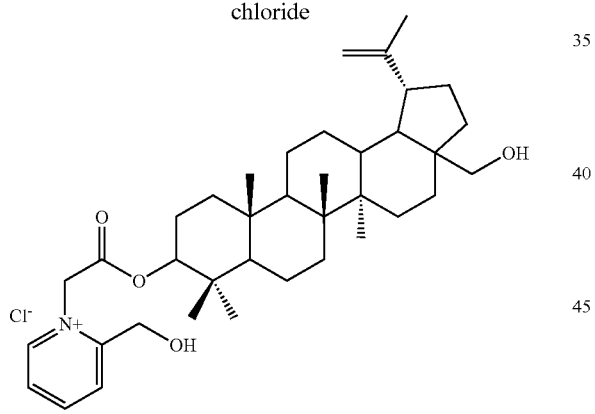

3 g of betulin-3-(chloroacetate) (0.006 mol) was dissolved in 15 ml of 1-methyl-2-pyrrolidinone, and 2.56 g of 2-pyridylcarbinol (0.024 mol) was added. The reaction mixture was heated up to 70° C. for 20 hours. Reaction was monitored by TLC analysis. The reaction mixture then was diluted with THF and filtered. Precipitate was washed with CHCl₃ and dried with an oil pump. Yield 1.66 g.

Example 34

Lup-20(29)ene-3,28bis[N-(N-methylmorpholino)acetate] dichloride

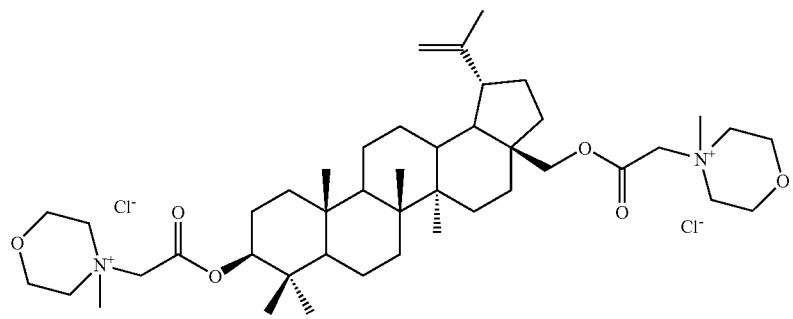

3 g of betulin-3,28-bis-(chloroacetate) dichloride (0.005 mol) was dissolved in 15 ml of 1-methyl-2-pyrrolidinone, and 2.02 g of 4-methylmorpholine (0.024 mol) was added. The reaction mixture was heated up to 70° C. for 12.0 hours. Reaction was monitored by TLC analysis. The reaction mixture then was diluted with THF and filtered. The precipitate was washed with CHCl₃ and dried with an oil pump. Yield 2.95 g.

Example 35

Lup-20(29)ene-3,28bis[(4-hydroxyl-N-methylpiperi-dino)acetate] dichloride 3 g of betulin-3-chloroacetate (0.006 mol) was dissolved in 15 ml of 1-methyl-2-pyrrolidinone, and 1.8 g of 1-(3-pyridylmethyl)urea (0.012 mol) was added. The reaction mixture was heated up to 70° C. for 20 hours. Reaction was monitored by TLC analysis. The reaction mixture then was diluted with THF and filtered. The precipitate was washed with CHCl₃ and benzene and dried with an oil pump. Yield 2 g.

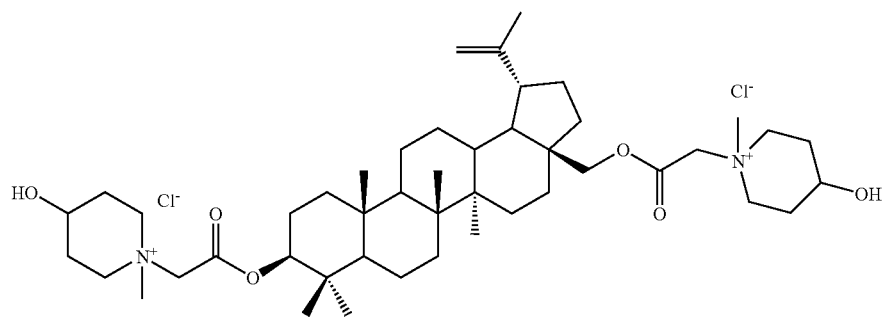

3 g of betulin-3,28-bis(chloroacetate) dichloride (0.005 mol) was dissolved in 15 ml of 1-methyl-2-pyrrolidinone, and 4.6 g of 4-hydroxy-1-methylpipieridine (0.04 mol) was added. The reaction mixture was heated up to 70° C. for 20 hours. Reaction was monitored by TLC analysis. The reaction mixture then was diluted with THF and filtered. The precipitate was washed with CHCl₃ and dried with an oil pump. Yield is 2.01 g.

Example 36

Lup-20(29)-ene-3-[N-(3-(ureamethyl)pyridinium) acetate] chloride

Example 37

Lup-20(29)-ene-3-(N-pyridiniumacetate) chloride

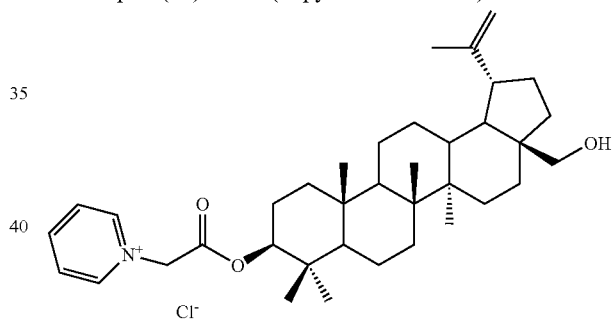

8 g of betulin-3-(chloroacetate) were dissolved in 50 ml of pyridine and heated up to 70° C. for 3 hours. The precipitate was filtered and washed with THF and then with benzene twice, and dried with an oil pump. Yield is 7.5 g.

Example 38

Lup-20(29)-ene-3,28-bis[N-(1,4diazabicyclo[2.2.2] octyl)-2-butyrate] dibromide

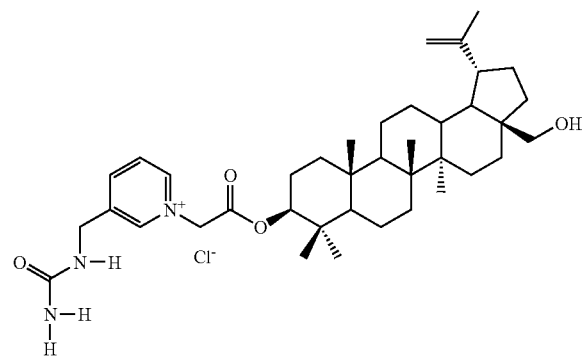

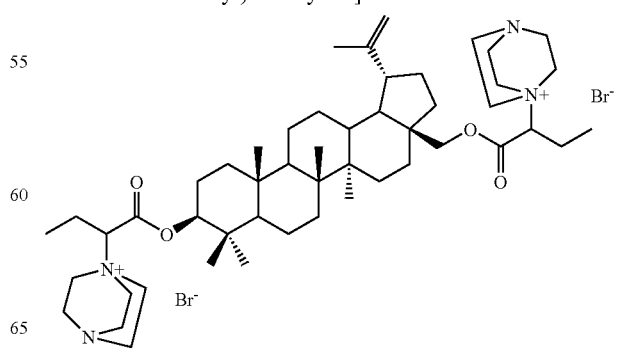

To a solution of 1.5 g (2.0 mmol) lup-20 (29)-ene-3,28-di (2'-bromobutyrate) in 10 ml of dimethylacetamide, 0.9 g (4×2.0 mmol) of DABCO in 5 ml of dimethylacetamide was added at once. The mixture was kept at room temperature for 24 hr. Then ether was added, the precipitate filtered off, washed with ether, and dried at 90° C. in vacuum. Yield 1.84 g (94%). 1H NMR (CD3OD, d): 8.0 (m 2H), 4.9–4.7 (dd, 2H), 4.6 (m, 2H), 4.2 (m, 2H), 3.8 (m, 4H), 3.5 (m, 5H), 3.2 (m, 10H), 2.5 (m, 1H), 2.3 (m, 2H), 2.0–0.7 (m, 42H).

Example 39

Lup-20(29)-ene-3,28-bis[N-(4dimethylaminopyridinium)-2-butyrate] dibromide

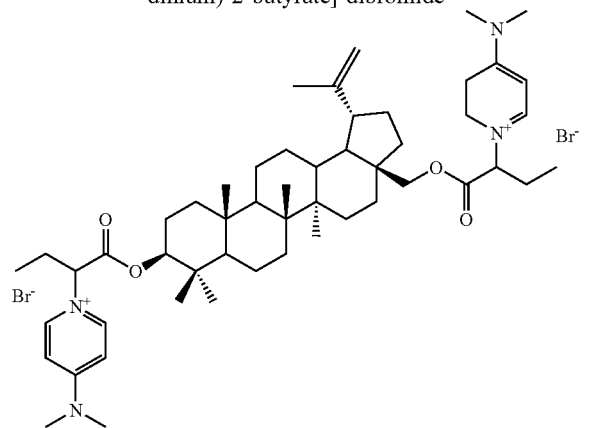

To a solution of 4 g (5.4 mmol) of betulin-3,28-di(2'-bromobutyrate) in 10 ml of benzene, 2.7 g (4×5.4 mmol) of 4-(dimethylamino)pyridine (DMAP) in 10 ml of benzene was added at once. The mixture was kept at room temperature for 24 hr. Then ether was added, the precipitate filtered off, washed with ether and dried at 90° C. in vacuum. Yield is 4.8 g (90%) 1H NMR (DMSO, d): 8.4 (m, 4H), 7.1 (m, 4H), 5.4 (m, 2H), 4.7–4.5 (dd, 2H), 4.5–4.2 (m, 2H), 3.8 (m, 1H), 3.4 (m, 4H), 3.2 (m, 12H), 2.4 (m, 5H), 2.0–0.7 (m, 4H+2H).

Example 40

Lup-20(29)-ene3,28-bis[N-(4-dimethylaminopyridinium)4-butyrate] dibromide

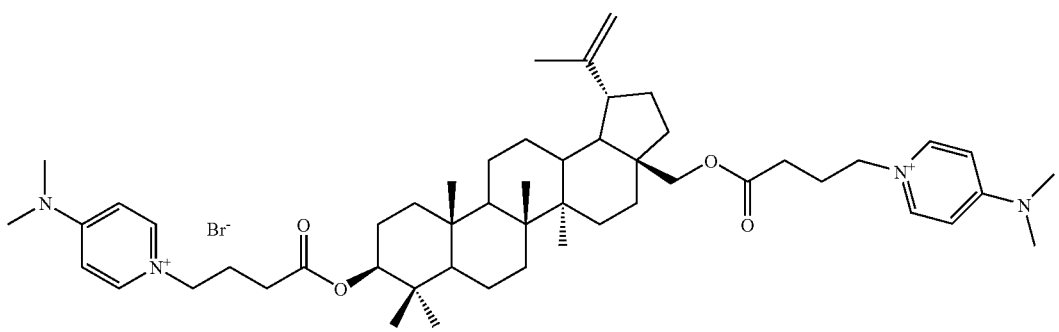

To a solution of 3 g (4.1 mmol) of betulin-3,28-di (4'-bromobutyrate) in 10 ml of benzene, 2 g (4×4.1 mmol) of 4-(dimethylamino) pyridine (DMAP) in 10 ml of benzene was added at once. The mixture was kept at room temperature for 24 hr. Then ether was added, the precipitate filtered off, washed with ether and dried at 90° C. in vacuum. Yield 3.7 g (93%) 1H NMR (DMSO, d): 8.4 (m, 4H), 7.1 (m, 4H), 4.7–4.5 (dd, 2H), 4.4 (m, 1H), 4.2 (m, 5H), 3.8 (d, 1H), 3.2 (m, 12H), 2.4 (m, 5H), 2.1 (m, 4H), 2.0–0.7 (m, 42H).

Example 41

Lup-20(29)-ene-3,28-bis[N-(4-dimethylaminopyridinium)-3-propionate] dichloride

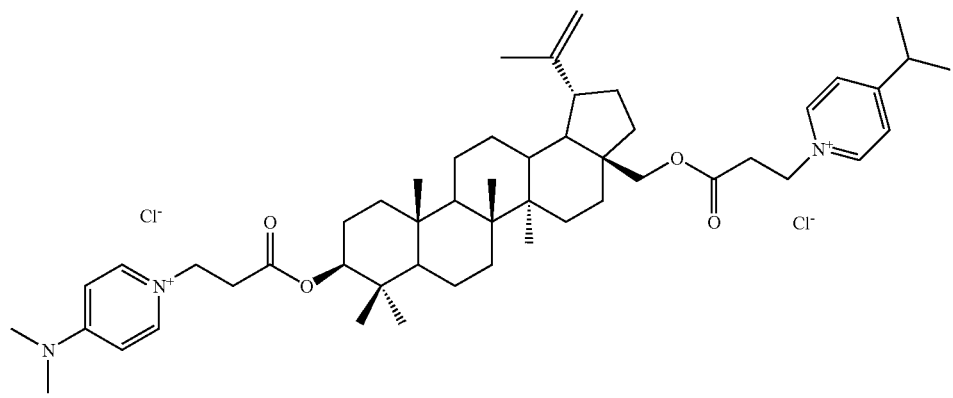

To a solution of 4 g (6.1 mmol) of betulin-3,28-di(3'-chloropropionate) in 10 ml of benzene 3 g (4×6.1 mmol) of 4-(dimethylamino) pyridine (DMAP) in 10 ml of benzene was added at once. The mixture was kept at room temperature for 24 hr. Then the ether was added, the precipitate filtered off, washed with ether and dried at 90° C. in vacuum. Yield 4.3 g (77%).

1H NMR (DMSO, d): 8.4 (m, 4H), 7.1 (m,4H), 4.74.5 (dd,2H), 4.4 (m, 4H), 4.3 (m, 1H), 3.8 (d, 1H), 3.5 (d, 1H), 3.2 (m, 12H), 3.1 (m, 4H), 2.4 (m, 1H), 2.2–0.7 (m, 42M).

Example 42

1-(3,28-dihydroxylup-20(29)-ene-30-yl)4-(hydroxymethyl)pyridinium bromide

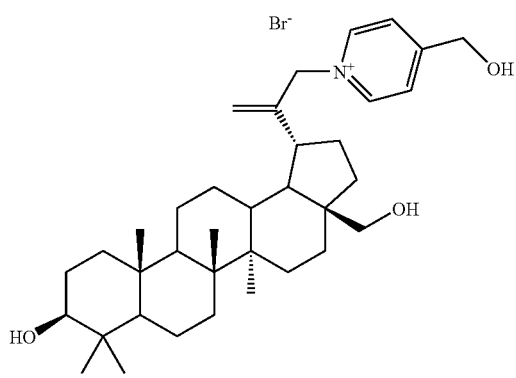

A mixture of 30-bromobetulin (0.23 g, 0.441 mmol) and 4-pyridinemethanol (200 mg, 1.83 mmol) in MeOH (10 ml) was refluxed for 17 hours under nitrogen. The solution was evaporated to a small volume and poured into ether (40 ml) to yield a precipitate.

Example 43

1-(3,28-dihydroxylup-20(29)-ene-30-yl)-3-hydroxy-1-azabicyclo[2.2.2] octane bromide

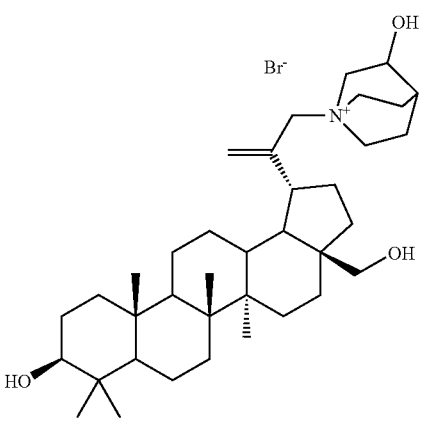

A mixture of 30-Bromobetulin (498 mg, 0.9547 mmol) and 3-quinuclidinol (121.4 mg, 0.9547 mmol) in MeOH (10 ml) was refluxed for 16 hours under nitrogen. The solvent was evaporated, and the residue was recrystallized from EtOAc/MeOH to give 398.8 mg (64%) of product. M.p. 308–310° C. 1H NMR (CD3OD, TMS): 0.68–2.40 (45H, m), 3.11 (1H, dd, J1=10.4 Hz, J2=5.3 Hz), 3.23, 3.72 (2H, AB, J=10.8 Hz), 3.33–3.56 (6H, m), 3.80–3.95 (2H, m), 4.20 (1H, m), 5.46 (1H, m), 5.70 (1H, d, J=6 Hz). 13C NMR (CD3OD, TMS): 9.07, 10.23, 10.60, 10.77, 13.04, 13.54, 16.25, 16.67, 22.11, 22.28, 22.71, 23.95, 24.41, 29.19, 29.57, 29.80, 32.37, 32.43, 34.06, 34.14, 36.21, 37.90, 41.02, 45.65, 49.40, 49.72, 50.12, 50.30, 50.86, 52.57, 52.90, 54.36, 58.83, 59.57, 67.04, 73.69, 119.56, 119.76, 141.16, 141.39. IR (KBr): 3219.96, 2941.50, 2866.29, 1459.85, 1377.12, 1037.13, 920.27. Calcd: C, 68.50; H, 9.63. Found: C, 65.04; H, 9.23.

Example 44

Lup-20(29)ene-3,28-bis[N-(2,4-dimethylpyridinium) acetate] dichloride

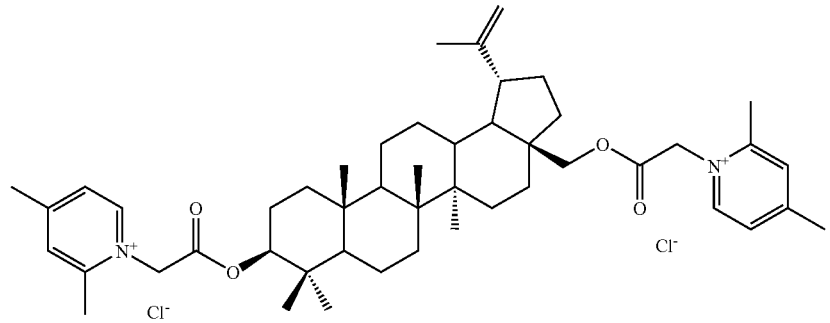

3 g of betulin-3,28-bis-(chloroacetate) (0.005 mol) was dissolved in 5 ml of 1-methyl-2-pyrolidinone, and 2,15 g of 2,4-lutidine (0.02 mol) was added. The reaction mixture was heated up to 65° C. overnight. Reaction mixture was added in ethyl ether dropwise with stirring. The precipitate was filtrated and dissolved in a small volume of CHCl₃. The CHCl₃ solution was added to ethyl ether and the filtered precipitate was washed twice with ethyl ether. 3.151 g Yield.

Example 45

Lup-20(29)-ene3,28-bis[N-(3,5-dimethylpyridinium) acetate] dichloride

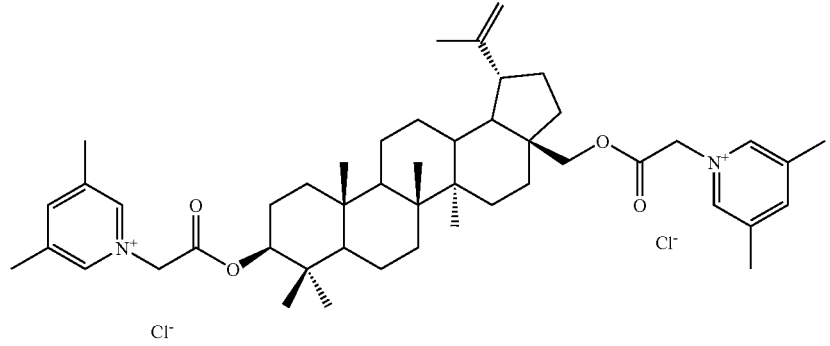

3 g of betulin-3,28-bis(chloroacetate) (0.005 mol) was dissolved in 5 ml of 1-methyl-2-pyrolidinone and 2,15 g of 3,5-lutidine (0.02 mol) was added. The reaction mixture was heated up to 65° C. overnight. The reaction mixture was added in ethyl ether dropwise with stirring. The precipitate was filtered and dissolved in a small volume of CHCl₃. The CHCl₃ solution was added to ethyl ether and the filtered precipitate was washed twice with ethyl ether. 3.44 g Yield.

Example 46

Lup-20(29)-ene-3,28-bis[N-(4-dimethylaminopyridinium)acetate] dichloride

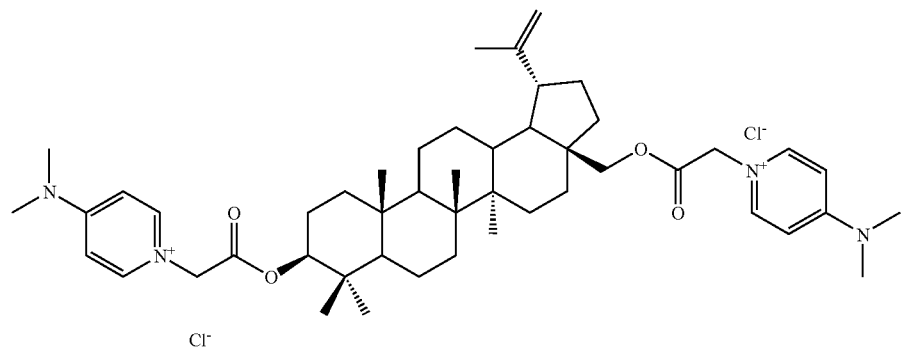

1 g of betulin-3,28-bis-(chloroacetate) (0.0017 mol) was dissolved in 5 ml of DMFA, and 0.75 g of 4-(dimethylamino) pyridine (0.06 mol) was added. The reaction mixture was heated up to 65° C. overnight. The reaction mixture was added to ethyl ether dropwise with stirring. The precipitate was filtered and washed twice with ethyl ether.

Example 47

Lup-20(29)-ene-3-[N-(2-methylpyridinium)acetate] chloride

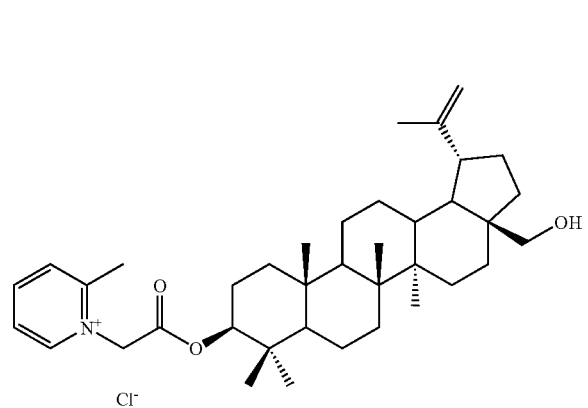

1 g of Betulin 3-(chloroacetate) (0.0019 mol) was dissolved in 5 ml of DMFA and 0.36 g of 2-methylpyridine (0.004 mol) was added. The reaction mixture was heated up to 65° C. overnight. The reaction mixture was added in ethyl ether dropwise with stirring. The precipitate was filtered and washed twice with ethyl ether. 0.8 g Yield.

Example 48

Lup-20(29)-ene-3-[N-(2,4-dimethylpyridinium)acetate] chloride

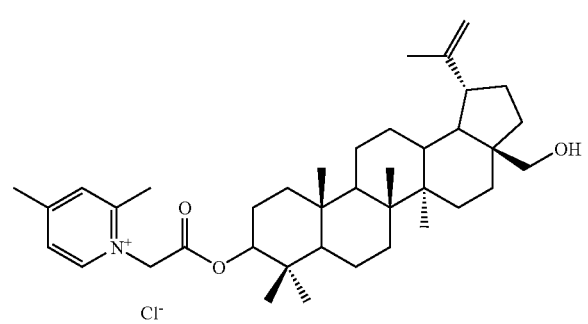

1 g of betulin 3 (chloroacetate) (0.0019 mol) was dissolved in 5 ml of DMFA, and 0.41 g of 2,4-lutidine (0.004 mol) was added. The reaction mixture was heated up to 65° C. overnight. The reaction mixture was added to ethyl ether dropwise with stirring. The precipitate was filtered and washed twice with ethyl ether. 1.02 g Yield.

Example 49

Lup-20(29)-ene-3-[N-(4-hydroxy-N-methylpiperidino)acetate] chloride

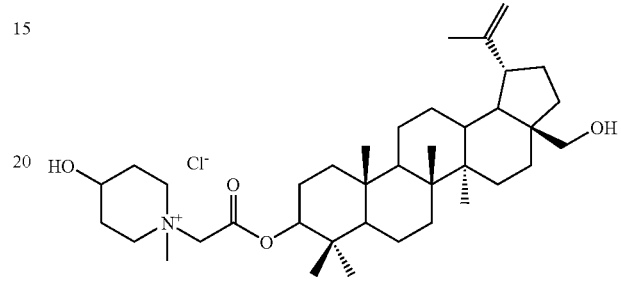

2 g of betulin-3-(chloroacetate) (0.0039 mol) was dissolved in 5 ml of dimethylacetamide and placed into a 50-ml flask. A solution of 1.78 g of 4-hydroxy-1-methylpiperidine (0.0156 mol) in 3 ml of dimethylacetamide was added into the same flask. The reaction mixture was heated up to 60° C. for 2 hours. The dimethylacetamide with the precipitate of the product of reaction was cooled down to room temperature and diluted with ethyl ether. Solid part was filtrated and washed twice with Ethyl Ether. Then the precipitate was dissolved in a minimal volume of isopropanol and reprecipitated with ethyl ether. Traces of solvents were evaporated with an oil pump.

Example 50

Lup-20(29)-ene-3-[N-(N-methylmorpholino)acetate) chloride

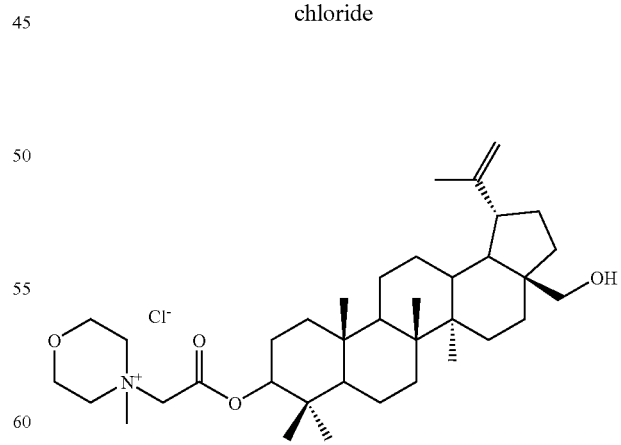

2 g of betulin-3-(chloroacetate) (0.0039 mol) was dissolved in 5 ml of dimethylacetamide and placed into a 50-ml flask. A solution of 0.8 g of 4-methylmorpholine (0.0078 mol) in 3 ml of dimethylacetamide was added into the same flask. The reaction mixture was heated up to 60° C. for 2 hours. The dimethylacetamide with the precipitate of the product of reaction was cooled down to room temperature and diluted with ethyl ether. The solid part was filtered and washed twice with ethyl ether. Then the precipitate was dissolved in a minimal volume of isopropanol and reprecipitated with ethyl ether. Traces of solvents were evaporated with an oil pump.

Example 51

Lup-20(29)-ene-3-[N-(3,5-dimethylpyridinium)acetate] chloride

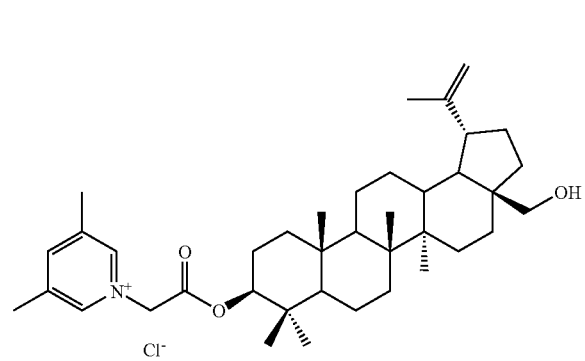

2 g of betulin-3-(chloroacetate) (0.0039 mol) was dissolved in 5 ml of dimethylacetamide and placed into a 50-ml flask. A solution of 0.85 g of 3,5-Lutidine (0.0078 mol) in 3 ml of dimethylacetamide was added into the same flask. Reaction mixture was heated up to 60° C. for 2 hours. The dimethylacetamide with the precipitate of the product of reaction was cooled down to room temperature and diluted with ethyl ether. The solid part was filtered and washed twice with ethyl ether. Then the precipitate was dissolved in a minimal volume of isopropanol and reprecipitated with ethyl ether. Traces of solvents were evaporated with an oil pump.

Example 52

Lup-20(29)-ene-3-[N-(4-dimethylaminopyridinium) acetate] chloride

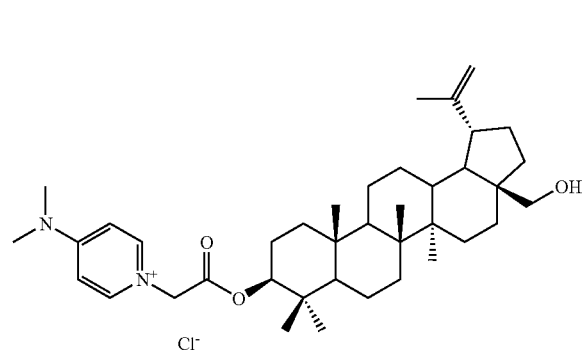

2 g of betulin-3-(chloroacetate) (0.0039 mol) was dissolved in 5 ml of dimethylacetamide and placed into a 50-ml flask. A solution of 0.95 g of 4-(dimethylamino) pyridine (0.0078 mol) in 3 ml of dimethylacetamide was added into the same flask. The reaction mixture was heated up to 60° C. for 2 hours. Dimethylacetamide with the precipitate of the product of reaction was cooled down to room temperature and diluted with ethyl ether. The solid part was filtered and washed twice with ethyl ether. Then the precipitate was dissolved in a minimal volume of isopropanol and reprecipitated with ethyl ether. Traces of solvents were evaporated with an oil pump.

Example 53

Lup-20(29)-ene-3,28-bis(octyldimethylammoniumacetate) dichloride

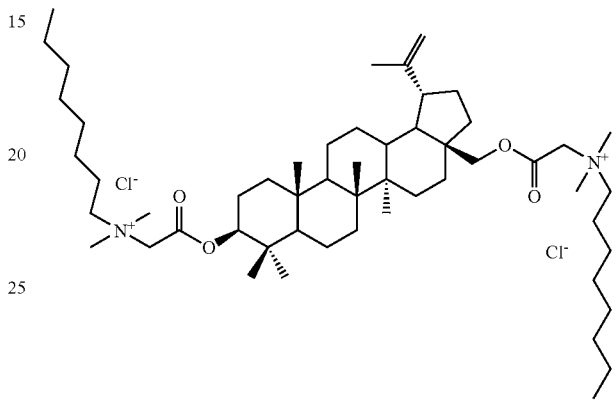

5 g of betulin-3,28-bis(chloroacetate) (0.0084 mol) was dissolved in 15 ml of DMFA, and 2.9 g of ADMA 8 Amine (Octyldimethylamine) (0.0185 mol) was added. The reaction mixture was heated up to 65° C. for 7 hours. The solid part of reaction mixture was filtered and washed with ethyl ether once. Then the precipitate was dissolved in a minimal volume of isopropanol (15 ml) and diluted with ethyl ether. The precipitate was filtered and dried with an oil pump.

Example 54

Lup-20(29)-ene-3,28-bis(octyldimethylammoniumacetate) dichloride

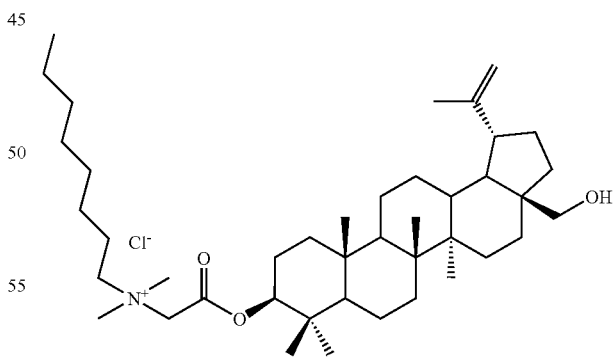

5 g of betulin 3(chloroacetate) (0.0096 mol) was dissolved in 15 ml of DMFA, and 1.67 g of ADMA 8 Amine (Octyldimethylamine) (0.0106 mol) was added. The reaction mixture was heated up to 65° C. for 7 hours. The solid part of the reaction mixture was filtered and washed with ethyl ether once. Then the precipitate was dissolved in a minimal volume of isopropanol (15 ml) and diluted with ethyl ether. The precipitate was filtered and dried with an oil pump.

Example 55

Lup-20(29)-ene-3,28-bis(tetradecyldimethylamoniumacetate) dichloride

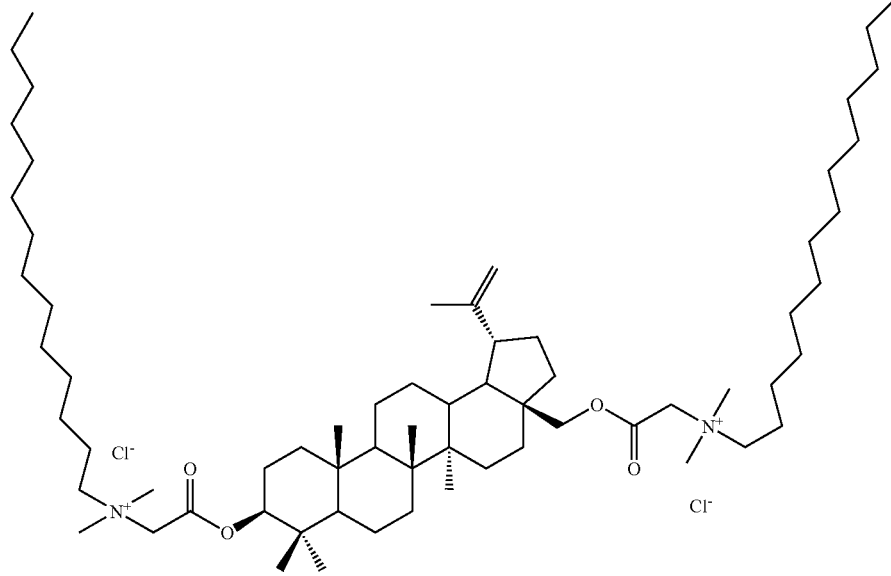

5 g of betulin-3,28-bis (chloroacetate) (0.0084 mol) was dissolved in 15 ml of DMFA, and 4.46 g of ADMA 14 Amine (tetradecyldimethylamine) (0.0185 mol) was added. The reaction mixture was heated up to 65° C. for 7 hours. The solid part of the reaction mixture was filtered and washed with ethyl ether once. Then the precipitate was dissolved in a minimal volume of isopropanol (15 ml) and diluted with ethyl ether. The precipitate was filtered and dried with an oil pump.

Example 56

Lup20(29)-ene3-tetradecyldimethylamoniumacetate chloride

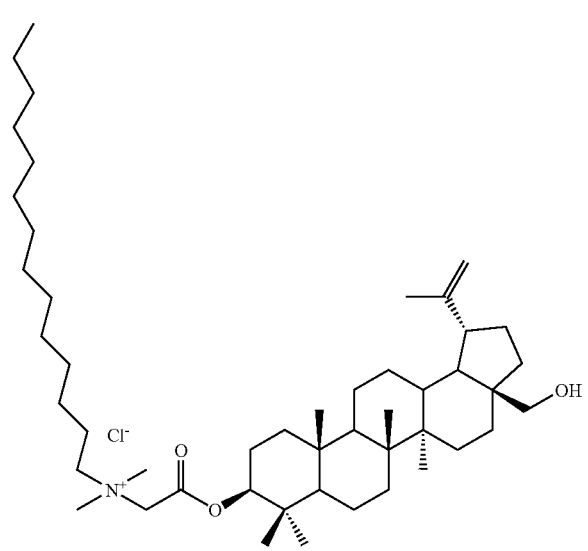

5 g of betulin-3(chloroacetate) (0.0096 mol) was dissolved in 15 ml of DMFA, and 2.55 g of ADMA14 Amine (tetracyldimethylamine) (0.0106 mol) was added. The reaction mixture was heated up to 65° C. for 7 hours. The solid part of the reaction mixture was filtered and washed with ethyl ether once. Then the precipitate was dissolved in a minimal volume of isopropanol (15 ml) and diluted with ethyl ether. The precipitate was filtered and dried with an oil pump.

Example 57

1-[(19β,28-epoxy-18α-oleanan-3β-yl)oxycarbonyl-methyl]-4-aza-1-azonia-bicyclo[2.2.2]octane chloride

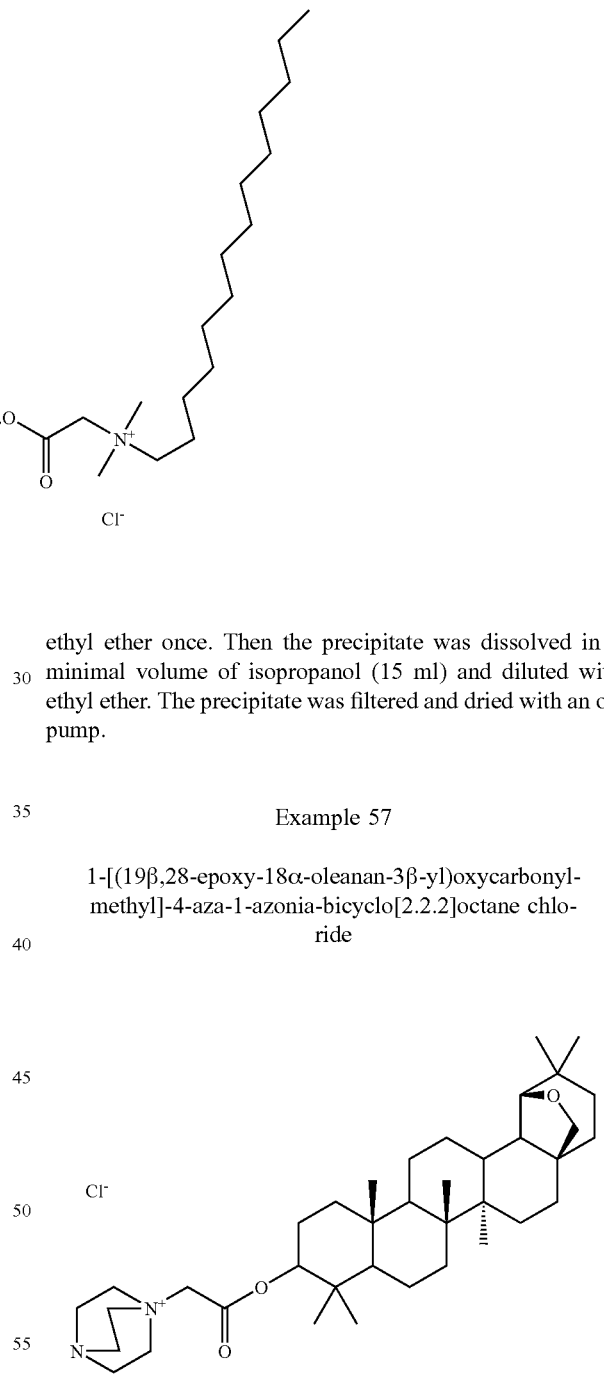

To a solution of 2.0 g (3.8 mmol) of 3β-chloroacetoxy-19β,28-epoxy-18α-oleanan in 20 mL of toluene, 0.86 g (7.6 mmol) of DABCO in 20 mL of toluene was added and the mixture was kept at 80° C. for 6 h. The precipitate was filtered, washed with toluene, and dried to yield 2.24 g (92%) of the product. 1H NMR (CDCl$_3$, TMS): 0.76–1.95 (45H, m), 3.11 (6H, m), 3.48, 3.81 (2H, AB, J=7.8 Hz), 3.54 (6H, m), 3.56 (1H, br s), 4.58 (1H, m), 5.30 (2H, s).

Example 58

[(19β,28-epoxy-18α-oleanan-3β-yl)oxycarbonylmethyl]trimethylammonium chloride

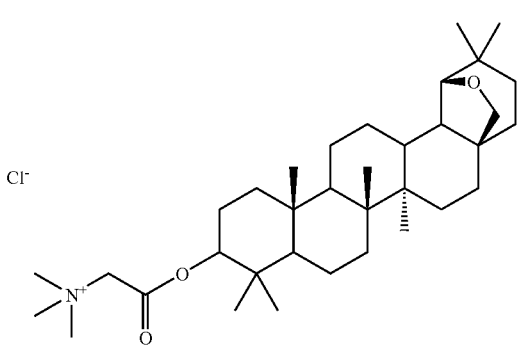

To the solution of 2.0 g (3.8 mmol) of 3β-chloroacetoxy-19β,28-epoxy-18α-oleanan in 10 mL of dry DMFA, trimethylamine was bubbled at room temperature overnight. The mixture was diluted with benzene; the precipitate was filtered, washed with benzene, and dried to yield 2.1 g (94%) of the product. $^1$H NMR (CDCl$_3$, TMS): 0.70–1.90 (45H, m), 3.40 (9H, s), 3.47, 3.81 (2H, AB, J=7.8 Hz), 3.57 (1H, br s), 4.57 (1H, m), 5.10 (2H, s).

Example 59

1-[(19β,28epoxy-18α-oleanan-3β-yl)oxycarbonylmethyl]pyridinium chloride

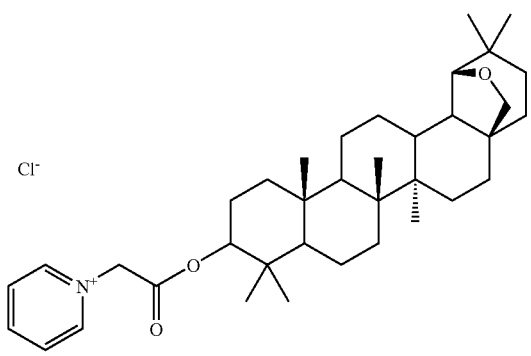

A solution of 2.0 g (3.8 mmol) of 3β-chloroacetoxy-19β,28-epoxy-18α-oleanan in 10 mL of dry pyridine was kept at 80° C. for 6 h. Benzene (30 ml) was added; the solids were filtered off, washed with benzene, and dried to give 2.24 g (97%) of the product. $^1$H NMR (CDCl$_3$, TMS): 0.65–1.87 (45H, m), 3.46, 3.80 (2H, AB, J=7.8 Hz), 3.54 (1H, br s), 4.55 (1H, m), 5.95 (2H, s), 8.27 (2H, m), 8.76 (1H, m), 9.20 (2H, m).

Example 60

1-[(lup-20(29)-en-3β-yl)oxycarbonylmethyl]-4-aza-1-azonia-bicyclo[2.2.2]octane chloride

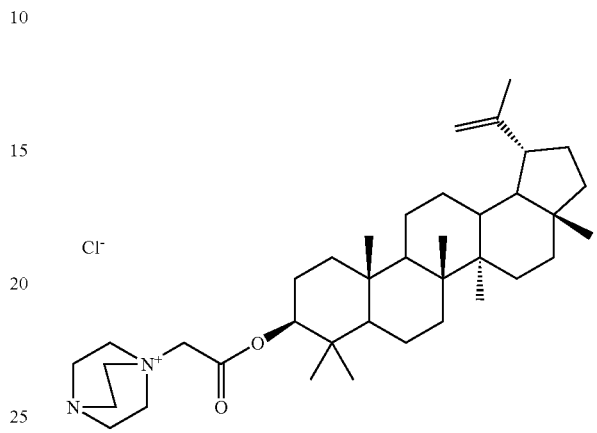

To a solution of 2.0 g (4.0 mmol) of 3β-chloroacetoxylup-20(29)-ene in 20 mL of toluene 0.89 g (7.9 mmol) of DABCO in 20 mL of toluene was added, and the mixture was kept at 80° C. for 6 h. The precipitate was filtered, washed with toluene, and dried to yield 2.24 g (92%) of the product. $^1$H NMR (CDCl$_3$, TMS): 0.75–1.80 (46H, m), 3.10 (6H, m), 3.55 (6H, m), 4.51 (1H, m), 4.57 (1H, s), 4.70 (lH, s), 5.25 (2H, s).

Example 61

1-[(lup-20(29)-en-3β-yl)oxycarbonylmethyl]trimethylammonium chloride

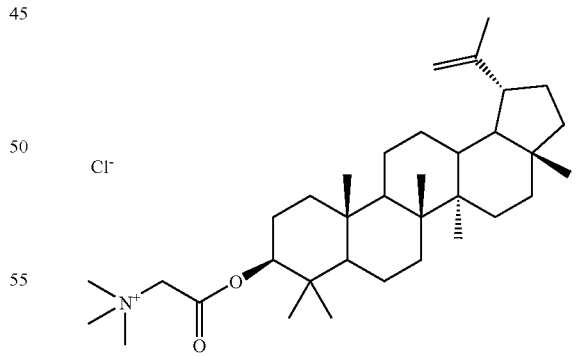

To the solution of 2.0 g (4.0 mmol) of 3β-chloroacetoxy-lup-20(29)-ene in 10 mL of dry DMFA trimethylamine was bubbled at room temperature overnight. The mixture was diluted with benzene; the precipitate filtered, washed with benzene and dried to yield 2.03 g (91%) of the product. $^1$H NMR (CDCl$_3$, TMS): 0.77–1.89 (46H, m), 3.43 (9H, s), 4.47 (1H, m), 4.59 (1H, s), 4.72 (1H, s), 5.15 (2H, s).

Example 62

1-[(lup-20(29)-en-3β-yl)oxycarbonylmethyl]pyridinium chloride

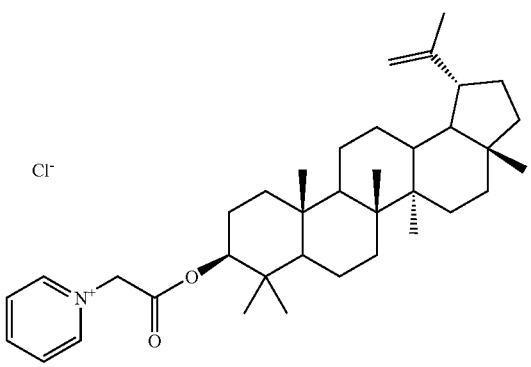

A solution of 2.0 g (4.0 mmol) of 3β-chloroacetoxylup-20(29)-ene in 10 mL of dry pyridine was kept at 80° C. for 6 h. Benzene (30 ml) was added; the solids were filtered off, washed with benzene, and dried to give 2.29 g (99%) of the product. $^1$H NMR (CDCl$_3$, TMS): 0.80–1.90 (46H, m), 4.50 (1H, m), 4.55 (1H, s), 4.68 (1H, s), 5.90 (2H, s), 8.25 (2H, m), 8.78 (1H, m), 9.21 (2H, m).

Example 63

Betulin-3,28-bis(N,N-dimethylethanolacetoxyammonium) dibromide

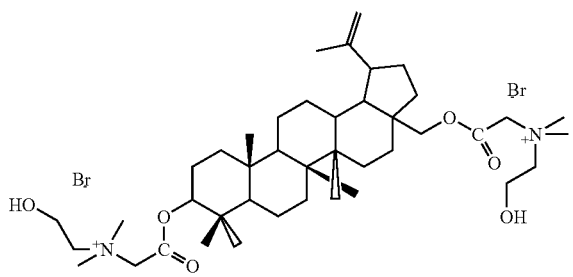

Betulin-3,28-dichloroacetate (3 g., 4.4 mmol) and N,N-dimethylethanolamine (2.34 g., 0.0264 mol) were dissolved in 10 ml. of dimethylacetamide. The reaction mixture was kept at room temperature for one hour. The solid part was filtered, washed twice with ethyl ether, dissolved in methanol (3 ml.), and diluted with ethyl ether again. 3.60 g. of final product was obtained after filtration and drying in vacuum $^1$H NMR (300 MHz, CDCl$_3$+(CD$_3$)$_2$SO): 4.71s, 1H), 4.61 (m, 6H), 4.39 (d, J=10.4, 1H), 3.95 (m, 5H), 3.78 (bs, 4H), 3.41 (m, 12H), 2.46 (m, 1H), 1.96–0.65 (m, 42H).

Example 64

Betulin-3,28-bis(N,N-dimethylethanolbutiroxyammonium) dibromide (64)

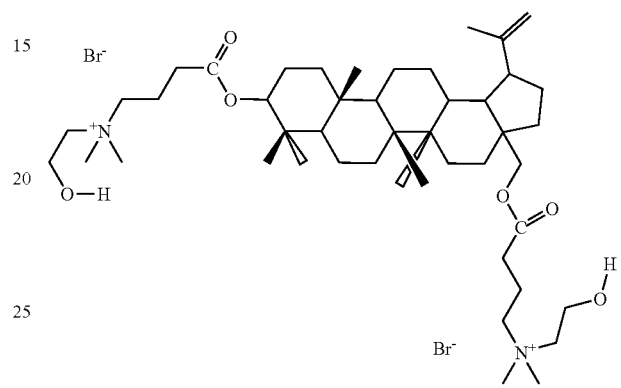

Betulin-3,28-di (4-bromoacetate) (2.85 g, 3.1 mmol) and N,N-dimethylethanolamine (2.0 g, 18.0 mmol) were dissolved in 10 ml of dimethylacetamide. The reaction mixture was kept at room temperature overnight (16 hours). The solid part was filtered, washed twice with ethyl ether, dissolved in methanol (3 ml), and diluted with ethyl ether. 3.24 g of final product was obtained after filtration and drying in vacuum.

$^1$H NMR (300 MHz, CDCl$_3$+(CD$_3$)$_2$SO): 4.72(s, 1H), 4.57 (s, 1H), 4.48 (dd, J$_1$=6.8, J$_2$=6,0 Hz, 1H), 4.29 (d, J=10.4, 1H), 4.10 (bs, 4H), 3.86 (d, J=10.5 Hz, 1H), 3.69 (m, 8H), 3.36 (m, 12H), 2.35 (m, 5H), 2.10 (m, 4H), 1.96–0.65 (m, 42H).

Example 65

Betulin-3,23bis(didecylmethylammoniumacetoxy) dichloride

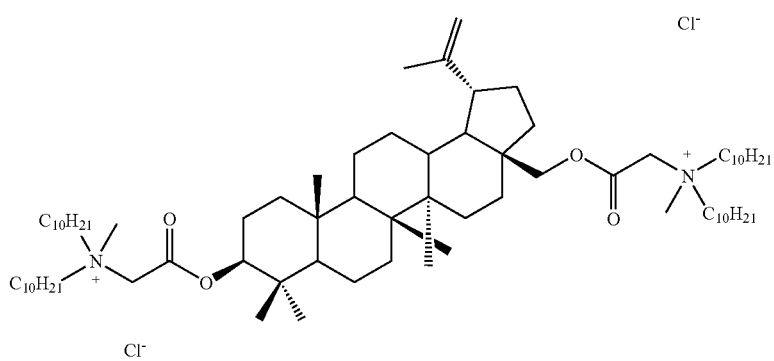

Betulin-3,28-di(chloroacetate) (5 g, 8.4 mmol) and didecylmethylamine (5.75 g, 18.5 mmol) were dissolved in 25 ml of tetrahydrofurane. The reaction mixture was kept at temperature 70° C. for 6 hours. THF was evaporated on rotary evaporator. The solid part was washed with hexane. 8.1 g of final product was obtained after filtration and drying in vacuum

Example 66
Betulin-3,28-bis(didecylmethylammoniumacetoxy) dibromide (66)

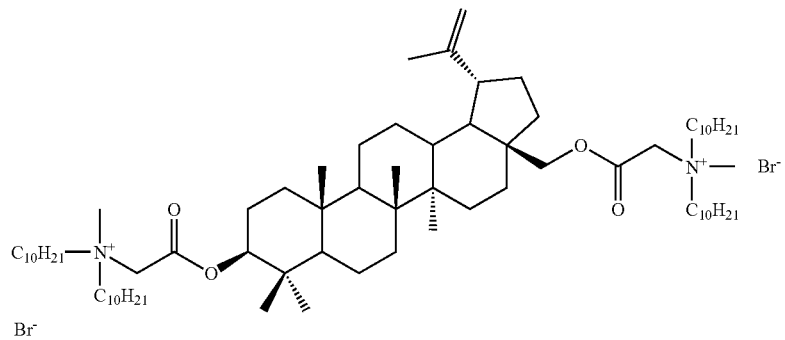

Betulin-3,28-di(bromoacetate) (5 g., 7.3 mmol) and didecylmethylamine (5.03 g., 16 mmol) were dissolved in 25 ml of tetrahydrofurane. The reaction mixture was kept at 70° C. for 6 hours. THF was evaporated on rotary evaporator. The solid part was washed with hexane. 9.2 g of final product was obtained after filtration and drying in vacuum

Example 67
Betulin-3-(didecylmethylammoniumacetoxy) chloride

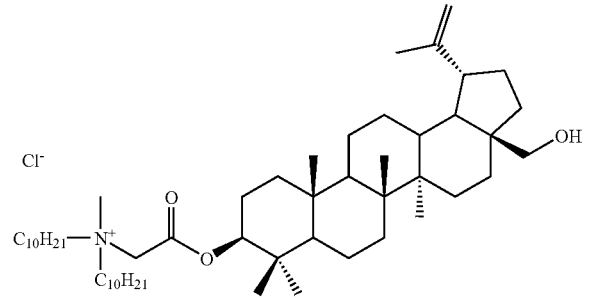

Betulin-3-bromoacetate (3 g, 9.6 mmol) and didecylmethylamine (2.0 g, 10.6 mmol) were dissolved in 25 ml of tetrahydrofurane. The reaction mixture was kept at 70° C. for 6 hours. THF was evaporated on rotary evaporator. The solid part was washed with hexane. 9.2 g of final product was obtained after filtration and drying in vacuum.

Example 68
3β-(N-diazabicyclo[2.2.2]octylacetyloxy)-19β,28-epoxy-18α-oleanan bromide

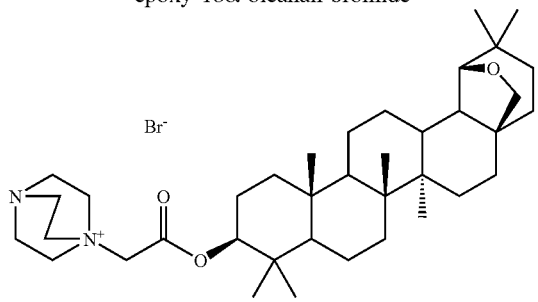

A solution of 0.82 g (0.0074 M) of diazabicyclo [2.2.2] octane (DABCO) in 15 ml of DMFA was added to a suspension of 3-bromoacetylallobetulin (2.064 g, 0.0037 M) in 20 ml of DMFA. The mixture was stirred at room temperature overnight, diethyl ether and benzene were added to the mixture. The white precipitate was filtered off, washed with diethyl ether and hexane, and dried furnishing the title compound (2.3 g, 0.0034 M, 92%) as a white solid.

M.p.=339–340° C. (Decomp.)

$^1$H NMR (CDCl$_3$+CF$_3$CO$_2$D, 300 MHz): 4.72 (dd, 1H, 3H), 4.55–4.14 (complex, 7×2H, CH2), 3.98 (d, J=10.3, 1H, 28H), 3.9 (s, 1H, 19H), 3.66 (d, J=10.3, 28H), 1.84–1.43 (complex, CH, CH2), 1.0–0.86 (7×3H, CH3).

$^{13}$C NMR (CDCl$_3$+CF$_3$CO$_2$D, 75 MHz): 163.11, 89.70, 87.11, 71.12, 61.94, 55.51, 51.80, 50.93, 46.62, 44.37, 41.70, 40.74, 40.60, 38.35, 37.90, 37.07, 36.20, 35.96, 34.08, 33.70, 32.44, 28.30, 27.58, 26.18, 25.75, 24.22, 23.31, 20.88, 18.01, 16.13, 15.76, 15.29, 13.37

IR (KBr): 3433.6, 3239.3, 2938.3, 2860.6, 1735.9, 1221.2

Example 69
3β-(N-pyridiniumacetyloxy)-19β,28-epoxy-18α-oleanan bromide

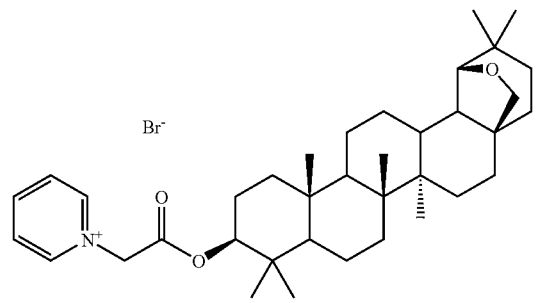

A suspension of 3-bromoacetylallobetulin (2.064 g, 0.0037 M) in 10 ml of pyridine was stirred at room temperature overnight. Diethyl ether was added to the suspension. The white precipitate was filtered off, washed with diethyl ether and hexane, and dried, furnishing the title compound (2.3 g, 97%) as a yellowish solid.

M.p. 327–329° C. (Decomp.)

$^1$H NMR (CDCl$_3$+CF$_3$CO$_2$D, 300 MHz): 8.93 (d), 8.61 (t) and 8.17 (t) (all pyridine H, 5H), 5.77 and 5.67 (dd, 2H, CH2), 4.68 (t, 1H, 3H), 3.99 (d, J=10.3, 1H, 28H), 3.89 (s, 1H, 19H), 3.65 (d, J=10.3, 28H), 1.82–1.19 (complex, CH, CH2), 0.995–0.82 (7×3H, CH3).

$^{13}$C NMR (CDCl$_3$+CF$_3$CO$_2$D, 75 MHz): 165.99, 146.83, 145.99, 128.52, 89.87, 87.43, 71.19, 61.79, 55.57, 50.99, 46.67, 41.76, 40.79, 40.65, 38.41, 38.03, 37.12, 36.22, 35.99, 34.15, 33.73, 32.47, 28.27, 27.77, 26.21, 25.75, 24.23, 23.44, 20.93, 18.02, 16.16, 15.99, 15.30, 13.39

IR (KBr): 3417.1, 2922.6, 2867.6, 1742.4, 1637.1, 1490.6, 1444.8, 1376.1, 1234.2

Example 70

3β-[-(N',N'-dimethylaminopyridinium)-N-acetyloxy]-19β,28-epoxy-18α-oleanan bromide

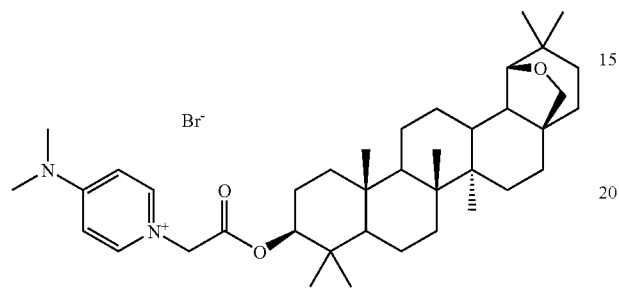

A mixture of 3-bromoacetylallobetulin (2.064 g, 0.0037 M) and N,N-dimethylaminopyridine (0.9 g, 0.0074 m) in 50 ml dimethylacetamide was stirred at room temperature over 3 h, and treated with diethyl ether. The precipitate was filtered off, washed with ether and dried, furnishing the title compound (2.3 g, 91) as a yellowish solid.

M.p. 323–326° C. (Decomp. subl.)

$^1$H NMR (CDCl$_3$, 300 MHz): 8.54 (t) and 6.99 (d) (all pyridine H, 4H), 5.55 (d, 2H, CH2), 4.57 (t, 1H, 3H), 3.77 (d, J=10.3, 1H, 28H), 3.52 (s, 1H, 19H), 3.44 (d, J=10.3, 28H), 3.3 (s, 6H, 3×CH3),1.76–1.12 (complex, CH, CH2), 0.97–0.79 (7×3H, CH3).

$^{13}$C NMR (CDCl$_3$, 75 MHz): 166.13, 155.93, 143.30, 107.14, 87.36, 83.76, 70.70, 57.32, 54.97, 50.40, 46.25, 40.91, 40.17, 40.11, 40.06, 37.99, 37.41, 36.57, 36.18, 35.72, 33.57, 33.42, 32.14, 28.27, 27.70, 25.86, 25.70, 24.01, 23.15, 20.49, 17.53, 16.0, 15.15, 12.96

IR (KBr): 3427.4, 2934.3, 2859.9, 1736.8, 1648.4, 1448.3, 1392.5, 1211.1

Example 71

3β-1-(N',N'-dimethylaminopyridinium)-N-acetyloxy-19β,28epoxy-18α-oleanan chloride

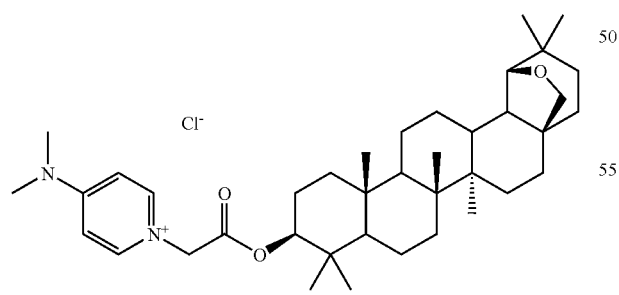

A mixture of 3-chloroacetylallobetulin (1.91 g, 0.0037 M) and N,N-dimethylaminopyridine (0.9 g, 0.0074 M) in 50 ml dimethylacetamide was stirred at room temperature overnight, and treated with diethyl ether and methanol. The precipitate was filtered off, washed with ether and dried furnishing the title compound (2.03 g, 86%) as a white solid.

M.p. 325–327° C. (decomp., subl.)

$^1$H NMR (CDCl$_3$, 300 MHz): 8.57 (t) and 6.94 (d) (all pyridine H, 4H), 5.51 (s, 2H, CH2), 4.52 (m, 1H, 3H), 3.73 (d, J=10.3, 1H, 28H), 3.47 (s, 1H, 19H), 3.40 (d, J=10.3, 28H), 3.25 (s, 6H, 3×CH3), 1.71–1.07 (complex, CH, CH2), 0.93–0.73 (7×3H, CH3).

$^{13}$C NMR (CDCl$_3$, 75 MHz): 166.62, 156.25, 149.60, 143.74, 107.44, 87.69, 83.95, 71.02, 57.48, 55.29, 50.71, 46.22, 42.46, 41.23, 40.49, 40.38, 38.30, 37.71, 36.88, 36.76, 36.50, 36.04, 33.89, 33.56, 32.47, 28.60, 28.00, 26.18, 24.33, 23.44, 20.80, 17.86, 16.33, 15.47, 13.29

IR (KBr): 3390.2, 2934.3, 2859.9, 1736.8, 1648.4, 1564.6, 1448.3, 1387.9, 1215.7

Example 72

3β-(N-octyldimethylaminoacetyloxy)-19β,28-epoxy-18α-oleanan bromide

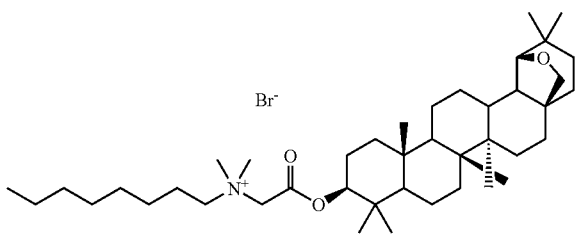

A mixture of 3-bromoacetylallobetulin (2.064 g, 0.0037 M) and octyldimethylamine (1.16 g, 0.0074 M) in 30 ml dimethylacetamide was stirred at room temperature overnight and treated with diethyl ether/benzene mixture. The precipitate was filtered off, washed with ether and dried, furnishing the title compound (1.7 g, 64%) as a white solid.

M.p. 275–277° C. (decomp.)

$^1$H NMR (CDCl$_3$+CF$_3$CO$_2$D, 300 MHz): 4.67 (dd, 1H, 3H), 4.36 *m, 2H, CH2), 3.97 (d, J=10.3, 1H, 28H), 3.87 (s, 1H, 19H), 3.64 (m, 3H, 28 H and N—CH2), 3.43 (s, 6H, 2×3H, CH3), 1.83–1.15 (complex, CH, CH2), 1.00–0.87 (7×3H, CH3).

$^{13}$C NMR (CDCl$_3$+CF$_3$CO$_2$D, 75 MHz): 163.80, 89.0, 85.25, 70.91, 65.50, 61.43, 55.48, 52.56, 52.44, 50.91, 46.57, 41.53, 40.66, 40.55, 38.43, 37.87, 37.07, 36.25, 35.96, 33.94, 33.69, 32.46, 31.49, 28.84, 28.46, 27.86, 26.18, 25.91, 25.82, 24.37, 23.48, 22.81, 22.47, 20.85, 18.0, 16.32, 16.16, 15.39, 13.92, 13.45

IR (KBr): 3436.7, 2925.0, 2850.6, 1727.5, 1462.3, 1262.3, 1201.8

Example 73

3β-[N-(2-hydroxyethyl)aminoacetyloxy]-19β,28-epoxy-18α-oleanan bromide

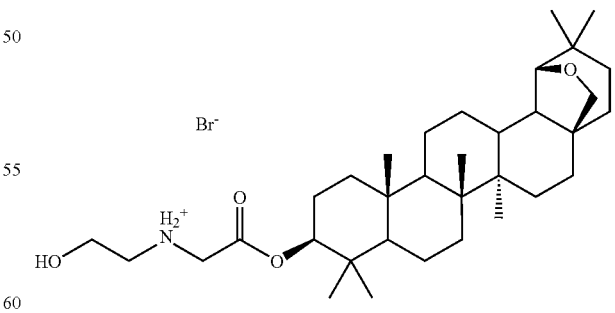

A mixture of 3-bromoacetylallobetulin (2.064 g, 0.0037 M) and ethanolamine (0.45 g, 0.0074 M) in 30 ml of DMFA was stirred at room temperature for 24 hours and treated with methanol. The precipitate was filtered off, washed with methanol and dried, furnishing the title compound (1.1 g, 48%) as a white solid.

M.p. 319–322° C. (decomp.)

¹H NMR (CDCl₃+CF₃CO₂D, 300 Hz): 4.71 (m, 1H, 3H), 4.13–3.39 (complex, 9H, CH2, 19H and 28H), 1.83–1.19 (complex, CH, CH2), 0.99–0.86 (7×3H, CH3).

¹³C NMR (CDCl₃+CF₃CO₂D, 300 Hz): 165.92, 89.16, 86.06, 70.94, 57.05, 55.43, 50.88, 49.85, 48.12, 46.57, 41.56, 40.67, 40.55, 38.35, 38.11, 37.87, 37.05, 36.25, 35.96, 33.98, 33.67, 32.47, 28.43, 27.58, 26.18, 25.81, 24.35, 23.34, 20.85, 17.99, 16.32, 16.16, 15.38, 13.41

IR (KBr): 3213.4, 2934.3, 2859.9, 1732.1, 1453.0, 1387.9, 1220.4, 1197.1, 1146.0

Example 74

3β-[N,N-dimethyl-N-(2-hydroxyethyl)aminoacetyloxy]-19β,28-epoxy-18α-oleanan bromide

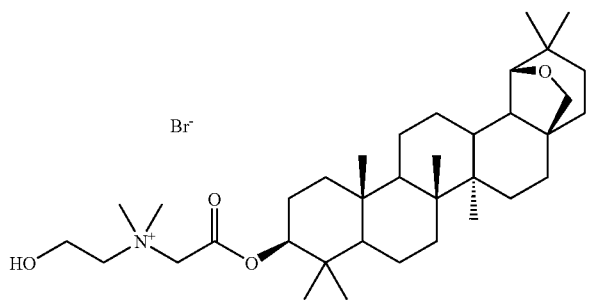

A mixture of 3-bromoacetylallobetulin (2.064 g, 0.0037 M) and dimethylaminoethanol (0.67 g, 0.0074 M) in 50 ml of DMA was stirred at room temperature overnight and treated with diethyl ether/hexane. The precipitate was filtered off, washed with methanol/hexane and dried, furnishing the title compound (2.27 g, 94%) as a white solid.

M.p. 316–318° C. (decomp.)

¹H NMR (CDCl₃+CF₃CO₂D, 300 Hz): 4.70 (m, 1H, 3H), 4.48–3.64 (complex, 9H, CH2, 19H and 28H), 3.49 (s, 6H, 2×3H, CH3), 1.83–1.20 (complex, CH, CH2), 1.00–0.86 (7×3H, CH3).

¹³C NMR (CDCl₃+CF₃CO₂D, 300 Hz): 163.91, 86.18, 85.70, 71.00, 66.36, 63.15, 62.87, 62.36, 60.88, 55.99, 55.50, 54.20, 53.49, 50.92, 46.59, 41.615, 40.71, 40.58, 38.39, 37.87, 37.08, 36.23, 35.97, 34.03, 33.70, 32.46, 28.39, 27.76, 26.18, 25.79, 24.32, 23.45, 20.87, 18.01, 16.24, 16.04, 15.35, 13.43

IR (KBr): 3283.6, 2934.3, 1732.8, 1643.2, 1199.9

Example 75

3β-[N,N-dimethyl-N-(2-hydroxyethyl)aminoacetyloxy]-19β,28-epoxy-18α-oleanan chloride

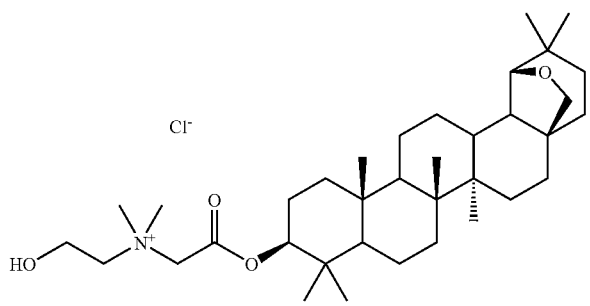

A mixture of 3-chloroacetylallobetulin (1, 91 g, 0.0037 M) and dimethylaminoethanol (0.67 g, 0.0074 M) in 50 ml of DMA was stirred at room temperature for 24 hours and treated with diethyl ether/methanol. The precipitate was filtered off, washed with hexane and dried furnishing the title compound (1.7 g, 76%) as a white solid.

M.p. 271–273° C. (decomp.)

¹H NMR (CDCl₃+CF₃CO₂D, 300 Hz): 4.71 (m, 1H, 3H), 4.48–3.24 (complex, 9H, CH2, 19H and 28H), 3.47 (s, 6H, 2×3H, CH3),1.82–1.19 (complex, CH, CH2), 1.00–0.86 (7×3H, CH3).

¹³C NMR (CDCl₃+CF₃CO₂D, 300 Hz): 163.86, 89.28, 85.67, 70.98, 66.34, 62.27, 56.06, 55.50, 53.39, 50.90, 46.59, 41.60, 40.69, 40.56, 38.38, 37.84, 37.06, 36.23, 35.96, 34.02, 33.69, 32.47, 28.39, 27.71, 26.18, 25.80, 24.32, 23.42, 20.86, 18.0, 16.24, 16.0, 15.34, 13.43

IR (KBr): 3390.2, 3287.8, 2934.3, 2869.2, 2357.4, 1736.8, 1634.4, 1457.6

Example 76

3β-[N-(3-hydroxymethylpyridinium)acetyloxy]-19β,28-epoxy-18α-oleanan bromide

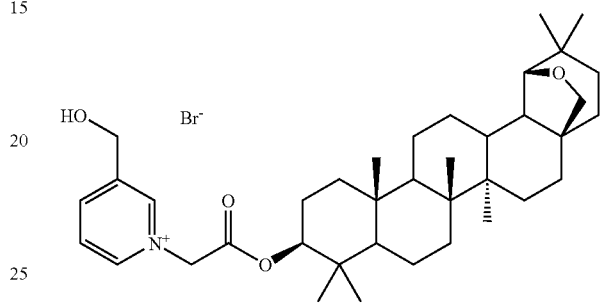

A mixture of 3-bromoacetylallobetulin (2.064 g, 0.0037 M) and 3-pyridylcarbinol (0.82 g, 0.0075 M) in 50 ml of DMA was stirred at room temperature overnight and treated with diethyl ether/hexane. The precipitate was filtered off, washed with hexane and dried, furnishing the title compound (2.26 g, 94%) as a white solid.

M.p. 325–327° C. (decomp.)

¹H NMR (CDCl₃+CF₃CO₂D, 300 Hz): 9.0 (s), 8.65 and 8.58 (dd), 8.09 (m) (4H, pyridine), 5.6, (m, 2H, CH2), 5.12 (s ,2H, CH2), 4.690 (m, 1H, 3H), 4.02 (d, J=10.3, 1H, 28H), 3.89 (s, 1H, 19H), 3.66 (d. J=10.3, 1H, 28H), 1.83–1.20 (complex, CH, CH2), 0.99–0.84 (7×3H, CH3).

¹³C NMR (CDCl₃+CF₃CO₂D, 300 Hz): 165.30, 145.99, 144.84, 143.99, 142.57, 135.55, 128.44, 127.67, 89.27, 86.90, 70.97, 64.24, 61.80, 61.49, 60.10, 55.46, 50.87, 46.57, 41.58, 40.69, 40.55, 38.35, 37.92, 37.03, 36.22, 35.96, 34.00, 33.67, 32.44, 28.38, 27.77, 26.16, 25.78, 24.31, 23.36, 20.85, 17.96, 16.22, 16.05, 15.33, 13.40

IR (KBr): 3265.7, 2943.3, 2862.7, 1737.3, 1638.7, 1468.6, 1379.0, 1280.5, 1240.2

Example 77

3β-[(N,N,N',N'-tetramethylethylenediamino)acetyloxy]-19β,28-epoxy-18α-oleanan bromide

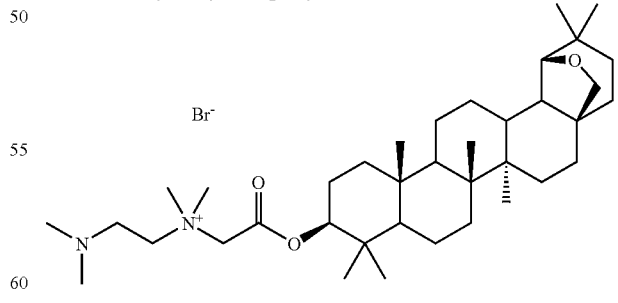

A mixture of 3-bromoacetylallobetulin (2.064 g, 0.0037 M) and tetramethylethylenediamine (TMEDA) (0.86 g, 0.0075 M) in 30 ml of DMFA was stirred at room temperature overnight and treated with diethyl ether/benzene. The precipitate was filtered off, washed with ether/benzene and dried, furnishing the title compound (2.35 g, 93%) as a white solid.

M.p. 324–326° C. (decomp.)

¹H NMR (CDCl₃+CF₃CO₂D, 300 Hz): 4.7 (m, 1H, 3H), 4.3–3.6 (complex, 9H, CH, CH2), 3.46 (s, 2×3H, CH3), 3.1 (s (6H, CH3), 1.89–1.20 (complex, CH, CH2), 1.00–0.86 (7×3H, CH3).

¹³C NMR (CDCl₃+CF₃CO₂D, 300 Hz): 163.31, 89.25, 86.42, 70.98, 62.77, 58.72, 55.47, 52.37, 52.25, 50.91, 50.0, 46.59, 44.15, 41.59, 40.69, 40.57, 38.35, 37.82, 37.05, 36.24, 35.97, 34.02, 33.68, 32.46, 28.39, 27.62, 26.18, 25.80, 24.31, 23.30, 20.86, 18.01, 16.22, 15.84, 15.34, 13.42

(KBr): 3426.2, 2931.7, 2867.6, 1733.3, 1467.7, 1449.4, 1266.2, 1220.4

Example 78

3β-[(N,N-dimethyl-N-octyl)aminoacetyloxy]-19β,28-epoxy-18α-oleanan chloride

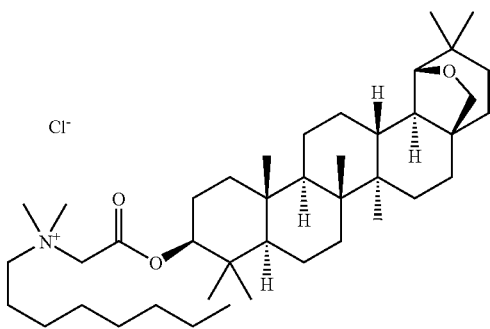

A mixture of 3-chloroacetylallobetulin (30 g, 0.058 mol) and octyldimethylamine (18.2 g, 0.116 mol) in 300 ml of dimethylacetamide was stirred at room temperature over 48 h, treated with diethyl ether afterwards. The precipitate was filtered off, washed with ether/hexane and dried, furnishing the title compound (32 g, 81%) as a white solid.

M.p. 245–247° C. (decomp.)

¹H NMR (CDCl₃, 300 MHz): 4.89 (s, 2H, CH2), 4.64 (m, 1H, 3-H), 3.8–3.48 (m, 15H, CH, CH2, CH3), 1.81–1.29 (m, CH, CH2), 1.00–0.82 (s, 7×3H, CH3).

¹³C NMR (CDCl₃, 75 MHz): 164.59, 87.86, 84.45, 71.20, 64.31, 61.00, 55.49, 51.97, 50.28, 46.75, 41.40, 40.66, 40.55, 38.42, 37.92, 37.06, 36.67, 36.20, 34.05, 33.71, 32.63, 31.53, 29.0, 28.75, 28.07, 26.18, 24.49, 23.64, 22.88, 22.50, 20.97, 18.03, 16.49, 15.63, 13.99, 13.42

IR (KBr): 3422.3, 2923.5, 2844.8, 1735.5, 1634.9, 1464.2, 1389.9, 1254.2, 1201.5

Example 79

3β-[(N,N-dimethyl-N-tetradecyl)aminoacetyloxy]-19β,28-epoxy-18α-oleanan chloride

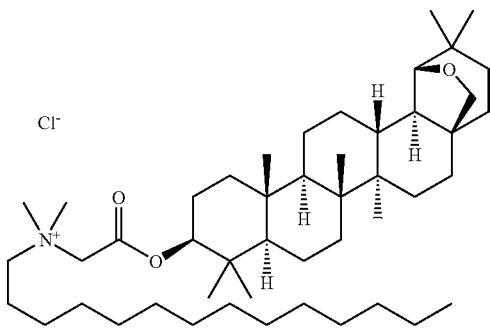

A mixture of 3-chloroacetylallobetulin (2.59 g, 0.005 mol) and tetradecyldimethylamine (2.35 g, 0.01 mol) in 50 ml dimethylacetamide was stirred at room temperature over 48 h, treated with diethyl ether/hexane afterwards. The precipitate was filtered off, washed with ether/hexane and dried, furnishing the title compound (3.5 g, 90%) as a white solid.

M. p. 244–246° C. (decomp.)

¹H NMR (CDCl₃, 300 MHz): 4.89 (s, 2H, CH2), 4.63 (m, 1H, 3-H), 3.8–3.7 (m, 9H, CH, CH2, CH3), 3.54 (s, 1H, 19-H), 3.45 (d, J=10.3, 28-H), 1.8–1.22 (m, CH, CH2), 0.99–0.81 (7×3H, CH3).

¹³C NMR (CDCl₃, 75 MHz): add data

IR (KBr): 3413.5, 2923.5, 28.53.5, 1735.5, 1468.6, 1254.2, 1201.7

Example 80

3β-[(N-methyl-N,N-didecyl)aminoacetyloxy]-19β,28-epoxy-18α-oleanan chloride

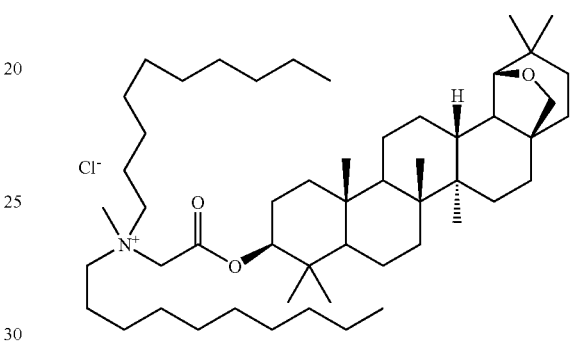

A mixture of 3-chloroacetylallobetulin (31 g, 0.06 mol.) and methyldidecylamine (37.1 g, 0.12 mol.) in 300 ml dimethylacetamide was stirred at 60° C. over 3 days. The reaction mixture was poured into large volume of diethyl ether. The precipitate was filtered off, washed with ether and dried, furnishing the title compound (37.3 g, 75%) as a colorless solid.

M. p. 203–204° C. (decomp.)

¹H NMR (CDCl₃, 300 MHz): 4.77 (s, 2H, CH2), 4.62 (m, 1H, 3-H), 3.86–3.45 (m, 10H, CH, CH2, CH3), 1.79–1.22 (m, CH, CH2), 1.00–0.82 (7×3H, CH3).

¹³C NMR (CDCl₃, 75 MHz): 164.59, 87.87, 84.53, 83.29, 71.20, 61.98, 59.63, 55.52, 50.94, 49.41, 46.76, 41.41, 41.19, 40.66, 38.48, 37.92, 37.09, 36.68, 36.20, 34.07, 32.65, 31.77, 29.32, 29.16, 28.74, 26.36, 26.18, 24.48, 23.63, 22.59, 20.97, 18.04, 16.46, 15.64, 14.04, 13.42

IR (KBr): 3396, 2923.5, 2853.5, 1735.5, 1464.3, 1376.7, 1228.0

Example 81

3β-[N,N-di (2-hydroxyethyl)aminoacetyloxy]-19β,28-epoxy-18α-oleanan bromide

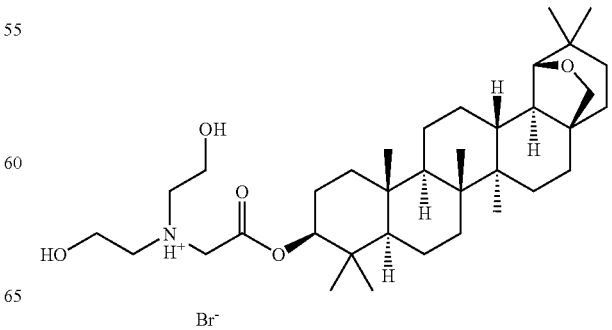

A mixture of 3-bromoacetyl allobetulin (3.1 g, 0.0055 mol) and diethanol amine (116 g, 0.011 mol) in 50 ml dimethylacetamide was stirred at room temperature overnight, treated with ethanol\hexane mixture. The precipitate was filtered off, washed with hexane and dried, furnishing the title compound (3.96 g, 99%) as a colorless solid.

M. p. 240–244° C. (decomp.)

$^1$H NMR (CDCl$_3$, 300 MHz): 4.61 (m, 1H, 3-H), 3.83–3.48 (m, 10H, CH, CH2,), 2.82 (m, 4H, CH2), 1.79–1.23 (m, CH, CH2), 1.02–0.84 (7×3H, CH3).

$^{13}$C NMR (CDCl$_3$, 75 MHz): 172.98, 87.93, 82.15, 71.25, 60.95, 59.89, 57.67, 56.10, 55.53, 50.94, 50.76, 46.80, 41.55, 40.71, 38.53, 37.85, 37.14, 36.72, 36.25, 34.12, 33.79, 32.69, 28.79, 28.02, 26.40, 24.52, 23.71, 21.00, 18.10, 16.59, 15.68, 13.48

IR (KBr): 3374.4, 2932.7, 1729.9, 1714.5, 1451.4, 1197.6, 1070.7

Example 82

Betulin-3,28 bis(N,N-dimethylethanolacetoxyammonium) dichloride (62)

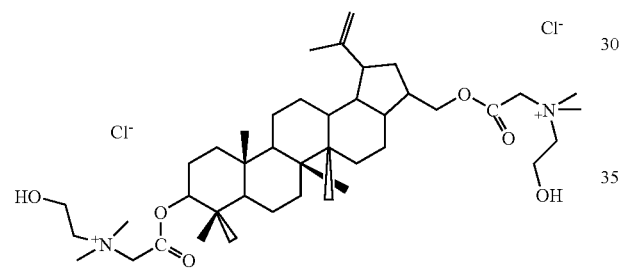

Betulin-3,28-dichloroacetate (3 g, 5 mmol) and N,N-dimethylethanolamine (2.6 g, 30 mmol) were dissolved in 50 ml of dimethylacertamide. The reaction mixture was kept at room temperature overnight (16 hours). The solid part was filtered, washed twice with ethyl ether, dissolved in methanol (4 ml.) and diluted with ethyl ether again. 3.45 g of final product was obtained after filtration and drying in vacuum.

Example 83

Several uncharged or negatively charged triterpenes, and several positively charged triterpenes of the invention were tested for anti-bacterial activity against antibiotic-susceptible and antibiotic resistant strains of four types of bacteria of concern in clinics and hospitals. The triterpenes weres tested in broth culture in triplicate for ability to inhibit bacterial growth. The compounds tested are those listed below.

Compounds 3, 6, 12, 18, 25, and 40 are from the correspondingly numbered examples.

Compound 83 is lupeol.

Compound 84 is lupenone, the compound of formula (I) wherein R$_1$ and R$_2$ together are hydrogen; R$_3$, R$_4$, and R$_5$ together are hydrogen; and R$_6$, R$_7$, and R$_8$ together are oxo.

Compound 85 is lupeneno-1-ene-2-ol, with the structure below

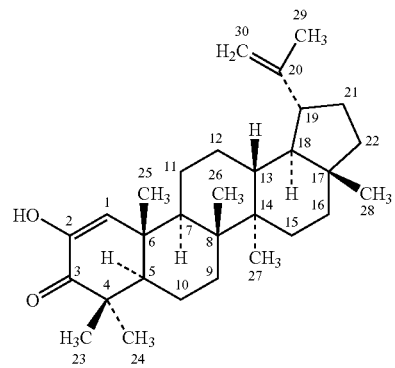

Compound 86 is lupeol-3-maleate, the compound of formula (II) wherein wherein R$_1$ and R$_2$ together are hydrogen; R$_3$, R$_4$, and R$_5$ together are hydrogen; and R$_6$, R$_7$, and R$_8$ together are —OCOCH═CHCOOH.

Compound 87 is lupeol-3-phosphate, the compound of formula (II) wherein wherein R$_1$ and R$_2$ together are hydrogen; R$_3$, R$_4$, and R$_5$ together are hydrogen; and R$_6$, R$_7$, and R$_8$ together are phosphate.

Compound 88 is allobetulone-1-ene-2-ol, with the structure below

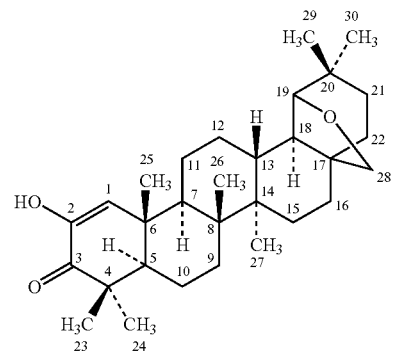

Compound 89 is betulin-3,28,30-triol, the compound of formula (II) wherein wherein R$_1$ and R$_2$ together are hydroxyl; R$_3$, R$_4$, and R$_5$ together are hydroxyl; and R$_6$, R$_7$, and R$_8$ together are hydroxyl.

Compound 90 is betulon-1-ene-2-ol, with the structure below

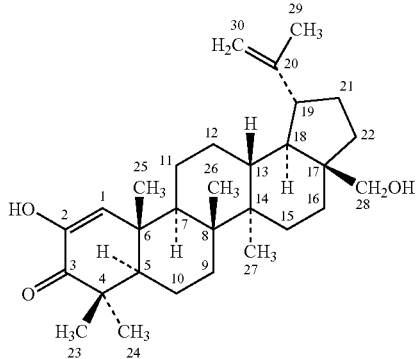

Compound 91 is betulin-3,28-disuccinate, the compound of formula (II) wherein wherein $R_1$ and $R_2$ together are hydrogen; $R_3$, $R_4$, and $R_5$ together are —OCOCH$_2$CH$_2$COOH; and $R_6$, $R_7$, and $R_8$ together are —OCOCH$_2$CH$_2$COOH.

Compound 92 is betulin-28-succinate, the compound of formula (II) wherein wherein $R_1$ and $R_2$ together are hydrogen; $R_3$, $R_4$, and $R_5$ together are —OCOCH$_2$CH$_2$COOH; and $R_6$, $R_7$, and $R_8$ together are hydroxyl.

Compound 93 is betulin-3,28-dimaleate, the compound of formula (II) wherein wherein $R_1$ and $R_2$ together are hydrogen; $R_3$, $R_4$, and $R_5$ together are —OCOCH=CHCOOH; and $R_6$, $R_7$, and $R_8$ together are —OCOCH=CHCOOH.

Compound 94 is betulin-28-maleate, the compound of formula (II) wherein wherein $R_1$ and $R_2$ together are hydrogen; $R_3$, $R_4$, and $R_5$ together are —OCOCH=CHCOOH; and $R_6$, $R_7$, and $R_8$ together are hydroxyl.

Compound 95 is betulin-3,28-bisdiacetyltartrate, the compound of formula (II) wherein wherein $R_1$ and $R_2$ together are hydrogen; $R_3$, $R_4$, and $R_5$ together are —COCHOHCHOHCOCH$_2$COCH$_2$COOH; and $R_6$, $R_7$, and $R_8$ together are —COCHOHCHOHCOCH$_2$COCH$_2$COOH.

Results

The lowest concentration which inhibits bacterial growth is referred to as the minimum inhibitory concentration (MIC), the standard measurement of anti-microbial activity. Table 1 gives approximate MIC values for the 19 triterpenes tested. The standard for antibiotic development in the pharmaceutical industry is that compounds under study must be active at 10 μg/ml or less to be considered for further development. By this criterion, all five of the quaternary amine triterpene derivatives tested were effective against both *S. aureus* and *E. faecium*. In addition, the compounds were approximately equally effective against both antibiotic-resistant and antibiotic-sensitive strains of the two bacteria. In contrast, of the triterpenes not derivatized with a quaternary amine, only lupeol-3-maleate had an MIC of 10 μg/ml or less, and that against only one strain of bacteria Example 84

Methods.

Plots of creeping bentgrass, cv. "Pennlinks," were treated with water based sprays of the test compounds. Sprays were delivered by CO$_2$-charged sprayer to deliver the equivalent of 2 gallons of spray per 1000 sq. ft of plot area. Plots were 15 sq. ft. each, and treatments were mixed to apply material to 75 sq. ft (5 replicates), although only 4 replicates were treated. The quaternary salts of triterpenes were applied at 17.8 g/1000 sq. ft. for 14 days. Daconil Ultrex® was applied at 3.2 oz./1000 sq. ft. for 14 days. The experiment used a randomized complete block design, with 4 replicates per treatment. Disease pressure was high. Pennlinks bluegrass is moderately to highly susceptible to both dollar spot and brown patch. For brown patch, caused by *Rhozoctonia sofani.* a visual estimate of the percent of the plot area affected was recorded. Turf quality was estimated on a 1 to 9 scale, with 1 being worst and 9 being perfect. A rating of 6 is considered acceptable.

Results.

Table 2 and Table 3 report the results of two experiments. The compound numbers in the Tables correspond to the Example numbers above. In Table 3, compounds 15 and 24 suppressed the development of brown patch after the first spray was applied. The other treatments suppressed brown patch also, but to a lesser extent on Jun. 25, 2001, one week after the first treatment was applied. At Jul. 2, 2001, compounds 1, 15, and 24 suppressed dollar spot, but not as well as the chemical standard, Daconil Ultrex®. By Jul. 9, 2001, none of the treatments differed significantly from the control for dollar spot.

On June 25 and Jul. 2, 2001 in Table 3, all of the test compounds apparently decreased brown patch, but only compound 15 (on June 25) and Daconil Ultrex® achieved stastically significant suppression. By Jul. 9, 2001, compounds 7, 18. and 24 were judged to significantly suppress brown patch. On July 16, there were no significant differences regarding brown patch.

In summary, for the first two weeks, all of the tested quaternary amine salts of triterpenes suppressed both dollar spot and brown patch for the first two weeks of treatment in one of the studies. In the study of Table 2, for the compounds appeared to be less effective. Many reasons might account for this, in particular weather and soil conditions.

TABLE 1

Anti-Bacterial Activity of Betulin and Derivatives
(Approximate Minimum Inhibitory Concentration, MIC, μg/ml)

| Test Organism | Compound number | | | | | | | | | | | | | | | | | | |
|---|---|---|---|---|---|---|---|---|---|---|---|---|---|---|---|---|---|---|---|
| | 3 | 6 | 12 | 18 | 25 | 40 | 83 | 84 | 85 | 86 | 87 | 88 | 89 | 90 | 91 | 92 | 93 | 94 | 95 |
| *Staphylococcus aureus* Methicillin-resistant | 5 | 2 | 5 | 5 | 2 | 5 | — | — | 100 | — | — | — | — | — | — | — | 200 | — | — |
| *Staphylococcus aureus* Methicillin-sensitive | 5 | 2 | 2 | 5 | 2 | 5 | — | — | 50 | — | — | — | — | — | 200 | 50 | 200 | 50 | — |
| *Enterococcus faecium* Vancomycin-sensitive | 5 | 5 | 2 | 5 | 5 | 2 | — | — | 20 | 10 | — | — | — | — | — | — | — | 200 | — |
| *Enterococcus faecium* Vancomycin-sensitive | 5 | 10 | 2 | 5 | 10 | 5 | — | — | 50 | 50 | — | — | — | — | — | — | — | 200 | — |
| *Pseudomonas aeruginosa* Multi-drug resistant | — | — | — | — | — | 200 | — | — | — | — | — | — | — | — | — | — | — | — | — |
| *Pseudomonas aeruginosa* Antibiotic sensitive | — | — | — | — | — | 200 | — | — | — | — | — | — | — | — | — | — | — | — | — |
| *Eschericia coli* Ampicillin-resistant | — | — | 50 | — | 100 | 50 | — | — | — | — | — | — | — | — | — | — | — | — | — |
| *Escherichia coli* Ampicillin sensitive | — | — | — | — | 50 | 20 | — | — | — | — | — | — | — | — | — | — | — | — | — |

— = no inhibition of bacterial growth.

TABLE 2

Antifungal Treatment on Turf Grass

| | Jun. 25, 2001 | | | Jul. 2, 2001 | | | Jul. 9, 2001 | | Jul. 16, 2001 | | |
|---|---|---|---|---|---|---|---|---|---|---|---|
| Sample | Dollar Spot # of spots per plot | Brown Patch % of plot infected | Turf Quality | Dollar Spot # of spots per plot | Brown Patch % of plot infected | Turf Quality | Brown Patch % of plot infected | Turf Quality | Dollar Spot # of spots per plot | Brown Patch % of plot infected | Turf Quality |
| Control | 17.0 | 23.8 | 4.63 | 15.8 | 30.5 | 4.75 | 27.5 | 5.00 | 2.5 | 5.0 | 5.72 |
| Comp. 1 | 21.0 | 18.8 | 4.50 | 22.3 | 35.0 | 4.50 | 13.8 | 6.00 | 2.8 | 3.8 | 5.57 |
| Comp. 7 | 18.3 | 24.5 | 4.50 | 22.3 | 20.5 | 4.25 | 20.0 | 4.50 | 2.3 | 3.8 | 5.60 |
| Comp. 14 | 22.3 | 25.8 | 4.38 | 21.8 | 36.8 | 4.25 | 25.0 | 4.63 | 3.5 | 5.0 | 5.60 |
| Comp. 17 | 17.8 | 20.0 | 4.63 | 19.3 | 33.8 | 4.25 | 22.8 | 5.13 | 2.0 | 5.0 | 5.60 |
| Comp. 24 | 17.0 | 15.8 | 4.75 | 16.3 | 30.0 | 4.50 | 14.3 | 5.00 | 2.8 | 2.5 | 5.65 |
| Daconil | 11.3 | 17.5 | 5.25 | 8.3 | 5.8 | 5.75 | 13.3 | 6.00 | 1.3 | 3.8 | 5.85 |

TABLE 3

Antifungal Treatment on Turf Grass

| | Jun. 25, 2001 | | | Jul. 2, 2001 | | | Jul. 9, 2001 | | | Jul. 16, 2001 | |
|---|---|---|---|---|---|---|---|---|---|---|---|
| Sample | Dollar Spot # of spots per plot | Brown Patch % of plot infected | Turf Quality | Dollar Spot # of spots per plot | Brown Patch % of plot infected | Turf Quality | Dollar Spot # of spots per plot | Brown Patch % of plot infected | Turf Quality | Dollar Spot # of spots per plot | Brown Patch % of plot infected |
| Control | 21.3 | 24.5 | 4.00 | 27.0 | 41.3 | 4.38 | 17.8 | 27.5 | 4.88 | 2.0 | 7.5 |
| Comp. 1 | 11.5 | 15.8 | 4.88 | 15.8 | 24.0 | 4.50 | 13.0 | 20.5 | 5.38 | 1.5 | 8.6 |
| Comp. 7 | 14.8 | 17.5 | 4.36 | 21.5 | 25.5 | 4.50 | 14.5 | 10.8 | 5.88 | 2.0 | 8.8 |
| Comp. 14 | 16.3 | 16.3 | 4.88 | 20.8 | 31.3 | 4.75 | 14.5 | 16.5 | 5.00 | 2.8 | 7.5 |
| Comp. 15 | 10.5 | 13.8 | 4.88 | 16.0 | 26.8 | 4.75 | 16.3 | 14.5 | 5.50 | 1.5 | 10.0 |
| Comp. 18 | 16.8 | 14.8 | 4.63 | 20.8 | 37.5 | 4.63 | 14.3 | 12.0 | 5.50 | 1.8 | 6.3 |
| Comp. 24 | 10.8 | 17.0 | 4.75 | 14.0 | 29.5 | 4.50 | 11.3 | 12.5 | 5.50 | 1.5 | 7.5 |
| Daconil | 11.0 | 7.5 | 5.63 | 10.5 | 8.3 | 6.13 | 11.0 | 7.3 | 6.20 | 1.5 | 8.8 |

Example 85

Methods

Plots of creeping bentgrass, cv. Pennlinks, were treated with water-based sprays as in Example 84 at Clemson University. Treatment application dates were May 7, May 14, May 28, and June 11. Plots were rated visually, estimating the percent of the area affected by dollar spot fungus (*Agrostis stolonifera*). Turf quality was rated on a 1 to 9 scale, with 9 being perfect turf, as in Example 84. Disease pressure was moderately high to high when the trial was initiated, with existing dollar spot present. Plots did not receive additional innoculum, as it was not needed.

Results

Table 4 shows the amount of active ingredient applied for each tested compound.

TABLE 4

| Treatment Name | Product Rate (grams active ingredient per 1000 square feet) |
|---|---|
| Comp. 15 | 50 |
| Comp. 17 | 50 |
| Comp. 22 | 50 |
| Comp. 67 | 50 |
| Comp. 56 | 50 |
| Comp. 53 | 50 |
| Comp. 46 | 50 |
| Comp. 55 | 50 |

Tables 5 and 6 show the turf quality and percent area of the plots infected with dollar spot after treatment with the test compounds in duplicate experiments. In both cases all of the tested compounds somewhat reduced the extent of dollar spot infection and somewhat improved turf quality by the end of the treatment trial, compared to the no treatment control. Compound 67 gave the best results.

TABLE 5

| Treatment Name | Turf quality May 27, 2002 | % of area infected Jun. 3, 2002 | Turf quality Jun. 3, 2002 | % of area infected Jun. 3, 2002 | Turf quality Jun. 17, 2002 |
|---|---|---|---|---|---|
| Control | 2.95 b | 28.3 a | 3.95 c | 30.5 a | 4.70 ab |
| Comp. 15 | 3.13 b | 24.3 a | 4.95 abc | 23.0 a | 3.60 b |
| Comp. 17 | 3.10 b | 29.0 a | 4.47 bc | 26.0 a | 4.70 ab |
| Comp. 22 | 3.05 b | 24.5 a | 4.80 abc | 17.3 ab | 5.07 ab |
| Comp. 67 | 4.85 a | 13.0 b | 6.00 a | 9.0 b | 5.80 a |
| Comp. 56 | 4.47 ab | 22.0 a | 5.30 ab | 19.3 ab | 5.38 ab |
| Comp. 53 | 3.60 ab | 22.5 a | 5.18 ab | 19.5 ab | 5.38 ab |
| Comp. 46 | 4.00 ab | 23.5 a | 5.40 ab | 24.0 a | 4.52 ab |
| Comp. 55 | 3.38 ab | 28.8 a | 5.10 ab | 24.3 a | 5.2 ab |
| LSD (P = .05) | 0.941 | 5.38 | 0.773 | 8.49 | 1.072 |
| Standard Deviation | 0.658 | 3.77 | 0.541 | 5.94 | 0.750 |
| CV | 17.83 | 15.44 | 10.56 | 25.24 | 15.49 |
| Bartlett's X2 | 41.594 | 3.327 | 11.42 | 14.151 | 7.6 |
| P(Bartlett's X2) | 0.001* | 0.998 | 0.653 | 0.439 | 0.909 |
| Replicate F | 3.632 | 5.654 | 4.409 | 2.304 | 2.843 |
| Replicate Prob(F) | 0.0204 | 0.0024 | 0.0088 | 0.0907 | 0.0491 |
| Treatment F | 3.335 | 4.371 | 3.225 | 3.741 | 2.065 |
| Treatment Prob(F) | 0.0013 | 0.0001 | 0.0017 | 0.0005 | 0.0354 |

Means followed by same letter do not significantly differ (P = .05, Student-Newman-Keuls)

TABLE 6

| Treatment Name | % of area infected May 8, 2002 | Turf quality May 8, 2002 | % of area infected May 13, 2002 | Turf quality May 13, 2002 | % of area infected May 20, 2002 | Turf quality May 20, 2002 | % of area infected May 27, 2002 |
|---|---|---|---|---|---|---|---|
| Control | 30.0 a | 3.13 a | 28.0 a | 3.15 a | 38.3 a | 2.75 b | 36.3 a |
| Comp. 15 | 30.3 a | 3.00 a | 27.5 a | 3.13 a | 27.3 bc | 3.13 ab | 29.3 a-d |
| Comp. 17 | 31.5 a | 3.00 a | 28.0 a | 3.13 a | 32.0 bc | 3.00 ab | 31.5 ab |
| Comp. 22 | 34.3 a | 3.00 a | 28.5 a | 3.13 a | 31.5 bc | 2.95 ab | 32.0 ab |
| Comp. 67 | 28.3 a | 3.20 a | 26.0 a | 3.17 a | 24.3 c | 3.55 a | 21.0 d |
| Comp. 56 | 31.0 a | 3.13 a | 26.5 a | 3.00 a | 32.0 bc | 3.03 ab | 21.8 cd |
| Comp. 53 | 33.5 a | 3.00 a | 28.5 a | 3.05 a | 27.3 bc | 3.25 ab | 26.8 bcd |
| Comp. 46 | 30.5 a | 3.25 a | 28.0 a | 3.38 a | 25.0 bc | 3.50 a | 26.8 bcd |
| Comp. 55 | 33.5 a | 3.05 a | 30.0 a | 3.00 a | 32.8 b | 2.97 ab | 29.3 a-d |
| LSD (P = .05) | 4.64 | 0.253 | 4.08 | 0.273 | 4.67 | 0.418 | 5.45 |
| Standard Deviation | 3.25 | 0.177 | 2.86 | 0.191 | 3.27 | 0.293 | 3.82 |
| CV | 10.47 | 5.74 | 10.23 | 6.15 | 11.37 | 9.08 | 13.6 |
| Bartlett's X2 | 8.725 | 10.65 | 17.52 | 6.974 | 7.938 | 21.133 | 14.183 |
| P(Bartlett's X2) | 0.848 | 0.222 | 0.23 | 0.801 | 0.893 | 0.07 | 0.436 |
| Replicate F | 21.790 | 10.976 | 6.502 | 5.058 | 5.755 | 3.248 | 6.185 |
| Replicate Prob(F) | 0.0001 | 0.0001 | 0.0010 | 0.0044 | 0.0022 | 0.0311 | 0.0014 |
| Treatment F | 1.152 | 1.113 | 0.505 | 1.421 | 5.743 | 3.277 | 4.520 |
| Treatment Prob(F) | 0.3456 | 0.3750 | 0.9167 | 0.1860 | 0.0001 | 0.0014 | 0.0001 |

Means followed by same letter do not significantly differ (P = .05, Student-Newman-Keuls)

Similar experiments were performed at Rutgers University to test for treatment of bentgrass infected with dollar spot. Test compounds were mixed in aqueous solution with the adjuvant Latron B-1956® (Rohm and Haas) and applied to the grass at a rate of 4.18 fluid ounces per 1000 square feet and an interval of every 7 days. The number of lesions per plot were then counted and averaged over the replicate plots. Treatment with fertilizers or other fungicides were also performed. The results are presented in Table 7. Compound 80 and to a lesser extent compound 65 were particularly effective.

TABLE 7

| Treatment and Rate/1000 sq. ft. | Spray Interval (days)[2] | Number of Lesion Centers/Plot June 18 | Number of Lesion Centers/Plot June 27 |
|---|---|---|---|
| 3A. Comp. 24 11.8 fl oz | — | — | — |
| B. + Latron B-1956 ™ 4.18 fl oz | 7 | 161.0 | 112.5 |
| 4A. Comp. 52 11.8 fl oz | — | — | — |
| B. + Latron B-1956 ™ 4.18 fl oz | 7 | 118.8 | 74.0 |
| 5A. Comp. 54 11.8 fl oz | — | — | — |
| B. + Latron B-1956 ™ 4.18 fl oz | 7 | 158.0 | 125.0 |
| 6A. Comp. 65 11.8 fl oz | — | — | — |
| B. + Latron B-1956 ™ 4.18 fl oz | 7 | 22.5 | 17.5 |
| 7A. Comp. 1 11.8 fl oz | — | — | — |
| B. + Latron B-1956 ™ 4.18 fl oz | 7 | 115.2 | 143.8 |
| 8A. Comp. 3 11.8 fl oz | — | — | — |
| B. + Latron B-1956 ™ 4.18 fl oz | 7 | 200.0 | 187.5 |
| 10A. Comp. 71 14.6 fl oz | — | — | — |
| B. + Latron B-1956 ™ 4.18 fl oz | 7 | 98.0 | 162.5 |
| 11A. Comp. 75 14.6 fl oz | — | — | — |
| B. + Latron B-1956 ™ 4.18 fl oz | 7 | 160.0 | 162.5 |
| 12A. Comp. 78 14.6 fl oz | — | — | — |
| B. + Latron B-1956 ™ 4.18 fl oz | 7 | 159.5 | 107.8 |

TABLE 7-continued

| Treatment and Rate/1000 sq. ft. | Spray Interval (days)[2] | Number of Lesion Centers/Plot | |
|---|---|---|---|
| | | June 18 | June 27 |
| 13A. Comp. 79 14.6 fl oz | — | — | — |
| B. + Latron B-1956 ™ 4.18 fl oz | 7 | 182.5 | 142.5 |
| 14A. Comp. 80 14.6 fl oz | — | — | — |
| B. + Latron B-1956 ™ 4.18 fl oz | 7 | 6.2 | 0.0 |
| 15. FNX-100 ™ 8.0 fl oz | 14 | 159.5 | 187.5 |
| 16. FNX-100 ™ 12.0 fl oz | 14 | 162.0 | 200.0 |
| 17. FNX-100 ™ 16.0 fl oz | 14 | 158.0 | 200.0 |
| 18. PS00KP ™ 2.0 fl oz | 7 | 200.0 | 175.0 |
| 19. 710-140 ™ 10 fl oz | 7 | 125.2 | 200.0 |
| 20. 710-140 ™ 15 fl oz | 7 | 84.2 | 125.2 |
| 21. 710-140 ™ 20 fl oz | 7 | 46.8 | 125.0 |
| 22. 710-140 ™ 15 fl oz | 14 | 133.5 | 162.5 |
| 23. 710-140 ™ 20 fl oz | 14 | 120.8 | 160.0 |
| 24. 710-140 ™ 25 fl oz | 14 | 119.8 | 112.5 |
| 25A. 710-140 ™ 20 fl oz | — | — | — |
| 25B./Daconil Ultrex ™ 82.5SDG 3.25 oz | 14 | 57.8 | 2.0 |
| 26A. 710-140 ™ 20 fl oz | — | — | — |
| 26B./Chipco 26GT 2SC ™ 3.0 fl oz | 14 | 159.5 | 1.8 |
| 27A. 710-140 ™ 20 fl oz | — | — | — |
| 27B./Chipco 26GT 2SC ™ 3.0 fl oz | 14 | 156.8 | 2.8 |
| 28A. 710-140 ™ 20 fl oz | — | — | — |
| 28B./Daconil Ultrex ™ 82.5SDG 3.25 oz | 14 | 200.0 | 6.5 |
| 29A. 710-140 ™ 20 fl oz | — | — | — |
| 29B./710-140 ™ 20 fl oz | 14 | 116.8 | 131.25 |
| 30. 710-150 ™ 20 fl oz | 14 | 99.8 | 141.25 |
| 31. Daconil Ultrex ™ 82.5SDG 1.8 oz | 7 | 1.5 | 0.0 |
| 32. Daconil Ultrex ™ 82.5SDG 3.25 oz | 14 | 25.2 | 0.8 |
| 33. Fertilizer 18-6-12 1.6 oz N + 0.048 oz Fe | 7 | 110.0 | 175.0 |
| 34. Fertilizer 18-6-12 1.6 oz N + 0.048 oz Fe | 14 | 95.5 | 165.0 |
| 35. GE-2 Plus ™ 4 oz | 14 | 156.5 | 175.0 |
| 36. Untreated Control | — | 200.0 | 180.0 |

Example 86

The following illustrate representative pharmaceutical dosage forms, containing a compound of formulas (I)–(IV) ('Compound X'), for therapeutic or prophylactic use in humans or other mammals.

| (i) Tablet 1 | mg/tablet |
|---|---|
| 'Compound X' | 100.0 |
| Lactose | 77.5 |
| Povidone | 1 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| 'Compound X' | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

The compounds of the invention, e.g., compounds of formulas (I)–(IV), may also be formulated into fungicidal compositions or bacteriacidal compositions for use on plants, the compositions comprising at least one compound of the invention and conventional excipients.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

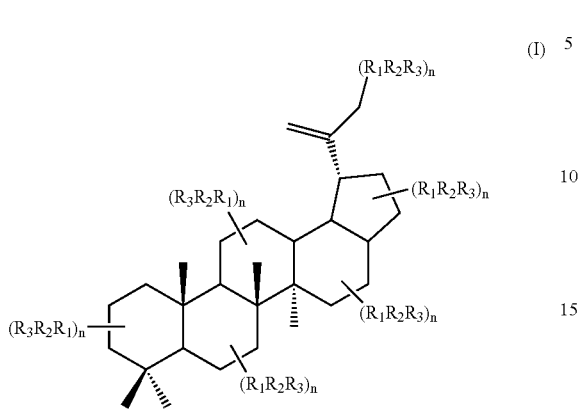

wherein
- each $R_1$ is independently absent, oxy, thio, or imino;
- each $R_2$ is independently absent or alkylene;
- each $R_3$ is independently hydrogen, $N^+$-containing heteroaryl, $N^+$-containing heterocycle, or $-N^+R_aR_bR_c$; provided at least one $R_3$ is $N^+$-containing heteroaryl, $N^+$-containing heterocycle, or $-N^+R_aR_bR_c$;
- $R_a$, $R_b$, and $R_c$ are each independently $(C_1-C_{24})$alkyl, aryl, arylalkyl, heteroarylalkly, heterocycle, or heterocyclealkyl;
- each n is independently 0–4, provided at least one n is not 0;
- any heteroaryl, heterocycle, or $R_a$, $R_b$, or $R_c$ of $R_3$ can optionally be substituted on carbon with one or more alkyl, hydroxyalkyl, arylalkyl, heteroarylalkyl, aryl, heterocycle, heterocyclealkyl, oxo, hydroxy, halo, nitro, cyano, $(C_1-C_6)$alkoxy, trifluoromethyl, $-COOR_d$, $-NR_dR_e$, or cycloalkylalkyl;
- any cycloalkylalkyl can optionally be substituted on carbon with one or more hydroxyl, $N^+$-containing heteroaryl, $N^+$-containing heterocycle, or $-N^+R_aR_bR_c$ $N^+$-containing heteroarylalkyloxy, $N^+$-containing heterocyclealkyloxy, or $-N^+R_aR_bR_c$oxy;
- $R_d$ and $R_e$ are each independently hydrogen or alkyl;
- any alkylene of $R_2$ or alkyl of $R_3$ can optionally be substituted on carbon with one or more oxo, hydroxy, halo, nitro, cyano, $(C_1-C_6)$alkoxy, trifluoromethyl, $-COOR_d$, or $-NR_dR_e$, and optionally interrupted on carbon with one or more oxy, imino, or thio, and is optionally partially unsaturated;

or an acceptable salt thereof.

2. The compound of claim 1 wherein
at least one $R_3$ is $-N^+R_aR_bR_c$ wherein $R_a$ and $R_b$ are each independently $(C_6-C_{24})$alkyl optionally substituted on carbon with one or more oxo, hydroxy, halo, cyano, $(C_1-C_6)$alkoxy, trifluoromethyl, $-COOR_d$, or $-NR_dR_e$, and optionally interrupted on carbon with one or more oxy, imino, or thio, and optionally partially unsaturated.

3. The compound of claim 2 wherein one $R_3$ is $-N^+R_aR_bR_c$ and the other $R_3$s are hydrogen.

4. A compound of formula (II):

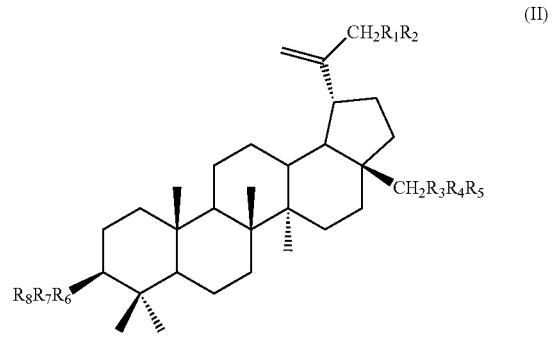

wherein
- $R_1$, $R_4$, and $R_7$ are each independently absent or alkylene;
- $R_3$ and $R_6$ are each independently absent, oxy, thio, or imino;
- $R_2$, $R_5$, and $R_8$ are each independently hydrogen, hydroxyl, $N^+$-containing heteroaryl, $N^+$-containing heterocycle, or $-N^+R_aR_bR_c$; provided at least one of $R_2$, $R_5$, and $R_8$ is $N^+$-containing heteroaryl, $N^+$-containing heterocycle, or $-N^+R_aR_bR_c$;
- $R_a$, $R_b$, and $R_c$ are each independently $(C_1-C_{24})$alkyl, aryl, arylalkyl, heteroarylalkly, heterocycle, or heterocyclealkyl;
- any heteroaryl, heterocycle, $R_a$, $R_b$, or $R_c$ of $R_2$, $R_5$, and $R_8$ can optionally be substituted on carbon with one or more alkyl, hydroxyalkyl, arylalkyl, heteroarylalkyl, aryl, heterocycle, heterocyclealkyl, oxo, hydroxy, mercapto, halo, nitro, cyano, $(C_1-C_6)$alkoxy, trifluoromethyl, $-COOR_d$, $-NR_dR_e$, or cycloalkylalkyl;
- any cycloalkylalkyl can optionally be substituted on carbon with one or more hydroxyl, $N^+$-containing heteroaryl, $N^+$-containing heterocycle, $-N^+R_aR_bR_c$, $N^+$-containing heteroarylalkyloxy, $N^+$-containing heterocyclealkyloxy, or $-N^+R_aR_bR_c$oxy;
- $R_d$ and $R_e$ are each independently hydrogen or alkyl;
- any alkyl or alkylene of $R_1$, $R_2$, $R_4$, $R_5$, $R_7$, or $R_8$ can be optionally substituted on carbon with one or more oxo, hydroxy, halo, nitro, cyano, $(C_1-C_6)$alkoxy, trifluoromethyl, $-COOR_d$, or $-NR_dR_e$, and optionally interrupted on carbon with one or more oxy, imino, or thio, and is optionally partially unsaturated;

or an acceptable salt thereof.

5. The compound of claim 4 wherein $R_2$, $R_5$, and $R_8$ are each independently hydrogen, hydroxyl, N-diazabicyclo[2.2.2]octyl, N-pyridinium, N-alkyl-N-piperidino, N-alkyl-N-morpholino, N-azabicyclo[2.2.2]octyl, or $-N^+R_aR_bR_c$; provided at least one of $R_2$, $R_5$, and $R_8$ is $N^+$-containing heteroaryl, $N^+$-containing heterocycle, or $-N^+R_aR_bR_c$;
wherein N-diazabicyclo[2.2.2]octyl; N-pyridinium; N-alkyl-N-piperidino; N-alkyl-N-morpholino; and N-azabicyclo[2.2.2]octyl can optionally be substituted on one or more suitable carbon atoms with one or more oxo, hydroxy, mercapto, alkyl, hydroxyalkyl, halo, nitro, cyano, $(C_1-C_6)$alkoxy, $-COOR_d$, or $-NR_dR_e$;
wherein any alkyl or alkylene of $R_1$, $R_2$, $R_4$, $R_5$, $R_7$, or $R_8$ can optionally be substituted with one or more oxo or $-NR_dR_e$, and optionally interrupted with one or more oxy, imino, or thio, and can optionally be partially unsaturated.

6. The compound of claim 4 wherein $R_1$ is absent and $R_2$ is hydrogen, N-diazabicyclo[2.2.2]octyl, or N-dimethylamino-N-pyridinium.

7. The compound of claim 4 wherein $R_3$ and $R_4$ are absent, and $R_5$ is hydrogen.

8. The compound of claim 4 wherein
$R_3$ is oxy;
$R_4$ is absent or $(C_1-C_5)$alkylenecarbonyl; and
$R_5$ is hydrogen, N-diazabicyclo[2.2.2]octyl; 4-dimethylamino-N-pyridinium; 4-hydroxybutyl-N-diazabicyclo[2.2.2]octyl; 4-benzyl-N-diazabicyclo[2.2.2]octyl; tetramethylethylenediamine-N-yl; N'-benzyl-N,N,N',N'-tetramethylethylenediamine-N-yl; N-pyridinium; 4-hydroxymethyl-N-pyridinium; 2,4-dimethyl-N-pyridinium; 3,5-dimethyl-N-pyridinium; octyldimethylammonium; or tetradecyldimethylammonium.

9. The compound of claim 4 wherein
$R_6$ is oxy;
$R_7$ is absent or $(C_1-C_5)$alkylenecarbonyl; and
$R_8$ is hydrogen, N-diazabicyclo[2.2.2]octyl; 4-dimethylamino-N-pyridinium; N'-(4-hydroxybutyl)-N-diazabicyclo[2.2.2]octyl; N'-benzyl-N-diazabicyclo[2.2.2]octyl; N,N,N',N'-tetramethylethylenediamine-N-yl; N'-benzyl-N,N,N',N'-tetramethylethylenediamine-N-yl; N-pyridinium; 4-hydroxymethyl-N-pyridinium; 2,4-dimethyl-N-pyridinium; 3,5-dimethyl-N-pyridinium; octyldimethylammonium; tetradecyldimethylammonium; 2-methyl-N-pyridinium; 4-hydroxy-N-methyl-N-piperidinium; or N-methyl-N-morpholino.

10. The compound of claim 4 wherein the compound is
lup-20(29)-ene-3,28-bis-(N-pyridiniumacetate);
lup-20(29)-ene-3-[N-(4-oxybutyl)-1,4-diazabicyclo[2.2.2]octyl-N'-acetate];
lup-20(29)-ene-3,28-bis[N-(1,4-diazabicyclo[2.2.2]octyl)acetate];
lup-20(29)-ene-3,28-bis[N-(N'-benzyldiazabicyclo[2.2.2]octyl)acetate);
lup-20(29)-ene-3,28-bis[N-(N'-(4-oxybutyl)diazabicyclo[2.2.2]octyl)acetate];
lup-20(29)-ene-3-[N-(1,4-diazabicyclo[2.2.2]octyl)acetate];
lup-20(29)-ene-3,28-bis[(tetramethylethylenediamine-N-yl)acetate];
lup-20(29)-ene-3,28-bis[(N'-benzyl-N,N,N',N'-tetramethylethylenediamine-N-yl)acetate];
lup-20(29)-ene-3-[N-(N'-(benzyl)diazabicyclo[2.2.2]octyl)acetate];
bis(N,N'-pyridinium-2-ethyl)lup-20(29)-ene-3,28-dicarbamate;
1-(3,28-(diacetoxy)lup-20(29)-ene-30-yl)-4-(dimethylamino)pyridinium;
lup-20(29)-ene-3,28-bis(N-pyridinium-2-propionate);
lup-20(29)-ene-3,28-bis(N-pyridinium-3-propionate);
lup-20(29)-ene-3,28-bis(N-pyridinium-4-butyrate);
lup-20(29)-ene-3,28-bis(N-pyridinium-4-butyrate);
lup-20(29)-ene-3,28-bis(N-pyridinium-2-butyrate);
1-[3,28-(diacetoxy)lup-20(29)-ene-30-yl]-1,4-diazabicyclo[2.2.2]octyl;
3,28-bis[3-(1-piperidinyl)propanoyloxy]lup-20(29)-ene;
1-(3,28-dihydroxylup-20(29)ene-30-yl)-4-(dimethylamino)pyridinium;
lup-20(29)-ene-3,28-bis[N-(4-dimethylaminopyridinium)-2-propionate];
lup-20(29)-ene-3,28-bis[N-(1,4-diazabicyclo[2.2.2]octyl)-2-propionate];
1-(lup-20(29)-ene-30-yl)-1,4-diazabicyclo[2.2.2]octane;
1-(3,28-dihydroxylup-20(29)-ene-30-yl)-pyridinium;
lup-20(29)-ene-3,28-bis[N-(1,4-diazabicyclo[2.2.2]octyl)-4-butyrate];
1-(3,28-dihydroxylup-20 (29)-ene-30-yl)-[N-3-(hydroxymethyl)pyridinium];
1-(3,28-dihydroxylup-20(29)-ene-30-yl)-[N-(3,5-dimethylpyridinium)];
bis[N-(1,4-diazabicyclo[2.2.2]octyl)-2-ethyl]-lup-20(29)ene-3,28-dicarbamate;
lup-20(29)-ene-3,28-bis[N-(3-oxymethylpyridinium)acetate];
lup-20(29)-ene-3,28-bis[N-(2-oxymethylpyridinium)acetate];
lup-20(29)-ene-3,28-bis[N-(2-methylureapyridinium)acetate];
lup-20(29)-ene-3-[N-(2-oxymethylpyridinium)acetate];
lup-20(29)-ene-3,28-bis[N-(N-methylmorpholino)acetate];
lup-20(29)-ene-3,28-bis[N-(4-hydroxyl-N-methylpiperidino)acetate];
lup-20(29)-ene-3-[N-(3-ureamethylpyridinium)acetate];
lup-20(29)-ene-3-(N-pyridiniumacetate);
lup-20(29)-ene-3,28-bis[N-(1,4-diazabicyclo[2.2.2]octyl)-2-butyrate];
lup-20(29)-ene-3,28-bis[N-(4-dimethylpyridinium)-2-butyrate];
lup-20(29)-ene-3,28-bis[N-(4-dimethylaminopyridinium)-4-butyrate];
lup-20(29)-ene-3,28-bis[N-(4-dimethylaminopyridinium)-3-propionate];
1-(3,$^{28}$-dihydroxylup-20(29)-ene-30-yl)-4-(hydroxymethyl)pyridinium;
1-(3,28-dihydroxylup-20(29)-ene-30-yl)-3-hydroxy-1-azabicyclo[2.2.2]octane;
lup-20(29)-ene-3,28-bis[N-(2,4-dimethylpyridinium)acetate];
lup-20(29)-ene-3,28-bis[N-(3,5-dimethylpyridinium)acetate];
lup-20(29)-ene-3,28-bis[N-(4-dimethylaminopyridinium)acetate];
lup-20(29)-ene-3-[N-(2-methylpyridinium)acetate];
lup-20(29)ene-3-[N-(2,4-dimethylpyridinium)acetate];
lup-20(29)-ene-3-[N-(4-hydroxy-N-methylpiperidino)acetate];
lup-20(29)-ene-3-[N-(N-methylmorpholino)acetate];
lup-20(29)-ene-3-[N-(3,5-dimethylpyridinium)acetate];
lup-20(29)-ene-3-[N-(4-dimethylaminopyridinium)acetate];
lup-20(29)-ene-3,28-bis(octyldimethylammoniumacetate);
lup-20(29)-ene-3-octyldimethylammoniumacetate;
lup-20(29)-ene-3,28-bis(tetradecyldimethylammoniumacetate);
lup-20(29)-ene-3-tetradecyldimethylammoniumacetate;
N,N,N',N'-tetramethylethylenediamine-N,N'-bis-[lup-20 (29)-ene-3-acetate];
1-[(lup-20(29)-en-3β-yl)oxycarbonylmethyl]-4-aza-1-azonia-bicyclo[2.2.2]octane;
1-[(lup-20(29)-en-3β-yl)oxycarbonylmethyl]trimethylammonium; or
1-[(lup-20(29)-en-3β-yl)oxycarbonylmethyl]pyridinium.

11. The compound of claim 4 wherein at least one of $R_2$, $R_5$, and $R_8$ is $-N^+R_aR_bR_c$ wherein $R_a$ and $R_b$ are each independently $(C_6-C_{24})$alkyl optionally substituted on carbon with one or more oxo, hydroxy, halo, cyano, $(C_1-C_6)$ alkoxy, trifluoromethyl, $-COOR_d$, or $-NR_dR_e$, and optionally interrupted on carbon with one or more oxy, imino, or thio, and optionally partially unsaturated.

12. The compound of claim 11 wherein $R_1$ is absent and $R_2$ is hydrogen.

13. The compound of claim 12 wherein the compound is betulin-3,28-bis(didecylmethylammoniumacetoxy).

14. The compound of claim 12 wherein
$R_3$ is absent or oxy, $R_4$ is absent, $R_5$ is hydrogen; or
$R_6$ is oxy, $R_7$ is absent, and $R_8$ is hydrogen.

15. The compound of claim 14 wherein the compound is betulin-3-(didecylmethylammoniumacetoxy).

16. A compound of formula (III)

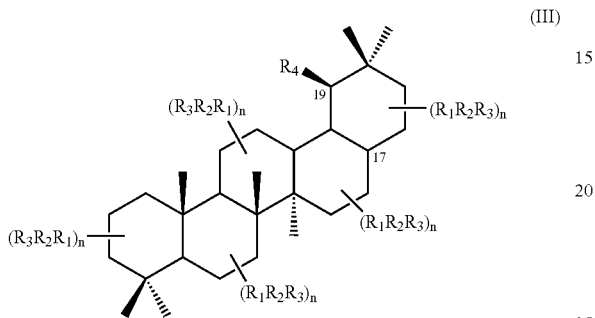

wherein
each $R_1$ is independently absent, oxy, thio, or imino;
each $R_2$ is independently absent or alkylene;
each $R_3$ is independently hydrogen, $N^+$-containing heteroaryl, $N^+$-containing heterocycle, or —$N^+R_aR_bR_c$; provided at least one $R_3$ is $N^+$-containing heteroaryl, $N^+$-containing heterocycle, or $N^+R_aR_bR_c$;
$R_4$ is hydrogen, alkyl, or hydroxyalkyl;
or $R_4$ together with one $R_1R_2R_3$ forms a —$OCH_2$— bridging carbons 19 and 17;
$R_a$, $R_b$, and $R_c$ are each independently ($C_1$–$C_{24}$)alkyl, aryl, arylalkyl, heteroarylalkly, heterocycle, or heterocylealkyl;
each n is independently 0–4, provided at least one n is not 0;
any heteroaryl, heterocycle, or $R_a$, $R_b$, or $R_c$ of $R_3$ can optionally be substituted on carbon with one or more alkyl, hydroxyalkyl, arylalkyl, heteroarylalkyl, aryl, heterocycle, heterocyclealkyl, oxo, hydroxy, halo, nitro, cyano, ($C_1$–$C_6$)alkoxy, trifluoromethyl, —$COOR_d$, —$NR_dR_e$, or cycloalkylalkyl;
any cycloalkylalkyl can optionally be substituted on carbon with one or more hydroxyl, $N^+$-containing heteroaryl, $N^+$-containing heterocycle, —$N^+R_aR_bR_c$, $N^+$-containing heteroarylalkyloxy, $N^+$-containing heterocyclealkyloxy, or —$N^+R_aR_bR_c$oxy;
$R_d$ and $R_e$ are each independently hydrogen or alkyl;
any alkyl or alkylene can optionally be substituted on carbon with one or more oxo, hydroxy, halo, nitro, cyano, ($C_1$–$C_6$)alkoxy, trifluoromethyl, —$COOR_d$, or —$NR_dR_e$, and optionally interrupted on carbon with one or more oxy, imino, or thio, and is optionally partially unsaturated;
or an acceptable salt thereof.

17. The compound of claim 16 wherein
at least one $R_3$ is —$N^+R_aR_bR_c$ wherein $R_a$ and $R_b$ are each independently ($C_6$–$C_{24}$)alkyl optionally substituted on carbon with one or more oxo, hydroxy, halo, cyano, ($C_1$–$C_6$)alkoxy, trifluoromethyl, —$COOR_d$, or —$NR_d$$R_e$, and optionally interrupted on carbon with one or more oxy, imino, or thio, and optionally partially unsaturated.

18. The compound of claim 17 wherein one $R_3$ is —$N^+R_aR_bR_c$ and the other $R_3$s are hydrogen.

19. A compound of formula (IV):

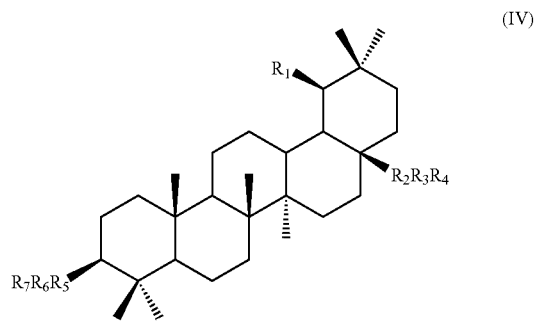

wherein
$R_1$ is hydrogen, alkyl, or hydroxyalkyl;
$R_2$ is oxymethylene, thiomethylene, iminomethylene, or methylene;
$R_3$ and $R_6$ are each independently absent or alkylene;
$R_4$ and $R_7$ are each independently hydrogen, $N^+$-containing heteroaryl, $N^+$-containing heterocycle, or —$N^+R_aR_bR_c$; provided at least one of $R_4$ and $R_7$ is $N^+$-containing heterocycle, —$N^+R_aR_bR_c$; or $R_1$, $R_2$, $R_3$, and $R_4$ are together —O—C(=X)—; wherein X is two hydrogens, oxo, or thioxo (=S);
$R_a$, $R_b$, and $R_c$ are each independently ($C_1$–$C_{24}$)alkyl, aryl, arylalkyl, heteroarylalkyl, heterocycle, or heterocylealkyl;
$R_5$ is absent, oxy, thio, or imino;
any heteroaryl, heterocycle, or $R_a$, $R_b$, or $R_c$ of $R_4$ and $R_7$ can optionally be substituted on carbon with one or more alkyl, hydroxyalkyl, arylalkyl, heteroarylalkyl, aryl, heterocycle, heterocyclealkyl, oxo, hydroxy, halo, nitro, cyano, ($C_1$–$C_6$)alkoxy, trifluoromethyl, —$COOR_d$, —$NR_dR_e$, or cycloalkylalkyl;
any cycloalkylalkyl can optionally be substituted on carbon with one or more hydroxyl, $N^+$-containing heteroaryl, $N^+$-containing heterocycle, —$N^+R_aR_bR_c$, $N^+$-containing heteroarylalkyloxy, $N^+$-containing heterocyclealkyloxy, or —$N^+R_aR_bR_c$oxy;
$R_d$ and $R_e$ are each independently hydrogen or alkyl;
any alkyl or alkylene of $R_3$, $R_4$, $R_6$, or $R_7$ can be optionally substituted on carbon with one or more oxo, hydroxy, halo, aryl, nitro, cyano, ($C_1$–$C_6$)alkoxy, trifluoromethyl, $COOR_d$, or —$NR_dR_e$, and optionally interrupted on carbon with one or more oxy, imino, or thio, and is optionally partially unsaturated;
or an acceptable salt thereof.

20. The compound of claim 19 wherein
$R_1$ is hydrogen, alkyl, or hydroxyalkyl;
$R_2$ is oxymethylene, thiomethylene, iminomethylene, or methylene;
$R_3$ and $R_6$ are each independently absent or ($C_1$–$C_5$) alkylenecarbonyl;
$R_4$ and $R_7$ are each independently hydrogen, N-diazabicyclo[2.2.2]octyl; N-pyridinium; N-alkyl-N-piperidino; N-alkyl-N-morpholino; N-azabicyclo[2.2.2]octyl; or —$N^+R_aR_bR_c$;
or $R_1$, $R_2$, $R_3$, and $R_4$ are together —O—$CH_2$—;

wherein N-diazabicyclo[2.2.2]octyl; N-pyridinium; N-alkyl-N-piperidino; N-alkyl-N-morpholino; and N-azabicyclo[2.2.2]octyl can optionally be substituted on carbon with one or more alkyl, hydroxyalkyl, hydroxy, COOR$_d$, or NR$_d$R$_e$;

wherein R$_a$, R$_b$, and R$_c$ are each independently aryl or (C$_1$–C$_{24}$)alkyl; wherein R$_d$ and R$_e$ are each independently hydrogen or alkyl;

wherein any alkylene or alkyl can optionally be substituted on carbon with one or more oxo, hydroxy, halo, nitro, cyano, trifluoromethyl, COOR$_d$, or —NR$_d$R$_e$, and optionally interrupted with one or more oxy, imino, or thio, and where any alkyl or alkylene can optionally be partially unsaturated.

21. The compound of claim 19, wherein R$_1$, R$_2$, R$_3$, and R$_4$ are together —O—CH$_2$—.

22. The compound of claim 19 wherein R$_5$ is oxy.

23. The compound of claim 19 wherein R$_6$ is acetyl.

24. The compound of claim 19 wherein R$_7$ is N-diazabicyclo[2.2.2]octyl; N-pyridinium; or —N$^+$(CH$_3$)$_3$.

25. The compound of claim 19 wherein the compound is 1-[(19β,28-epoxy-18α-oleanan-3β-yl)oxycarbonylmethyl]-4-aza-1-azonia-bicyclo[2.2.2]octane; [(19β,28-epoxy-18α-oleanan-3β-yl)oxycarbonylmethyl]trimethylammonium; or 1-[(19β,28-epoxy-18α-oleanan-3β-yl)oxycarbonylmethyl]pyridinium.

26. The compound of claim 19 wherein at least one of R$_4$ and R$_7$ is —N$^+$R$_a$R$_b$R$_c$ wherein R$_a$ and R$_b$ are each (C$_6$–C$_{24}$) alkyl optionally substituted on carbon with one or more oxo, hydroxy, halo, cyano, (C$_1$–C$_6$)alkoxy, trifluoromethyl, —COOR$_d$, or —NR$_d$R$_e$, and optionally interrupted on carbon with one or more oxy, imino, or thio, and optionally partially unsaturated.

27. The compound of claim 26 wherein

R$_5$ is oxy, thio, or imino;

R$_6$ is alkylene optionally substituted on carbon with one or more oxo, hydroxy, halo, cyano, (C$_1$–C$_6$)alkoxy, trifluoromethyl, or —NR$_d$R$_e$, and optionally interrupted on carbon with one or more oxy, imino, or thio, and is optionally partially unsaturated; and R$_7$ is —N$^+$R$_a$R$_b$R$_c$ wherein R$_a$ and R$_b$ are each (C$_6$–C$_{24}$) alkyl optionally substituted on carbon with one or more oxo, hydroxy, halo, cyano, (C$_1$–C$_6$)alkoxy, trifluoromethyl, —COOR$_d$, or —NR$_d$R$_e$, and optionally interrupted on carbon with one or more oxy, imino, or thio, and optionally partially unsaturated.

28. The compound of claim 27 wherein the cation of the compound is 3β-[(N-methyl-N,N-didecyl)aminoacetyloxy]-19β,28-epoxy-18β-oleanan chloride.

29. A method of inhibiting or killing a fungus comprising contacting the fungus with an effective anti-fungal amount of a compound of claim 1, wherein the contacting is in vitro or is on or in a plant.

30. The method of claim 29 wherein the contacting is in vitro.

31. The method of claim 29 wherein the contacting is on or in a plant.

32. The method of claim 31 wherein the fungus is growing on turf grass.

33. The method of claim 29 wherein the fungus causes the disease dollar spot or brown patch.

34. A method of inhibiting or killing a bacterium comprising contacting the bacterium with an effective antibacterial amount of a compound of claim 1, wherein the contacting is in vitro or is on or in a plant.

35. The method of claim 34 wherein the contacting is in vitro.

36. The method of claim 34 wherein the contacting is on or in a plant.

37. The method of claim 34 wherein the bacterium is *Staphylococcus* sp. or *Enterococcus* sp.

38. The method of claim 37 wherein the bacterium is *Staphylococcus aureus* or *Enterococcus faecium*.

39. The method of claim 34 wherein the bacterium is antibiotic resistant.

40. A pharmaceutical composition comprising a compound of claim 1, and a pharmaceutically acceptable diluent or carrier.

41. A fungicidal composition comprising a compound of claim 1 and a fungicidal excipient.

42. A method of inhibiting or killing a fungus or bacterium comprising contacting the fungus or bacterium with an effective amount of a compound of claim 16, wherein the contacting is in vitro, or is on or in a plant.

43. The method of claim 42 wherein the contacting is in vitro.

44. The method of claim 42 wherein the contacting is on or in a plant.

45. The method of claim 44 wherein the bacterium is a *Staphylococcus* sp. or *Enterococcus* sp.

46. The method of claim 45 wherein the bacterium is a *Staphylococcus aureus* or *Enterococcus faecium*.

47. The method of claim 44 wherein the bacterium is an antibiotic resistant bacterium.

48. The method of claim 42 wherein the fungus is growing on turf grass and the fungus causes the disease dollar spot or brown patch.

* * * * *

UNITED STATES PATENT AND TRADEMARK OFFICE
CERTIFICATE OF CORRECTION

PATENT NO. : 7,199,114 B2
APPLICATION NO. : 10/893147
DATED : April 3, 2007
INVENTOR(S) : Krasutsky et al.

It is certified that error appears in the above-identified patent and that said Letters Patent is hereby corrected as shown below:

On the Title page, Item (74), in "Attorney, Agent, or Firm", in column 2, line 1, delete "Lungberg," and insert -- Lundberg, --, therefor.
In column 1, line 51, delete "(1991)" and insert -- (1991)) --, therefor.
In column 3, lines 2-3, delete "heteroarylalkly," and insert -- heteroarylalkyl, --, therefor.
In column 3, line 3, delete "heterocylealkyl." and insert -- heterocyclealkyl. --, therefor.
In column 3, line 56, delete "heteroarylalkly," and insert -- heteroarylalkyl, --, therefor.
In column 3, line 57, delete "heterocylealkyl." and insert -- heterocyclealkyl. --, therefor.
In column 4, line 12, after "(III)" insert -- : --.
In column 4, lines 47-48, delete "heterocylealkyl." and insert -- heterocyclealkyl. --, therefor.
In column 4, line 53, delete "–$NR_dR_e$" and insert -- –$NR_dR_e$, --, therefor.
In column 5, line 30, delete "heteroarylalkly," and insert -- heteroarylalkyl, --, therefor.
In column 5, line 31, delete "heterocylealkyl." and insert -- heterocyclealkyl. --, therefor.
In column 6, line 50, delete "accetable" and insert -- acceptable --, therefor.
In column 8, line 40, after "substituents" insert -- . --.
In column 10, line 67, delete "acetate);" and insert -- acetate]; --, therefor.
In column 11, line 4, delete "tetramethyletylenediamine" and insert -- tetramethylethylenediamine --, therefor.
In column 11, line 11, delete "20(29)ene" and insert -- 20(29)-ene --, therefor.
In column 11, line 13, delete "30-yl)4" and insert -- 30-yl)-4 --, therefor.
In column 11, line 17, delete "lup20(29)" and Insert -- lup-20(29) --, therefor.
In column 11, line 19, below "lup-20(29)-ene-3,28-bis(N-pyridinium-4-butyrate);" delete "lup-20(29)-ene-3,28-bis(N-pyridinium-4-butyrate);".(Second Occurrence)
In column 11, line 24, delete "20(29)ene" and insert -- 20(29)-ene --, therefor.
In column 11, lines 39-40, delete "20(29)ene" and insert -- 20(29)-ene --, therefor.
In column 12, line 9, delete "20(29)ene" and insert -- 20(29)-ene --, therefor.
In column 12, line 24, delete "oxycarbonylmethly]4" and insert -- oxycarbonylmethly]-4 --, therefor.
In column 12, line 31, delete "–$N+R_aR_bR_c$" and insert -- –$N^+R_aR_bR_c$ --, therefor.
In column 12, line 33, delete "($C_1$–C6)" and insert -- ($C_1$–$C_6$) --, therefor.
In column 12, line 37, delete "($C_8$–$C_2$4)" and insert -- ($C_8$–$C_{24}$) --, therefor.
In column 12, line 44, delete "–$N^+R_dR_e$," and insert -- –$NR_d,R_e$, --, therefor.
In column 13, line 3, delete "($C_1$–C6)" and insert -- ($C_1$–$C_6$) --, therefor.
In column 13, line 19, delete "$R_a$" and Insert -- $R_c$ --, therefor.
In column 13, line 33, delete "$R_a$" and insert -- $R_g$ --, therefor.
In column 13, line 42, delete "$R_a$" and insert -- $R_c$ --, therefor.
In column 13, line 44, delete "($C_1$–C6)" and Insert -- ($C_1$–$C_6$) --, therefor.
In column 14, line 13, delete "specfic" and insert -- specific --, therefor.

UNITED STATES PATENT AND TRADEMARK OFFICE
CERTIFICATE OF CORRECTION

PATENT NO.         : 7,199,114 B2                                    Page 2 of 7
APPLICATION NO.    : 10/893147
DATED              : April 3, 2007
INVENTOR(S)        : Krasutsky et al.

It is certified that error appears in the above-identified patent and that said Letters Patent is hereby corrected as shown below:

In column 14, line 19, delete "formual" and insert -- formula --, therefor.
In column 14, line 21, delete "formual" and Insert -- formula --, therefor.
In column 15, line 41, delete "R" and Insert -- $R_c$ --, therefor.
In column 16, line 10, delete "heteraryl," and insert -- heteroaryl, --, therefor.
In column 16, line 13, delete "hetercyclealkyl." and insert -- heterocyclealkyl. --, therefor.
In column 16, line 43, delete "betutlin," and insert -- betulin, --, therefor.
In column 16, line 61, delete "$C_{10}$–$C_{24}$" and insert -- ($C_{10}$–$C_{24}$) --, therefor.
In column 17, line 28, delete "reaction-conditions" and insert -- reaction conditions --, therefor.
In column 17, line 54, delete "intert" and insert -- inert --, therefor.
In column 21, line 40, delete "20(29)-ene3,28" and insert -- 20(29)-ene-3,28 --, therefor.
In column 22 (Example 3, Structure II)), lines 49-61, delete " 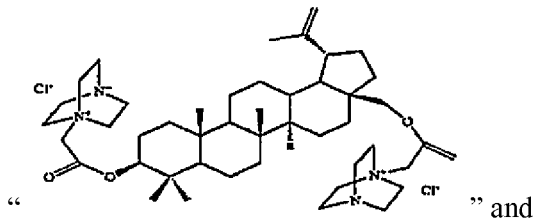 " and insert -- 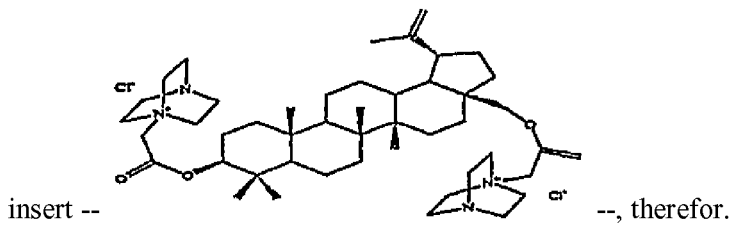 --, therefor.

In column 23, line 5, delete "DMPA" and insert -- DMFA --, therefor.
In column 24, line 32, delete "51.12⁻," and insert -- 51.12, --, therefor.
In column 25, line 36, delete "$CH_3$." and insert -- $CH_3$). --, therefor.
In column 27, line 2, delete "tetramethyltylenediamine" and
insert -- tetramethylethylenediamine --, therefor.
In column 29, line 16, delete "30-yl)4" and insert -- 30-yl)-4 --, therefor.
In column 31, line 2, delete "pyridinium4" and insert -- pyridinium-4 --, therefor.
In column 33, line 10, delete "20(29)-ene 3,28" and insert -- 20(29)-ene-3,28 --, therefor.

UNITED STATES PATENT AND TRADEMARK OFFICE
CERTIFICATE OF CORRECTION

PATENT NO.         : 7,199,114 B2
APPLICATION NO. : 10/893147
DATED                  : April 3, 2007
INVENTOR(S)        : Krasutsky et al.

It is certified that error appears in the above-identified patent and that said Letters Patent is hereby corrected as shown below:

In column 33 (Example 17, Structure I), lines 17-30, delete

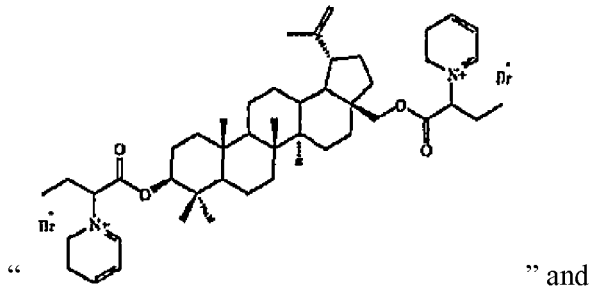

" and

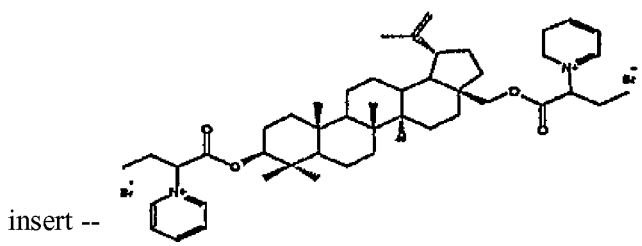

insert -- -- , therefor.

In column 35, line 6, delete "(1OH," and insert -- (10H, --, therefor.
In column 35, line 7, delete "J=1.0 Hz)," and insert -- J=11.0 Hz), --, therefor.
In column 35, line 7, delete "4.554.70" and insert -- 4.55-4.70 --, therefor.
In column 35, line 8, delete "CDCl₃," and insert -- (CDCl₃, --, therefor.
In column 35, line 23, delete "20(29ene" and insert -- 20(29)-ene --, therefor.
In column 36, line 41, delete "diazabicyclo [2.2.2]" and insert -- diazabicyclo[2.2.2] --, therefor.
In column 36, line 42 delete "]-dichloride" and insert --] dichioride --, therefor.
In column 37, line 3, delete "(lup20(29)" and insert -- (lup-20(29) --, therefor.
In column 38, line 3, delete "20(29)ene-30-yl)pyridinium" and insert -- 20(29)-ene-30-yl)-pyridinium --, therefor.
In column 38 (Example 24, Structure I), lines 7-21, delete

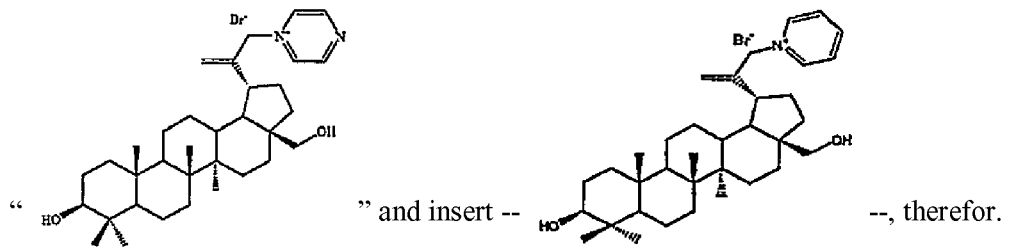

" and insert -- -- , therefor.

In column 38, line 43, delete "octyl)4" and insert -- octyl)-4 --, therefor.

UNITED STATES PATENT AND TRADEMARK OFFICE
CERTIFICATE OF CORRECTION

PATENT NO. : 7,199,114 B2
APPLICATION NO. : 10/893147
DATED : April 3, 2007
INVENTOR(S) : Krasutsky et al.

It is certified that error appears in the above-identified patent and that said Letters Patent is hereby corrected as shown below:

In column 39, line 15, delete "octyl)4" and insert -- octyl)-4 --, therefor.
In column 39, line 67, delete "IBF" and insert -- THF --, therefor.
In column 40, line 5, before "3.14" delete "11H)," and insert -- 1H), --, therefor.
In column 40, line 5, after "5.1 Hz," delete "11H)," and insert -- 1H), --, therefor.
In column 40, line 6, delete "2.40 (m," and insert -- 4.66 (s, --, therefor.
In column 40, line 33, delete "20(29)ene-30-yl)(N" and insert -- 20(29)-ene-30-yl)-(N --, therefor.
In column 41, line 43, delete "acetate)" and insert -- acetate] --, therefor.
In column 42, line 36, delete "20 (29)ene" and insert -- 20(29)-ene --, therefor.
In column 42, line 66, delete "THE" and insert -- THF --, therefor.
In column 43, line 29, delete "TBF" and insert -- THF --, therefor.
In column 44, line 48, delete "20(29)ene-3,28bis" and insert -- 20(29)-ene-3,28-bis --, therefor.
In column 45, line 10, delete "20(29)ene-3,28bis" and insert -- 20(29)-ene-3,28-bis --, therefor.
In column 46, line 52, delete "1,4diazabicyclo[2.2.2]" and insert -- 1,4-diazabicyclo [2.2.2] --,therefor.
In column 47, lines 12-13, delete "dimethylaminopyridinium" and insert -- 4-dimethylaminopyridinium --, therefor.
In column 48, line 25, delete 20(29)-ene3,28" and insert -- 20(29)-ene-3,28 --, therefor.
In column 48, line 26, delete "dimethylaminopyridinium)4" and insert
-- dimethylaminopyridinium)-4 --, therefor.
In column 49 (Example 41, Structure I), lines 15-29, delete

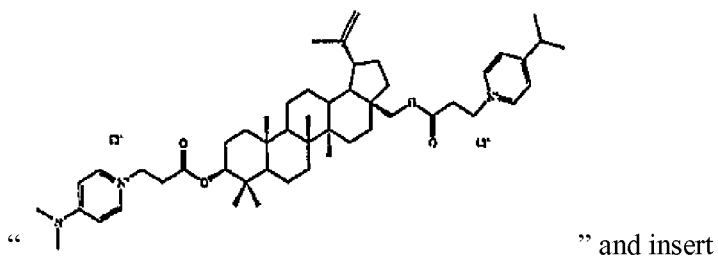

" and insert

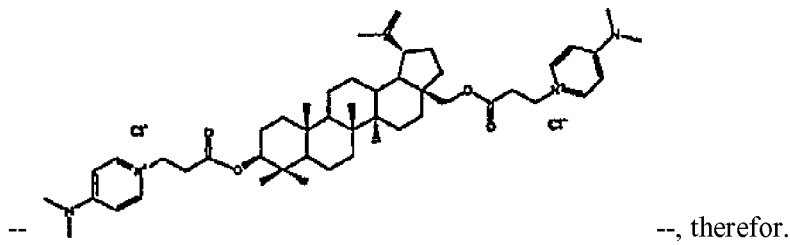

--, therefor.

UNITED STATES PATENT AND TRADEMARK OFFICE
CERTIFICATE OF CORRECTION

PATENT NO. : 7,199,114 B2
APPLICATION NO. : 10/893147
DATED : April 3, 2007
INVENTOR(S) : Krasutsky et al.

It is certified that error appears in the above-identified patent and that said Letters Patent is hereby corrected as shown below:

In column 49, line 40, delete "42M)." and insert -- 42H). --, therefor.
In column 49, line 45, delete "30-yl)4" and insert -- 30-yl)-4 --, therefor.
In column 51, line 3, delete "20(29)ene" and insert -- 20(29)-one --, therefor.
In column 51, line 21, delete "2,15 g" and insert -- 2.15 g --, therefor.
In column 51, line 31, delete "20(29)-ene3,28" and insert -- 20(29)-ene-3,28 --, therefor.
In column 52, line 2, delete "2,15 g" and insert -- 2.15 g --, therefor.
In column 54, line 44, delete "acetate)" and insert -- acetate] --, therefor.
In column 57, lines 2-3, delete "tetradecyldimethylamoniumacetate" and
insert -- tetradecyldimethylammoniumacetate --, therefor.
In column 57, line 41, delete "Lup20(29)-ene3-tetradecyldimethylamoniumacetate" and
insert -- Lup-20(29)-ene-3-tetradecyldimethylammoniumacetate --, therefor.
In column 57, line 67, delete "ADMA14" and insert -- ADMA 14 --, therefor.
In column 58, line 65, delete "1H NMR" and insert -- $^{1}$H NMR --, therefor.
In column 59, line 39, delete "19$\beta$,28epoxy" and insert -- 19$\beta$,28-epoxy --, therefor.
In column 62, line 4, after "vacuum" insert -- . --.
In column 62, line 5, delete "4.71s, 1H)," and insert -- 4.71 (s, 1H), --, therefor.
In column 62, line 46, delete "3,23bis" and insert -- 3,28-bis --, therefor.
In column 63, line 7, after "vacuum" insert -- . --.
In column 63, line 31, after "vacuum" insert -- . --.
In column 65, line 30, delete "91)" and insert -- 91%) --, therefor.
In column 65, line 47, delete "19$\beta$,28epoxy" and insert -- 19$\beta$,28-epoxy --, therefor.
In column 66, line 34, delete "*m," and insert -- (m, --, therefor.
In column 67, line 61, delete "(1, 91 g," and insert -- (1.91 g, --, therefor.
In column 68, line 37, delete "(d. J" and insert -- (d, J --, therefor.
In column 69, line 11, delete "(KBr):" and insert -- IR (KBr): --, therefor.
In column 71, line 2, delete "(116 g," and insert -- (1.16 g, --, therefor.
In column 71, line 43, delete "dimethylacertamide." and insert
-- dimethylacetamlde. --, therefor.
In column 71, line 55, delete "weres" and Insert -- were --, therefor.
In column 71, line 63, delete "(I)" and Insert -- (II)--, therefor.
In column 72, line 19, after "wherein" delete "wherein", (Second Occurrence)
In column 72, line 21, before "$R_8$" delete "5".
In column 72, line 23, after "wherein" delete "wherein". (Second Occurrence)
In column 72, line 45, after "wherein" delete "wherein". (Second Occurrence)
In column 73, line 2, after "wherein" delete "wherein". (Second Occurrence)
In column 73, line 8, after "wherein" delete "wherein". (Second Occurrence)
In column 73, line 12, after "wherein" delete "wherein". (Second Occurrence)
In column 73, line 16, after "wherein" delete "wherein". (Second Occurrence)
In column 73, line 20, after "wherein" delete "wherein". (Second Occurrence)
In column 73, line 42, after "bacteria" insert -- . --.
In column 74, line 16, delete "sofani." and insert -- sofani, --, therefor.

UNITED STATES PATENT AND TRADEMARK OFFICE
CERTIFICATE OF CORRECTION

PATENT NO. : 7,199,114 B2
APPLICATION NO. : 10/893147
DATED : April 3, 2007
INVENTOR(S) : Krasutsky et al.

It is certified that error appears in the above-identified patent and that said Letters Patent is hereby corrected as shown below:

In column 74, line 34, delete "stastically" and insert -- statistically --, therefor.
In column 74, line 35, delete "18." and insert -- 18, --, therefor.
In column 75, line 46, delete "May 7." and insert -- May 7, --, therefor.
In column 81, line 30, in Claim 1, delete "heteroarylalkly," and insert
-- heteroarylalkyl, --, therefor.
In column 81, line 53, in Claim 1, delete "–$NR_d\ R_e$," and insert -- –$NR_dR_e$, --, therefor.
In column 82, line 29, in Claim 4, delete "heteroarylalkly," and insert
-- heteroarylalkyl, --, therefor.
In column 83, line 37, in Claim 10, delete "acetate);" and insert -- acetate]; --, therefor.
In column 83, line 55, in Claim 10, below "lup-20(29)-ene-3,28-bis(N-pyridinium-4-butyrate);" delete "lup-20(29)-ene-3,28-bis(N-pyridinium-4-butyrate);".
(Second Occurrence)
In column 83, line 60, in Claim 10, delete "20(29)ene" and insert -- 20(29)-ene --, therefor.
In column 84, lines 7-8, in Claim 10, delete "20(29)ene" and insert -- 20(29)-ene --, therefor.
In column 84, line 30, in Claim 10, delete "(3,$^{28}$" and insert -- (3,28 --, therefor.
In column 84, line 41, in Claim 10, delete "20(29)ene" and insert -- 20(29)-ene --, therefor.
In column 85, line 11, in Claim 16, after "(III)" insert -- : --.
In column 85, line 33, in Claim 16, delete "$N^+R_aR_bR_c$;" and insert -- –$N^+R_aR_bR_c$; --, therefor.
In column 85, line 39, in Claim 16, delete "heteroarylalkly," and insert
-- heteroarylalkyl, --, therefor.
In column 85, lines 39-40, in Claim 16, delete "heterocylealkyl;" and insert
-- heterocyclealkyl; --, therefor.
In column 86, line 5, in Claim 18, delete "–$N^+R_aR_bR_c$" and insert -- –$N^+R_aR_bR_c$ --, therefor.
In column 86, line 30, in Claim 19, after "$N^+$-containing" insert -- heteroaryl, $N^+$-containing --.
In column 86, lines 34-35, in Claim 19, delete "heterocylealkyl;" and insert
-- heterocyclealkyl: --, therefor.
In column 87, line 15, in Claim 21, delete "claim 19," and insert -- claim 19 --, therefor.

UNITED STATES PATENT AND TRADEMARK OFFICE
CERTIFICATE OF CORRECTION

PATENT NO.       : 7,199,114 B2
APPLICATION NO.  : 10/893147
DATED            : April 3, 2007
INVENTOR(S)      : Krasutsky et al.

It is certified that error appears in the above-identified patent and that said Letters Patent is hereby corrected as shown below:

In column 87, line 49, in Claim 28, delete "18$\beta$-oleanan" and insert -- 18$a$-oleanan --, therefor.

Signed and Sealed this

Thirty-first Day of July, 2007

JON W. DUDAS
*Director of the United States Patent and Trademark Office*